US00RE45968E

(19) United States
(12) Reissued Patent
Minenkova et al.

(10) Patent Number: US RE45,968 E
(45) Date of Reissued Patent: Apr. 12, 2016

(54) VECTOR FOR EFFICIENT SELECTION AND/OR MATURATION OF AN ANTIBODY AND USES THEREOF

(71) Applicant: SIGMA TAU INDUSTRIE FARMACEUTICHE RIUNITE S.p.A., Rome (IT)

(72) Inventors: Olga Minenkova, Montecompatri (IT); Emiliano Pavoni, Grottaferrata (IT)

(73) Assignee: SIGMA TAU INDUSTRIE FARMACEUTICHE RIUNITE S.P.A., Rome (IT)

(21) Appl. No.: 13/831,258

(22) Filed: Mar. 14, 2013

Related U.S. Patent Documents

Reissue of:
(64) Patent No.: 8,003,383
Issued: Aug. 23, 2011
Appl. No.: 12/097,876
PCT Filed: Dec. 27, 2006
PCT No.: PCT/IT2006/000876
§ 371 (c)(1),
(2) Date: Jun. 17, 2008
PCT Pub. No.: WO2007/074496
PCT Pub. Date: Jul. 5, 2007

(30) Foreign Application Priority Data

Dec. 27, 2005 (EP) ..... 05 028 501

(51) Int. Cl.
*C07H 21/04* (2006.01)
*C12P 21/08* (2006.01)
*C12N 15/85* (2006.01)

(52) U.S. Cl.
CPC ..... *C12N 15/85* (2013.01)

(58) Field of Classification Search
None
See application file for complete search history.

(56) References Cited

U.S. PATENT DOCUMENTS

| | | | | |
|---|---|---|---|---|
| 3,663,684 | A | 5/1972 | Freedman et al. | |
| 6,856,208 | B2 | 2/2005 | Lee et al. | |
| 8,003,383 | B2 | 8/2011 | Minenkova et al. | |
| 2008/0241169 | A1 | 10/2008 | Solomon et al. | |
| 2008/0286274 | A1 * | 11/2008 | Minenkova et al. | 424/138.1 |

FOREIGN PATENT DOCUMENTS

| | | |
|---|---|---|
| CA | 2 286 301 | 5/2001 |
| EP | 1 452 599 | 9/2004 |
| EP | 1803814 | 7/2007 |
| JP | 2002/532058 | 10/2002 |
| WO | 90/11092 | 10/1990 |
| WO | 92/01047 | 1/1992 |
| WO | 93/11236 | 6/1993 |
| WO | 97/45544 | 12/1997 |
| WO | 01/36433 | 5/2001 |
| WO | 2005/042578 | 5/2005 |
| WO | 2005/118647 | 12/2005 |
| WO | 2007/074496 | 7/2007 |
| WO | 2012/001004 | 1/2012 |

OTHER PUBLICATIONS

Restriction Requirement issued for U.S. Appl. No. 12/097,876, filed Jun. 17, 2008, in the name of Olga Minenkova et al., mailed on Oct. 28, 2009.
Non-Final Office Action issued for U.S. Appl. No. 12/097,876, filed Jun. 17, 2008, in the name of Olga Minenkova et al., mailed on Jun. 3, 2010.
Final Office Action issued for U.S. Appl. No. 12/097,876, filed Jun. 17, 2008, in the name of Olga Minenkova et al., mailed on Jan. 18, 2011.
Notice of Allowance issued for U.S. Appl. No. 12/097,876, filed Jun. 17, 2008, in the name of Olga Minenkova et al., mailed on May 13, 2011.
Barbas, C.F. III et al., *Phage-display vectors* in Phage Display: A Laboratory Manual Cold Spring Harbor Laboratory Press, 2001, pp. 2.1-2.19, ISSN: 0-87969-546-3.
Barbas, CF., et al., Phage Display: A Laboratory Manual 2001, Cold Spring Harbor Laboratory Press, New York, pp. IV-XVI, 1.1.
Hansen, M.H. et al., *The tumor-infiltrating B cell response in medullary breast cancer is oligoclonal and directed against the autoantigen actin exposed on the surface of apoptotic cancer cells,* PNAS vol. 98, No. 22, pp. 12659-12664 (Oct. 23, 2001).
Bernstein et al., Defective humoral immunity in pediatric immune deficiency syndrome acquired, J. Pediatrics 1985, 107: 352-357.
Clark et al., Bacterial viruses as human vaccines, Expert Rev. Vaccines 2004, 3: 463-476.
Clark et al., Bacterial Pathogenesis Part B: Interaction of Pathogenic Bacteria with Host Cells, Methods in Enzymology 1994, 236: 211-231.
Dente et al., Monoclonal antibodies that recognize filamentous phage: tools for phage: display technology, Gene 1994, 148: 7-13.
Esposito et al., Immunogenicity and therapeutic efficacy of phage-displayed beta-amyloid epitopes, Mol. Immuno. 2008, 45: 1056-1062.
Hawkins et al., Selection of phage antibodies by binding affinity mimicking affinity maturation, J. Mol. Biol. 1992, 226: 889-896.
Hooton et al., Diagnosis and treatment of uncomplicated urinary tract infection, Infectious Disease Clinics of North America 1997, 11: 551-581.
Hopkins et al., Vaginal Mucosal Vaccine for Recurrent Urinary Tract Infections in Women: Results of a Phase 2 Clinical Trial, J. Urology 2007, 177: 1349-1353.
Hopkins et al., Induction of Urinary Tract Infection by Intraurethral Inoculation with *Escherichia coli:* Refining the Murine Model, JID 1995, 171: 462-465.
Krieg, A., Lymphocyte activation by CpG dinucleotide motifs in prokaryotic DNA, Trends in Microbiol. 1996, 4: 73-77.
Langermann et al., Prevention of Mucosal *Escherichia coli* Infection by FimH-Adhesin-Based Systemic Vaccination, Science 1997, 276: 607-611.
Lidqvist et al., Phage display for site-specific immunization and characterization of high-risk human papillomavirus specific E7 monoclonal antibodies, J. Immunol. Methods 2008, 337: 88-96.

(Continued)

*Primary Examiner* — Michael Burkhart
(74) *Attorney, Agent, or Firm* — Steinfl & Bruno LLP

(57) ABSTRACT

It is described a vector suitable for efficient selection and/or maturation of a recombinant antibody characterized in that it contains at least one element able to reduce the expression level and/or has an improved efficiency of display of said recombinant antibody.

21 Claims, 19 Drawing Sheets

(56) References Cited

OTHER PUBLICATIONS

Figure 1:
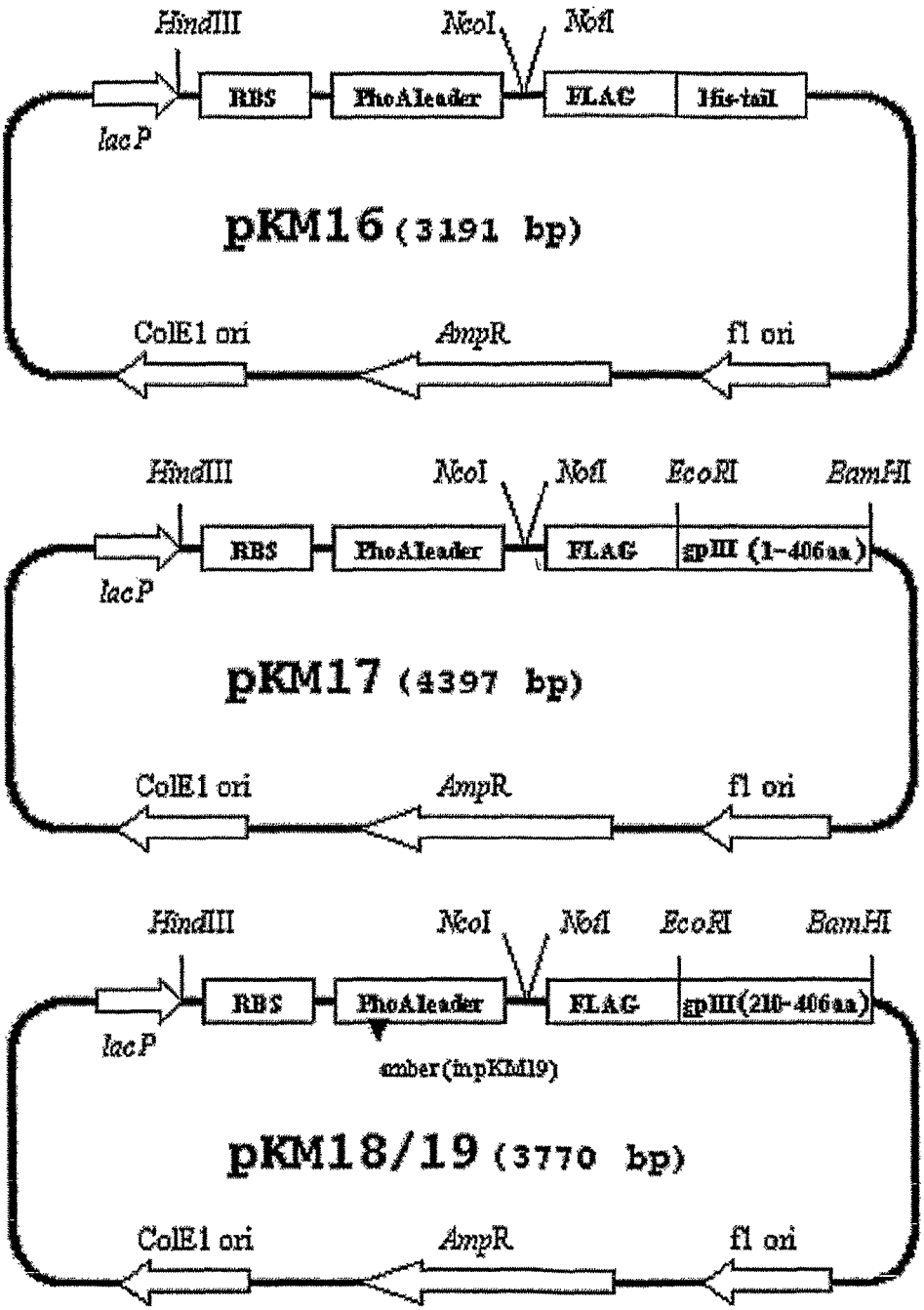

Marvin, D.A., X-Ray Diffraction and Electron Microscope Studies on the Structure of the Small Filamentous Bacteriophage fd, J. Mol. Biol. 1966, 15: 8-17.
Das, P., Vaginal vaccine for recurrent urinary-tract infections, The Lancet 2002, 2: 68.
Parr et al., Immunity to vaginal infection by herpes simplex virus type 2 in adult mice: characterization of the immunoglobulins in vaginal mucus, J. Reproductive Immunology 1998, 38: 15-30.
Roy et al., Oral gene delivery with chitosan-DNA nanoparticles generates immunologic protection in a murine model of peanut allergy, Nat. Med. 1999, 4: 387-39.
Sambrook et al., Molecular Cloning: A Laboratory Manual 1989, Cold Spring Harbor Lab Press, pp. 1-3.
Sato et al., Immunostimulatory Dna sequences necessary for effective intradermal gene immunization, Science 1996, 273: 352-354.
Schulman et al., Oral immunotherapy of recurrent urinary tract infections: A double-blind placebo-controlled multicenter study, J. Urology 1993, 150: 917-921.
Stamm, W., Urinary tract infections, Infectious Disease Clinics of North America 2003, xiii-xiv.
Vieira et al., Production of Single-stranded Plasmid DNA, Methods in Enzymology 1987, 1253: 3-11.
Wedgwood et al., The recognition and classification of immunodeficiency disease with ϕX 174, Birth Defects: Original Article Series 1975, XI: 331-338.
Willis et al., Immunological properties of foreign peptides in multiple display on a filamentous bacteriophage, Gene 1993, 128: 79-83.
International Search Report for PCT Application PCT/EP2011/060839 filed on Jun. 28, 2011 in the name of Sigma-Tau Industrie Farmaceutiche Riunite S.p.A. Mail date: Aug. 12, 2011.
Written Opinion for PCT Application PCT/EP2011/060839 filed on Jun. 28, 2011 in the name of Sigma-Tau Industrie Farmaceutiche Riunite S.p.A. Mail date: Aug. 12, 2011.
Japanese Office Action for Japanese Patent Application No. 2008-548090 filed in the name of Sigma-Tau Industrie Farmaceutiche Riunite S.p.A. Mail date: Apr. 26, 2013 (English Translation & Japanese Original).
Krebber, A. et al., Inclusion of an upstream transcriptional terminator in phage display vectors abolishes background expression of toxic fusions with coat protein g3p, Gene, vol. 178 1996, pp. 71-74.
Beekwilder, J. et al., A phagemid vector using the *E. coli* phage shock promoter facilitates phage display of toxic proteins, Gene, vol. 228 1999, pp. 23-31.
Schimmele, B. et al. Ribosome dislay of mammalian receptor domains. Protein Engineering Design & Selection, vol. 18 (6), 2005, pp. 285-294.
Sletta, H. et al. Broad-host-range plasmid pJB658 can be used for Industrial-Level Production of a Secreted Host-Toxic Single-Chain Antibody Fragment in *Escherichia coli.* Applied and Environmental Microbiology, Vol., vol. 70 (12), Dec. 2004, pp. 7033-7039.
Kotlan, B. et al. A scFv phage display mini library generated from the immunoglobulin repertoire of breast medullary carcinoma infiltrating B lymphocytes. Disease Markers, vol. 16, 2000, pp. 25-27.
Carlos F. Barbas et al. "Assembly of combinatorial antibody libraries on phage surfaces: The gene III site", Proc Natl. Acad. Sci. USA vol. 88, pp. 7978-7982 (Sep. 1991).
Franco Felici, et al. "Selection of antibody ligands from a large library of oligopeptides expressed on a multivalent exposition vector", J. Mol. Bio. 222, pp. 301-310 (1991).
Sten Hammarstrom, "The carcinoembryonic antigen (CEA) family: structures, suggested functions and expression in normal and malignant tissues," Seminars in Cancer Biology, vol. 9, pp. 67-81 (1999).
Margit H. Hansen et al. "Translocation of an intracellular antigen to the surface of medullary breast cancer cells early in apoptosis allows for antigen-driven antibody response elicited by tumor-infiltrating B Cells", The Journal of Immunology 169, pp. 2701-2711 (2002).
Satoru Imahayashi et al., "Tumor Infiltrating B-Cell-Derived IgG Recognizes Tumor Components in Human Lung Cancer", Cancer Investigation 18(6), pp. 530-536 (2000).
Erik S. Kass et al., "Carcinoembryonic antigen as a target for specific antitumor immunotherapy of head and neck cancer", Cancer Research 62, pp. 5049-5057 (Sep. 1, 2002).
Beatrix Kotlan et al., "Novel ganglioside antigen identified by B cells in human medullary breast carcinomas: The proof of principle concerning tumor infiltrating B lymphocytes", The Journal of Immunology 175, pp. 2278-2285 (2005).
Olga Minenkova et al., "Identification of Tumor-Associated Antigens by Screening Phage-Displayed Human cDNA Libraries with Sera From Tumor Patients", Int. J. Cancer, 2003, vol. 106, pp. 534-544.
Lucien Perey et al., "Effects of Differentiating Agents on Cell Surface Expression of the Breast Carcinoma-Associated DF3-P Epitope", Cancer Research 52, pp. 6365-6370 (Nov. 15, 1992).
John B. B. Ridgway et al. "Identification of a Human Anti-CD55 Single-Chain Fv by Subtractive Panning of a Phage Library Using Tumor and Nontumor Cell Lines", Cancer Research 59, pp. 2718-2723 (Jun. 1, 1999).
Rob C. Roovers et al. "Evidence for a bias toward intracellular antigens in the local humoral antitumor immune response of a colorectal cancer patient revealed by phage display", Int. J. Cancer 93, pp. 832-840 (2001).
A. Rothe et al. "Construction of phage display libraries from reactive lymph nodes of breast carcinoma patients and selection for specifically binding human single chain Fv on cell lines", International Journal of Molecular Medicine, vol. 14, pp. 729-735 (2004).
Brigitte Sanzey, "Modulation of Gene Expression by Drugs Affecting Deoxyribonucleic Acid Gyrase", Journal of Bacteriology vol. 138, No. 1, pp. 40-47 (Apr. 1979).
Mohsen Shadidi et al., "An Anti-leukemic single chain Fv antibody selected from a synthetic human phage antibody library", Biochemical and Biophysical Research Communications 280, pp. 548-552 (2001).
K. Sikora et al. "Human hybridomas from malignant gliomas", The Lancet vol. 1, Issue 8262, pp. 11-14(1982).
Donald B. Smith et al. "Single-step purification of polypeptides expressed in *Escherichia coli* as fusions with glutathione S-transferase", Gene 67, pp. 31-40 (1988).
Herbert D. Soule et al. "Isolation and characterization of a spontaneously immortalized human epithelial cell line, MCF-10", Cancer Research 50, pp. 6075-6086 (Sep. 15, 1990).
John A. Thompson et al. "Carcinoembryonic antigen gene family: Molecular biology and clinical perspectives", Journal of Clinical Laboratory Analysis 5, pp. 344-366 (1991).
Ming-Yan Xu et al., "Production of a human signle chain-variable fragment antibody against esophageal carcinoma", World J. Gastroenterol 10(18), pp. 2619-2623 (2004).
Luciano Zardi et al., "Transformed human cells produce a new fribronectin isoform by preferential alternative splicing of a previously unobserved exon." The EMBO Journal vol. 6, No. 8, pp. 2337-2342 (1987).
Hua Zhang et al. "A human monoclonal antimelanoma single-chain Fv derived from tumor-infiltrating lymphocytes", Cancer Research 55, pp. 3584-3591 (Aug. 15, 1995).
European Search Report issued for European Application No. EP05028501.4 filed Dec. 27, 2005 in the name of Sigma-Tau. Mailed Aug. 18, 2006.
O'Connor, C., et al., Highly repressible expression system for cloning genes that specify potentially toxic proteins, Journal of Bacteriology 1987, 169: 4457-4462.
Kimata, K., et al., cAMP receptor protein-cAMP plays a crucial role in glucose-lactose diauxie by activating the major glucose transporter gene in *Escherichia coli,* PNAS 1997, 94: 12914-12919.
Richard J. Simpson, Chapter title "Characterization of protein complexes" in *Proteins and proteomics: A Laboratory Manual,* 2002, pp. 705.
Barbas III, CF., et al., Phage Display: A Laboratory Manual 2001, Cold Spring Harbor Laboratory Press, New York, pp. IV-XVI, 1.1.
PCT International Search Report for PCT/IT2006/000876 filed on Dec. 27, 2006 in the name of Sigma-Tau Industrie Farmaceutiche Riunite S.p.A. et al. Mailed Nov. 13, 2007.
Jamie K. Scott et al., "Phage-display vectors" in Phage Display: A Laboratory Manual Cold Spring Harbor Laboratory Press; pp. 2.1-2. 19, 2001 ISSN: 0-87969-546-3.

(56) References Cited

OTHER PUBLICATIONS

Emiliano Pavoni et al., "Identification of a panel of tumor-associated antigens from breast carcinoma cell lines, solid tumors and testis cDNA libraries displayed on lambda phage" in BMC Cancer, 4:78; Nov. 12, 2004.
Germaine Fuh et al., "Efficient phage display of polypeptides fused to the carboxy-terminus of the M13 gene-3 minor coat protein" in FEBS Letters, vol. 480, pp. 231-234; 2000.
Gregory A. Weiss et al. "Design and evolution of artificial M13 coat proteins" in Journal of Molecular Biology, vol. 300, No. 1, pp. 213-219, Jun. 30, 2000.
Heike A. Held et al., "Comprehensive mutational analysis of the M13 major coat protein: improved scaffolds for C-terminal phage display" in Journal of Molecular Biology, vol. 340, No. 3, pp. 587-597, Jul. 9, 2004.
S.G. Park et al. "Affinity maturation of natural antibody using a chain shuffling technique and the expression of recombinant antibodies in *Escherichia coli"* in Biochem. Biophys. Res. Commun., 2000, vol. 275, No. 2, pp. 553-557; (Abstract).
D. O'Connell et al. "Phage versus Phagemid Libraries for Generation of Human Monoclonal Antibodies" in J. Molec. Biol., 2002, vol. 321, No. 1, pp. 49-56.
International Preliminary Report on Patentability issued on Jul. 1, 2008, for PCT Application No. PCT/IT2006/000876 filed Dec. 27, 2006 in the name of Sigma-Tau.
R.S. Williams et al., "Introduction of foreign genes into tissues of living mice by DNA-coated microprojectiles", Proc. Natl. Acad. Sci. USA, vol. 88, pp. 2726-2730, 1991.
E.F. Fynan et al., "DNA vaccines: Protective immunizations by parenteral, mucosal, and gene-gun inoculations", Proc. Natl. Acad. Sci. USA, vol. 90, pp. 11478-11482, 1993.
C.M. Bearden et al., "Rituximab inhibits the in vivo primary and secondary antibody response to a neoantigen, bacteriophage phiX174." Am J Transplant. Jan. 2005;5(1 ):50-7.
C.K. Garofalo et al, "*Escherichia coli* from urine of female patients with urinary tract infections is competent for intracellular bacterial community formation." Infect Immun. Jan. 2007; 75(1):52-60.
M.J. McCluskie et al., "CpG DNA is a potent enhancer of systemic and mucosal immune responses against hepatitis B surface antigen with intranasal administration to mice." J Immunol. Nov. 1, 1998; 161(9):4463-6.
O.O. Minenkova, et al., "Design of specific immunogens using filamentous phage as the carrier." Gene. 1993; 128(1):85-8.
I.U. Mysorekar, et al., "Mechanisms of uropathogenic *Escherichia coli* persistence and eradication from the urinary tract." Proc Natl Acad Sci US A. Sep. 19, 2006; 103(38):14170-5.
K.G. Naber et al., "Immunoactive prophylaxis of recurrent urinary tract infections: a meta-analysis." Int J Antimicrob Agents. Feb. 2009; 33(2): 111-9.
H.D. Ochs et al., "Immunologic responses to bacteriophage phi-X 174 in immunodeficiency diseases." J Clin Invest. Dec. 1971; 50(12):2559-68.
T.V. Poggio et al., "Intranasal immunization with a recombinant truncated FimH adhesin adjuvanted with CpG oligodeoxynucleotides protects mice against uropathogenic *Escherichia coli* challenge." Can J Micro biol. 2006; 52(11):1093-102.
C.S. Reigstad et al., "Functional genomic studies of uropathogenic *Escherichia coli* and host urothelial cells when intracellular bacterial communities are assembled." J Biol Chem. Jul. 20, 2007; 282(29):21259-67.
V. Tchesnokova et al., "Integrin-like allosteric properties of the catch bond-forming FimH adhesin of *Escherichia coli."* J Biol Chem. Mar. 21, 2008;283(12):7823-33. Epub Jan. 3, 2008.
K. Thankavel et al. "Localization of a domain in the FimH adhesin of *Escherichia coli* type 1 fimbriae capable of receptor recognition and use of a domain-specific antibody to confer protection against experimental urinary tract infection." J Clin Invest. Sep. 1, 1997;100(5): 1123-36.
J. Clark et al., "Bacteriophages and biotechnology: vaccines, gene therapy and antibacterials." Trends in Biotechnology, May 2006, LNKd-PUBMED:16567009, vol. 24, No. 5; pp. 212-218.
S. Langermann et al, "Vaccination utilizing the FimCH complex as a strategy to prevent *Escherichia coli* urinary tract infections." The Journal of Infectious Diseases, Mar. 1, 2001, LNKD-PUBMED:11171023, vol. 183 Suppl 1, pp. S84-S86.
Sambrook J. et al. *Molecular cloning: A laboratory manual,* vol. 1, 2nd edition. Cold Spring Harbor: Cold Spring Harbor Laboratory Press; 1989: 4.17.
Scott, J.K. et al. et al., "Phage-display vectors" in *Phage Display: A Laboratory Manual, Cold Spring Harbor Press;* pp. 2.1-2.19, 2001.
Restriction Requirement mailed on Jun. 14, 2013 for U.S. Appl. No. 13/806,609, filed Jan. 30, 2013 in the name of Rita De Santis et al.
Non-Final Office Action mailed on Jun. 14, 2013 for U.S. Appl. No. 13/806,609, filed Jan. 30, 2013 in the name of Rita De Santis et al.
Greenspan, N.S. et al. "Defining epitopes: It's not as easy as it seems." Nature Biotechnology. vol. 17. Oct. 1999, pp. 936-937.
Bowie, J.U. et al. "Deciphering the Message in Protein Sequences: Tolerance to Amino Acid Substitutions." Science, New Series. vol. 247 (4948). Mar. 1990, pp. 1306-1310.
Goldsmith, M.E. And Konigsberg, W.H. "Adsorption Protein of the Bacteriophage fd: Isolation, Molecular Properties, and Location in the Virus." Biochemistry, vol. 16, No. 12, pp. 2686-2694. 1977.
Non-Final Office Action issued for U.S. Appl. No. 13/806,609, filed Jan. 30, 2013 in the name of Rita De Santis et al. Mail date: Dec. 27, 2013.
Final Office Action issued for U.S. Appl. No. 13/806,609, filed Jan. 30, 2013 in the name of Rita De Santis et al. Mail date: Oct. 23, 2014.
Marciano, D.K. et al. "An Aqueous Channel for Filamentous Phage Export." Science, vol. 284, pp. 1516-1519. May 1999.
Scott et al. (Phage Display: A Laboratory Manual, Cold Spring Harbor Lab. Press, p. 2.1-2.19 (2001)).*
Park et al. (Biochem. Biophys. Res. Commun. Aug. 28, 2000;275(2):553-7; Abstract).*
O'Connell et al. (J. Molec. Biol. Aug. 2, 2002; 321(1):49-56).*
Carlos F. Barbas et al. "Assembly of combinatorial antibody libraries on phage surfaces: The gene III site", Proc. Natl. Acad. Sci. USA vol. 88, pp. 7978-7982 (Sep. 1991).
J. Beekwilder et al. "A phagemid vector using the *E. coli* phage shock promoter facilitates phage display of toxic proteins", GENE 228, pp. 23-31 (1999).
Elisa Beghetto et al. "Discovery of novel *Streptococcus pneumonia* antigens by screening a whole genome-display library", FEMS Microbial Lett. 262, pp. 14-21 (2006).
S. B. Brown et al. "Catalatic activity of iron (III)-centered catalysts", Biochem J. 117, pp. 741-744 (1970).
M. A. Clark et al. "Isolation of human anti-c-erbB-2 Fabs from a lymph node-derived phage display library", Clin. Exp. Immunol 109, pp. 166-174 (1997).
Julia A. Coronella et al. "Antigen-driven oligoclonal expansion of tumor-infiltrating B cells in infiltrating ductal carcinoma of the breast", The Journal of Immunology 169, pp. 1829-1836 (2002).
Julia A. Coronella et al. "Evidence for an antigen-driven humoral immune response in medullary ductal breast cancer", Cancer Research 61, pp. 7889-7899 (Nov. 1, 2001).
Julia A. Coronella-Wood et al. "Naturally occurring B-cell responses to breast cancer", Cancer Immunol Immunother 52, pp. 715-738 (2003).
J. O. Drife et al. "Immunoglobin synthesis in the "resting" breast", British Medical Journal 2, pp. 503-506 (1976).
Pat Edelmann et al. "Nonsense suppression context effects in *Escherichia coli* bacteriophage T4", Mol. Gen. Genet. 207, pp. 517-518 (1987).
Franco Felici, "Selection of antibody ligands from a large library of oligopeptides expressed on a multivalent exposition vector", J. Mol. Bio. 222, pp. 301-310 (1991).
Sten Hammarstrom, "The carcinoembryonic antigen (CEA) family" Cancer Biology, vol. 9, pp. 67-81 (1999).
Margit H. Hansen, "Translocation of an intracellular antigen to the surface of medullay breast cancer cells early in apoptosis allows for antigen-driven antibody response elicited by tumor-infiltrating B Cells", The Journal of Immunology 169, pp. 2701-2711 (2002).

(56) References Cited

OTHER PUBLICATIONS

Margit H. Hansen et al. "The tumor-infiltrating B cell response in medullary breast cancer is oligoclonal and directed against the autoantigen actin exposed on the surface of apoptotic cancer cells", PNAS vol. 98, No. 22, pp. 12659-12664 (Oct. 23, 2001).
Satoru Imahayashi et al., "Tumor infiltrating C-cell-derived IgG recognizes tumor components in human ling cancer", Cancer Investigation 18(6), pp. 530-536 (2000).
Erik S. Kass et al., "Carcinoembryonic antigen as a target for specific antitumor immunotherapy of head and neck cancer", Cancer Research 62, pp. 5049-5457 (Sep. 1, 2001).
Beatrix Kotlan et al., "Novel gangoslide antigen identified by B cells in human medullary breast carcinomas: The proof of principle concerning tumor infiltrating B lymphocytes", The Journal of Immunology 175, pp. 2278-2285 (2005).
Titus Kretzschmar et al., "Evaluation of antibodies fused to minor coat protein III and major coat protein VIII of bacteriophage M13", GENE 155, pp. 61-65 (1995).
Michael A. McGuckin et al. "Prognostic Significance of MUC1 Epithelial Mucin Expression in Breast Cancer", Human Pathology vol. 26, No. 4 pp. 432-439 (1995).
Jeffrey H. Miller et al. "Effects of Surrounding Sequence on the Suppression of nonsense codons", J. Mol. Bio. 164, pp. 59-71 (1983).
Philippa M. O'Brien, "Immunoglobulin genes expressed by B-lymphocytes infiltrating cervical carcinomas show evidence of antigen-driven selection", Cancer Immunol Immunother 50, pp. 523-532 (2001).
Emilian Pavoni et al., "New display vector reduces biological bias for expression of antibodies in *E. coli"*, GENE 391, pp. 120-129 (2007).
Emilian Pavoni et al., "Selection, affinity maturation, and characterization of human scFv antibody against CEA protein", BMC Cancer 6:41 (2006).
Lucien Perey et al., "Effects of differentiating agents on cell surface expression of the breast carcinoma-associated DF3-P epitope", Cancer Research 52, pp. 6367-6370 (Nov. 15, 1992).
Alessandro Pini et al. "Design and use of a phage display library", The Journal of Biological Chemistry, vol. 273, pp. 21769-21776 (1998).
Cornelis J. A. Punt et al. "Anti-tumor antibody produced by human tumor-infiltrating and peripheral blood B lymphocytes", Cancer Immunol Immunother 38, pp. 225-232 (1994).
John B. B. Ridgway et al. "Identification of a human anti-CD55 Single-chin Fv by substractive panning of a phage library using tumor and nontumor cell lines", Cancer Research 59, pp. 2718-2723 (Jun. 1, 1999).
Rob C. Foovers et al. "Evidence for a bias toward intracellular antigens in the local humoral anti-tumor immune response of a colorectal cancer patient revealed by phage display", Int. J. Cancer 93, pp. 832-840 (2001).
A. Rothe et al. "Construction of phage display libraries from reactive lymph nodes of breast carcinoma patients and selection for specifically binding human single chain Fv on cell lines", International Journal of Molecular Medicine 14, pp. 729-735 (2004).
Brigitte Sanzey, "Modulation of Gene Expresssion by Drugs Affecting Deoxyribonucleic Acid Gyrase", Journal of Bacteriology vol. 138, No. 1, pp. 40-47 (Apr. 1979).
Mohsen Shadid et al., "An Anti-leukemic single chain Fv antibody selected from a synthetic human phage antibody library", Biochemical and Biophysical Research Communications 280, pp. 548-552 (2001).
K. Sikora et al. "Human hybridomas from patients with malignant disease", Br. J. Cancer 47, pp. 135-145 (1983).
K. Sikora et al. "Human hybridomas from malignant gliomas", The Lancet vol. 1, Issue 8262, pp. 1-14(1982).
Donald B. Smith et al. "Single-step purification of polypeptides expressed in *Eschericia coli* as fusions with glutathione S-transferase", GENE 67, pp. 31-40 (1988).
Herbert Soule et al. "Isolation and characterization of a spontaneously immortalized human epithelial cell line, MCF-10", Cancer Research 50, pp. 6075-6086 (Sep. 15, 1990).
John A. Thompson et al. "Cancinoembryonic antigen gene family: Molecular biology and clinical perspectives", Journal of Clinical Laboratory Analysis 5, pp. 244-366 (1991).
Katherine P. Topping et al., "Isolation of human colorectal tumor reactive antibodies using phage display technology", International Journal of Oncology 16, pp. 187-195 (2000).
Herren Wu et al., "Cloning, isolation and characterization of human tumor in situ monoclonal antibodies", Cancer Immunol Immunother 51, pp. 79-90 (2002).
Ming-Yanh Xu et al., "Production of a human signle chain-variable fragment antibody against esophageal carcinoma", World J. Gastroenterol 10(18), pp. 2619-2623 (2004).
Manabu Yasuda et al. "Tumor-infiltrating B lymphocytes as a potential source of identifying tumor antigen in human lung cancer", Cancer Research 62, pp. 1751-1756 (Mar. 15, 2002).
Luciano Zardi et al., "Transformed human cells produce a new fribonectin isoform by preferential alternative splicing of a previously unobserved exon." The EMBO Journal vol. 6, No. 8, pp. 2337-2342 (1987).
Hu Zhang et al. "A human monoclonal antimelanoma single-chain Fv derived from tumor-infiltrating lymphocytes", Cancer Research 55, pp. 3584-3591 (Aug. 15, 1995).
J. McCafferty et al., "Antibody Engineering: A Practical Approach" (soft cover) Oxford University Press, 1996, ISBN 0-19-963592-7.
PCT International Search Report for PCT/IT2006/000876 filed on Dec. 27, 2006 in the name of Sigma-Tau Industrie Farmaceutiche Riunite S.P.A. et al.
Jamie K. Scott et al., "Phage-display vectors" in Phage Diaplay: A Laboratory Manual Cold Spring Harbor Laboratory Press; pp. 2.1-2. 19, 2001 ISSN: 0-87969-546-3.
Emiliano Pavoni et al., "Identification of a panel of tumor-associated antigens from breast carcinoma cell lines, solid tumors and testis cDNA libraries displayed on lambda phage" in BMC Cancer, p. 78; Nov. 12, 2004.
S. Thirion et al., "Mono-and bispecific single-chain antibody fragments for cancer therapy" in European Journal of Cancer Prevention, vol. 5, No. 6, pp. 507-511, Dec. 1996.
Olga Minenkova et al., "Identification of tumor-associated antigens by screening phage-displayed human cDNA libraries with sera from tumor patients" in International Journal of Cancer, vol. 106, No. 4, pp. 534-544, Sep. 10, 2003.
Gabriella Garufi et al., "Display libraries on bacteriophage iambda capsid" in Biotechnology Annual Review; vol. 11, pp. 153-190, Oct. 7, 2005.
Germaine Fuh et al., "Efficient phage display of polypeptides fused to the carboxy-terminus of the M13 gene-3 minor coat protein" in FEBS Letters, vol. 480 No. 2-3; Sep. 1, 2000.
Gregory A. Weiss et al. "Design and evolution of artifical M13 coat proteins" in Journal of Molecular Biology, London, vol. 300, No. 1, pp. 213-219, Jun. 30, 2000.
Heike A. Held et al., "Comprehensive mutational analysis of the M13 major coat protein: improved scaffolds for C-terminal phage display" in Journal of Molecular Biology, London, vol. 340, No. 3, pp. 587-597, Jul. 9, 2004.
Emiliano Pavoni et al., "New display vector reduces biological bias for expression of antibodies in *E. coli"* in Gene, vol. 391, No. 1-2, pp. 120-129, Apr. 15, 2007.
European Search Opinion issued for European Application No. EP05028501.4 filed Dec. 27, 2005 in the name of SIGMA-TAU.
Crissman, J., et al., Gene-III protein of filamentous phages: evidence for a carboxyl-terminal domain with a role in morphogenesis, Virology 1984, 132: 445-455.
Dickson, R., et al., Genetic Regulation: the lac control region, Science 1975, 187: 27-35.
O'Connor, C., et al., Highly repressible expression system for cloning genes that specify potentially toxic proteins, Journal of Bacteriology 1987, 169:4457-4462.

(56) References Cited

OTHER PUBLICATIONS

Parker, J., Errors and alternatives in reading the universal genetic code, Microbiological reviews 1989, 53: 273-298.
Kimata, K., et al., cAMP receptor protein-cAMP palys a crucial role in glucose-lactose diauxie by activating the major glucose transporter gene in *Escherichia coli,* PNAS 1997, 94: 12914-12919.
Simpson, Characterization of protein complexes, Science 2002, 705.
Viti, F., et al., Design and use of phage display libraries for the selection of antibodies and enymes, Methods in Enzymology 2000, 326: 480-505.
Barbas, CF., et al., Phage Display: A Laboratory Manual 2001, Cold Spring Harbor Laboratory Press, New York, pp. IV-XVI, 1.1;.

* cited by examiner

```
1   GCCCAATACG CAAACCGCCT CTCCCCGCGC GTTGGCCGAT TCATTAATG
                                                        >Plac>
                                                            C

    51  AGCTGGCACG ACAGGTTTCC CCACTGGAAA GCGGGCAGTG AGCGCAACGC

   101  AATTAATGTG AGTTAGCTCA CTCATTAGGC ACCCCAGGCT TTACACTTTA

   151  TGCTTCCGGC TCGTATGTTG TGTGGA
                                   <Plac<
                                   ATTG TGAGCGGATA ACAATTTCAC

   201  ACAAGATCTA GCTATTCTAG AGATTA
                                   >alpha-peptide>
                                   CGCC AAGCCCC
                                               >f1.seg>
                                               GTA TTTTACCCGT

   251  TTAATGG
                          M   K   q   S   T   I   A   L   A   L   L
AAGCTT ATAAGGAGGAAATCCTC ATG AAA TAG AGC ACC ATC GCA CTG GCA CTG TTA
HindIII     RBS                  amb

                                  -1 | +1
P   L   L   P   T   P   V   T   K   A   R   T   M   V   S   L   A
CCG TTA CTG TTC ACC CCG GTT ACC AAA GCA CGT ACC ATG GTT TCC CTT GCG
                                            NcoI
A   A   G   D   Y   K   D   D   D   D   K
GCC GCA GGA GAC TAC AAA GAC GAC GAC GAC AAA GAA TTC
NotI                                        EcoRI

                                        >gpIII (C-terminal part)
                                        C TGCCTCAACC TCCTGTCAAT

   436 GCTGGCGGCG GCTCTGGTGG TGGTTCTGGT GGCGGCTCTG AGGGTGGCGG

   476 CTCTGAGGGT GGCGGTTCTG AGGGTGGCGG CTCTGAGGGT GGCGGTTCCG

   526 GTGGCGGCTC CGGTTCCGGT GATTTTGATT ATGAAAAAAT GGCAAACGCT

   576 AATAAGGGGG CTATGACCGA AAATGCCGAT GAAAACGCGC TACAGTCTGA

   626 CGCTAAAGGC AAACTTGATT CTGTCGCTAC TGATTACGGT GCTGCTATCG

   676 ATGGTTTCAT TGGTGACGTT TCCGGCCTTG CTAATGGTAA TGGTGCTACT

   726 GGTGATTTTG CTGGCTCTAA TTCCCAAATG GCTCAAGTCG GTGACGGTGA

   776 TAATTCACCT TTAATGAATA ATTTCCGTCA ATATTTACCT TCTTTGCCTC

   826 AGTCGGTTGA ATGTCGCCCT TATGTCTTTG GCGCTGGTAA ACCATATGAA

   876 TTTTCTATTG ATTGTGACAA AATAAACTTA TTCCGTGGTG TCTTTGCGTT

   926 TCTTTTATAT GTTGCCACCT TTATGTATGT ATTTTCGACG TTTGCTAACA
                        gpIII end>
   976 TACTGCGTAA TAAGGAGTCT TAAGGATCC
                                BamHI
```

Fig. 2a

```
>-gpIV
                                        .
                                     TAATA TTGTTCTGGA TATTACCAGC

1030  AAGGCCGATA GTTTGAGTTC TTCTACTCAG GCAAGTGATG TTATTACTAA

1080  TCAAAGAAGT ATTGCGACAA CGGTTAATTT GCGTGATGGA CAGACTCTTT

1130  TACTCGGTGG CCTCACTGAT TATAAAAACA CTTCTCAGGA TTCTGGCGTA

1180  CCGTTCCTGT CTAAAATCCC TTTAATCGGC CTCCTGTTTA GCTCCCGCTC

1230  TGATTCTAAC GAGGAAAGCA CGTTATACGT GCTCGTCAAA GCAACCATAG
         end gpIV stop  >f1-ori
1280  TACGCGCCCT GTAGCGGCGC ATTAAGCGCG GCGGGTGTGG TGGTTACGCG

1330  CAGCGTGACC GCTACACTTG CCAGCGCCCT AGCGCCCGCT CCTTTCGCTT

1380  TCTTCCCTTC CTTTCTCGCC ACGTTCGCCG GCTTTCCCCG TCAAGCTCTA

1430  AATCGGGGGC TCCCTTTAGG GTTCCGATTT AGTGCTTTAC GGCACCTCGA

1480  CCCCAAAAAA CTTGATTAGG GTGATGGTTC ACGTAGTGGG CCATCGCCCT

1530  GATAGACGGT TTTTCGCCCT TTGACGTTGG AGTCCACGTT CTTTAATAGT

1580  GGACTCTTGT TCCAAACTGG AACAACACTC AACCCTATCT CGGTCTATTC

1630  TTTTGATTTA TAAGGGATTT TGCCGATTTC GGCCTATTGG TTAAAAAATG

1680  AGCTGATTTA ACAAAAATTT AACGCGAATT TTAACAAAAT ATTAACGTTT

1730  ACAATTTAAA TATTTGCTTA TACAATCTTC CTGTTTTTGG GGCTTTTCTG
                 <f1-ORI<
1780  ATTATCAACC GGGGTACAT
                         gpII start
                         A TGATTGACAT GCTAGTTTTA CGATTACCGT

1830  TCATCGCAGG TGGCACTTTT CGGGGAAATG TGCGCGGAAC CCCTATTTGT

1880  TTATTTTTCT AAATACATTC AAATATGTAT CCGCTCATGA GACAATAACC

1930  CTGATAAATG CTTCAATAAT ATTGAAAAAG GAAGAGTATG AGTATTCAAC

1980  ATTTCCGTGT CGCCCTTATT CCCTTTTTTG CGGCATTTTG CCTTCCTGTT

2030  TTTGCT
            >beta-lactamase>
            CACC CAGAAACGCT GGTGAAAGTA AAAGATGCTG AAGATCAGTT

2080  GGGTGCACGA GTGGGTTACA TCGAACTGGA TCTCAACAGC GGTAAGATCC

2130  TTGAGAGTTT TCGCCCCGAA GAACGTTTTC CAATGATGAG CACTTTTAAA

2180  GTTCTGCTAT GTGGCGCGGT ATTATCCCGT ATTGACGCCG GGCAAGAGCA

2230  ACTCGGTCGC CGCATACACT ATTCTCAGAA TGACTTGGTT GAGTACTCAC

2280  CAGTCACAGA AAAGCATCTT ACGGATGGCA TGACAGTAAG AGAATTATGC

2330  AGTGCTGCCA TAACCATGAG TGATAACACT GCGGCCAACT TACTTCTGAC
```

Fig. 2b

```
2380  AACGATCGGA GGACCGAAGG AGCTAACCGC TTTTTTGCAC AACATGGGGG

2430  ATCATGTAAC TCGCCTTGAT CGTTGGGAAC CGGAGCTGAA TGAAGCCATA

2480  CCAAACGACG AGCGTGACAC CACGATGCCT GTAGCAATGG CAACAACGTT

2530  GCGCAAACTA TTAACTGGCG AACTACTTAC TCTAGCTTCC CGGCAACAAT

2580  TAATAGACTG GATGGAGGCG GATAAAGTTG CAGGACCACT TCTGCGCTCG

2630  GCCCTTCCGG CTGGCTGGTT TATTGCTGAT AAATCTGGAG CCGGTGAGCG

2680  TGGGTCTCGC GGTATCATTG CAGCACTGGG GCCAGATGGT AAGCCCTCCC

2730  GTATCGTAGT TATCTACACG ACGGGGAGTC AGGCAACTAT GGATGAACGA

2780  AATAGACAGA TCGCTGAGAT AGGTGCCTCA CTGATTAAGC ATTGG
                                   <beta-lactamase<
                                                        TAACT

2830  GTCAGACCAA GTTTACTCAT ATATACTTTA GATTGATTTA AAACTTCATT

2880  TTTAATTTA
                <colE1-ori<
                A AAGGATCTAG GTGAAGATCC TTTTTGATAA TCTCATGACC

2930  AAAATCCCTT AACGTGAGTT TTCGTTCCAC TGAGCGTCAG ACCCCGTAGA

2980  AAAGATCAAA GGATCTTCTT GAGATCCTTT TTTTCTGCGC GTAATCTGCT

3030  GCTTGCAAAC AAAAAAACCA CCGCTACCAG CGGTGGTTTG TTTGCCGGAT

3080  CAAGAGCTAC CAACTCTTTT TCCGAAGGTA ACTGGCTTCA GCAGAGCGCA

3130  GATACCAAAT ACTGTCCTTC TAGTGTAGCC GTAGTTAGGC CACCACTTCA

3180  AGAACTCTGT AGCACCGCCT ACATACCTCG CTCTGCTAAT CCTGTTACCA

3230  GTGGCTGCTG CCAGTGGCGA TAAGTCGTGT CTTACCGGGT TGGACTCAAG

3280  ACGATAGTTA CCGGATAAGG CGCAGCGGTC GGGCTGAACG GGGGGTTCGT

3330  GCACACAGCC CAGCTTGGAG CGAACGACCT ACACCGAACT GAGATACCTA

3380  CAGCGTGAGC TATGAGAAAG CGCCACGCTT CCCGAAGGGA GAAAGGCGGA

3430  CAGGTATCCG GTAAGCGGCA GGGTCGGAAC AGGAGAGCGC ACGAGGGAGC

3480  TTCCAGGGGG AAACGCCTGG TATCTTTATA GTCCTGTCGG GTTTCGCCAC

3530  CTCTGACTTG AGCGTCGATT TTTGTGATGC TCGTCAGGGG GGCGGAGCCT

3580  ATG
         <ColE1-ori<
         GAAAAAC GCCAGCAACG CGGCCTTTTT ACGGTTCCTG GCCTTTTGCT

3630  GGCCTTTTGC TCACATGTTC TTTCCTGCGT TATCCCCTGA TTCTGTGGAT

3680  AACCGTATTA CCGCCTTTGA GTGAGCTGAT ACCGCTCGCC GCAGCCGAAC

3730  GACCGAGCGC AGCGAGTCAG TGAGCGAGGA AGCGGAAGAG C
```

Fig. 2c

B92 heavy chain

| VH | number of clones | CDR1 | CDR2 | CDR3 |
|---|---|---|---|---|
| B92-A | 8 | SNSAAWS | TRYYRSKWYNDYALSVKS | WKAFTAVAGPNYYYGMDV |
| B92-B1 | 5 | SYYWS | RIYASGRPKYNPSLKS | VYSSSLTDFDYYYGLDV |
| B92-B2 | 1 | ----- | ---------- | -C---------- |
| B92-C1 | 2 | GSSNYWG | SIHYIGTTYYNPSFKS | RTRWCWFDP |
| B92-C2 | 1 | ------- | -T---------- | --------- |

B93 heavy chain

| VH | number of clones | CDR1 | CDR2 | CDR3 |
|---|---|---|---|---|
| B93-A1 | 5 | NYSLN | AISSSGTYRFYADSLRG | DLGDLEWLHSPDP |
| B93-A2 | 1 | ---F- | ---R---------- | -----D------- |
| B93-B1 | 5 | SYWID | IIYPDDSDTRYSPSFQG | RGDSGTLWGD |
| B93-B2 | 1 | N---- | ---------- | ---------- |
| B93-C | 1 | SYAMN | SISGSGIGTYYANSVQG | DELNQLPGYYFDY |

Fig. 15

| average | HFF | MCF10-2A | MCF7 | MDA-MB468 |
|---|---|---|---|---|
| mix 7 | 0.119 | 0.192 | 0.490 | 0.383 |
| mix 8 | 0.462 | 0.548 | 2.241 | 1.149 |
| mix 11 | 0.254 | 0.350 | 0.424 | 0.507 |
| mix 12 | 0.282 | 0.291 | 0.673 | 0.414 |
| mix 17 | 0.118 | 0.179 | 0.606 | 0.435 |
| mix 23 | 0.157 | 0.223 | 0.585 | 0.393 |
| mix 25 | 0.236 | 0.318 | 0.622 | 0.382 |
| mix 39 | 0.168 | 0.237 | 1.527 | 0.497 |
| B96/4F | 0.222 | 1.711 | 0.497 | 0.376 |
| B96/11L | 0.142 | 0.206 | 1.148 | 0.501 |
| αSP2 | 0.110 | 0.192 | 0.149 | 0.183 |

VECTOR FOR EFFICIENT SELECTION AND/OR MATURATION OF AN ANTIBODY AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

*Two reissue applications have been filed for the reissue of U.S. Pat. No. 8,003,383: this application and a reissue continuation application, U.S. application Ser. No. 14/998,264 filed on Dec. 23, 2015.* This application is *a reissue of U.S. Pat. No. 8,003,383, which was filed as U.S. application Ser. No. 12/097,876 on Jun. 17, 2008, which, in turn, is* the national phase of International Application PCT/IT2006/000876 filed on Dec. 27, 2006 which, in turn, claims priority to European Patent Application 05028501.4 filed on Dec. 27, 2005.

The present invention relates to a method of improving the antibody selection capacity in phage-display library, in which said improvement is obtained through the reduction of the expression levels of the antibodies produced in said library.

FIELD OF THE INVENTION

Recombinant DNA technology provides a cheap and useful alternative to monoclonal antibody production. Display of recombinant antibodies on bacteriophage capsid, known as phage-display, not only allows generation of human antibody libraries for selection of specific binders, providing antibodies useful for therapy not inducing a harmful immune response in patients, but also facilitates affinity maturation of antibodies through construction of mutant antibody libraries, giving clones with a higher affinity.

The possibility of finding high-affinity binders in a recombinant antibody library characterizes its quality, which depends on several factors like library size, diversity and source of immunoglobulin genes.

It is known that various lymphoid tissues from immunized or non-immunized donors, such as peripheral blood lymphocytes, spleen and bone marrow and even metastasized or drained lymph node tissue from individuals affected by tumors may serve as a source of specific antibody repertoire.

Although naïve antibody libraries are more diverse and lead to isolation of broad antibody specificities, it is reasonable to suggest that construction of a recombinant antibody library from Ig repertoire of a patient affected by specific disease can provide antibody fragments of higher binding affinity against particular antigens.

Several published studies describe construction of recombinant antibody libraries from tumor-associated lymph nodes (Clin. Exp. Immunol. 1997 109(1):166-74; Int. J. Mol. Med. 2004 14(4):729-35; World J. Gastroenterol. 2004 10(18):2619-23). These studies are based on the general idea that lymph node tissue from cancer patients are infiltrated with activated B cells, which may serve as source of tumor-specific antibodies.

It is quite difficult to obtain metastasized or drained lymph nodes from breast cancer patients as fresh surgical material. According to recent medical practice the surgeon removes only a sentinel lymph node or a small cluster of nodes (sentinel node and those closest to it), thus performing less invasive surgery and reducing side effects, instead of removing dozen of lymph nodes according to previous surgery technique. After sentinel lymph node dissection, practically the entire node is studied for presence of micrometastasis or single cancer cells. Therefore, in breast cancer surgery the metastasized node is practically unavailable as discarded surgical material.

The evidence that tumor-infiltrating B lymphocyte (TIL-B)-derived antibodies may also recognize tumor cells was obtained by producing human hybridomas, obtained from TIL, able to secrete tumor-specific antibodies (Lancet. 1982 1(8262):11-4; Br. J. Cancer, 1983 47(1):135-45); by B cell expansion of TIL from human tumor biopsies (Cancer Immunol. Immunother. 1994 38(4):225-32), by B cell expansion of melanoma-derived TIL and following cloning the scFv antibody from single B cell clone with specific melanoma reactivity (Cancer Res. 1995 55:3584-91); and by subcutaneous transplantation of human lung cancer tissue in immunodeficient mice producing human antibodies derived from TIL-B, which recognized two tumor-specific proteins (Cancer Invest. 2000; 18(6):530-6; Cancer Res. 2002 62(6):1751-6), thus suggesting a specific function of TIL-B in the tumor.

Recently, cervical carcinoma and a rare type of breast cancer, classified as medullary carcinoma (MCB) have been shown to be characterized by lymphoplasmacytic infiltrates that correlate with improved prognosis and patient survival. These diseases, were investigated to understand the nature of tumor-infiltrated B lymphocytes (TIL-B) by using also phage-display methods. Study of the molecular structure of variable antibody regions gave evidence of antigen-driven humoral immune responses in medullary breast carcinomas, as well as in cervical tumors. Oligoclonal predominance found in antibody genes derived from TIL indicated possible clonal selection of the Ig molecules against specific neoantigens overexpressed, or specifically expressed, in tumor tissue (Cancer Immunol. Immunother. 2001 50(10):523-32; Cancer Res. 2001 61(21):7889-99; Proc. Natl. Acad. Sci. U.S.A. 2001 98(22):12659-64; J. Immunol. 2002 169(5):2701-11).

Despite the very strong above-mentioned indications that tumor tissue is infiltrated with activated B cells, which may serve as a source of tumor-specific antibodies, several research groups, in the panning experiments performed with TIL-derived phage-display libraries against purified known tumor antigens, or living tumor cells, or frozen tissue sections, failed to select either a specific antibody discriminating between tumor and normal cells, or one reactive with cell-surface tumor antigens (Cancer Res. 2001 61(21):7889-99; Proc. Natl. Acad. Sci. U.S.A. 2001 98(22):12659-64; Int. J. Cancer 2001 93:832-40). Only later, two different groups managed to identify specific antibodies recognizing tumor cells from this kind of phage-display libraries (J. Immunol. 2002 169:1829-36; J Immunol. 2005 175(4):2278-85).

An alternative approach, based on a phage-expression tumor-derived library and direct plaque screening protocols, that avoided limitations of phage display system, allowed Wu and colleagues (Cancer Immunol Immunother. 2002 51(2):79-90) to isolate multiple antibodies that specifically bound cultured tumor cells. This study indicates that the observed difficulties in selection of anti-tumor antibodies from TIL-derived phage-display libraries result from imperfection of display vectors known in the art. However, the direct screening is also not an excellent method for selection of recombinant antibodies from large libraries. Indeed it is a laborious procedure demanding large expenses of time and means, as compared to the phage display technology.

Applicant performed a screening of recombinant antibody phage-display libraries derived from TIL-B by utilizing novel phagemid vector pKM19 and demonstrated efficient selection of tumor-specific antibodies against desirable tumor antigens as well as against living breast carcinoma cells.

SUMMARY OF INVENTION

The authors have found that it is possible to improve the efficiency of selection and/or maturation of recombinant antibodies from libraries by using the phage-display system, upon suitable modifications of prior art vectors. Prior art vectors are, i.e., phagemid vectors as in "Antibody Engineering—A practical approach (McCafferty, J. Hoogenboom, H. & Chiswell D., eds), pp. 325, Oxford University Press, 1996)".

Therefore it is an object of the instant invention a vector, suitable for efficient selection and/or maturation of a recombinant antibody, characterized in that it contains at least one element able to reduce the expression level and/or has an improved efficiency of display of said recombinant antibody.

In the instant invention a recombinant antibody includes: ScFv, active fragments of Abs, or any other derivatives of Abs known in the art, including humanized sequences of Abs.

The vector of the invention may be a plasmid, a phagemid, a phage, or any other vectors known to the skilled in the art.

In one preferred aspect the element able to reduce the expression level of the recombinant antibody belongs to the group of: a) a suppressed stop codon inside either the leader peptide or the antibody coding sequence; b) a low-efficient promoter driving transcription of said antibody coding sequence; c) an inhibitor of the promoter driving transcription of said antibody coding sequence.

Low-efficient promoters are known in the art and are exemplified in Biochem J. 1970 117: 741-746). Suitable inhibitors for promoters are known in the art and are exemplified in J. Bacteriol. 1979, 138(1):40-7.

In one preferred aspect the improved efficiency of display of said recombinant antibody is obtained by: a) fusing the recombinant, antibody coding sequence to a sequence coding for the carboxy-terminal part of the pIII protein; and/or b) using as leader peptide of the recombinant antibody the leader peptide of the alkaline phosphatase of E. coli; and/or c) eliminating any amber codon between the recombinant antibody coding sequence and the pIII coding sequence.

It is a further object of the present invention a phagemid vector having the nucleotide sequence of SEQ ID NO: 1.

This vector, named pKM19, is designed for the display of recombinant antibodies in single-chain format on the surface of filamentous phage.

It is a further object of the invention a phage display-antibody library obtained by cloning cDNAs into the vector of the invention. Preferably the library is obtained by cloning in the vector of the invention cDNAs from antibody producing cells, more preferably Tumor Infiltrating Lymphocytes (TILs) or Peripheral Blood Lymphocytes (PBLs). In a preferred aspect such antibody producing cells are isolated from a tumor affected subject, preferably from a breast cancer affected subject. Alternatively the library consists of synthetic or semi-synthetic antibody libraries, also mutated for affinity maturation of antibodies.

It is within the scope of the invention an antibody selected from the library of the invention, and method for selecting the same, able to recognize an antigen or a complex multi-component biological structure, preferably a cell or a cell membrane, more preferably selected from the group comprising: MUC1 tumor antigen, CEA (carcino-embrionic antigen), MCF7 breast carcinoma cells. Said antibodies may be in single or double-format.

In a particular aspect the MUC1 tumor antigen antibody is the MB5 scFv antibody consisting essentially of the amino acid sequence of SEQ ID NO: 3, preferably coded by the nucleotide sequence of SEQ ID NO: 2. Alternatively the MUC1 tumor antigen antibody is the MB5/C'1 scFv antibody, consisting essentially of the amino acid sequence of SEQ ID NO: 5, preferably coded by the nucleotide sequence of SEQ ID NO: 4. Alternatively the MUC1 tumor antigen antibody is the MB5/C'3 scFv antibody, consisting essentially of the amino acid sequence of SEQ ID NO: 7, preferably coded by the nucleotide sequence of SEQ ID NO: 6.

In a particular aspect the CEA tumor antigen antibody is the CB37 scFv antibody consisting essentially of the amino acid sequence of SEQ ID NO: 9, preferably coded by the nucleotide sequence of SEQ ID NO: 8. Alternatively the CEA tumor antigen antibody is the CB37/9C scFv antibody, consisting essentially of the amino acid sequence of SEQ ID NO:13, preferably coded by the nucleotide sequence of SEQ ID NO:12. Alternatively the MUC1 tumor antigen antibody is the CB37/3B scFv antibody, consisting essentially of the amino acid sequence of SEQ ID NO:11, preferably coded by the nucleotide sequence of SEQ ID NO:10.

In a particular aspect the MCF7 breast carcinoma cells antibody is the B96/11L scFv antibody consisting essentially of the amino acid sequence of SEQ ID NO: 15, preferably coded by the nucleotide sequence of SEQ ID NO: 14. Alternatively the MCF7 breast carcinoma cells antibody is the mix7 scFv antibody, consisting essentially of the amino acid sequence of SEQ ID NO: 17, preferably coded by the nucleotide sequence of SEQ ID NO: 16. Alternatively the MCF7 breast carcinoma cells antibody is the mix17 scFv antibody, consisting essentially of the amino acid sequence of SEQ ID NO: 19, preferably coded by the nucleotide sequence of SEQ ID NO: 18. Alternatively the MCF7 breast carcinoma cells antibody is the mix39 scFv antibody, consisting essentially of the amino acid sequence of SEQ ID NO: 21, preferably coded by the nucleotide sequence of SEQ ID NO: 20.

The antibodies selected from the libraries of the invention may be advantageously utilized for therapeutic, diagnostic, immunogenic or research purposes. Conveniently they may be utilized for preparing suitable pharmaceutical compositions comprising as active ingredient one or more recombinant antibody of the invention and optionally one or more excipients or diluents pharmaceutically acceptable and known in the art.

The antibodies of the invention may be also utilized for obtaining so-called maturation libraries wherein single Variable Heavy chains (VH) coding sequences are co-transfected with Variable Light chain (VL) coding sequences, and recombinant antibodies selected for affinity.

Moreover the antibodies may be utilized for selecting recombinant and/or synthetic peptides able to mimic the native antigen. Tumor surface antigens can be selected by using novel anti-tumor antibodies recognizing tumor cells through: (i) immunoprecipitation of unknown target proteins from tumor cell extracts (Antibodies. A laboratory manual. Ed Harlow, David Lane, Cold Spring Harbor, N.Y.: Cold Spring Harbor Laboratory Press, 1988); or (ii) developing the immunoreactions with tumor cell extract, separated by two-dimensional PAGE (Proteins and proteomics: A laboratory manual. Richard J. Simpson, pp. 705, Science 2002) and transferred onto nitrocellulose membrane (Sambrook J, Fritsch E F, Maniatis T. Molecular cloning: A laboratory manual. Cold Spring Harbor Laboratory Press, Cold Spring Harbor, 1989);

Such recombinant and/or synthetic peptides able to mimic the native antigen so obtained may be utilized for producing vaccines, diagnostic reagents or in the research field. Conveniently they may be utilized for preparing suitable pharmaceutical compositions comprising as active ingredient one or more disease-specific antigen above mentioned, and optionally one or more excipients or diluents pharmaceutically acceptable and known in the art.

It is a further object of the present invention a nucleic acid encoding for the recombinant antibody obtained by the library of the invention.

Preferably the nucleic acid encodes for a MUC1 tumor antigen antibody, more it has the nucleotide sequence of SEQ ID NO: 2. Alternatively it has the nucleotide sequence of SEQ ID NO: 4. Alternatively it has the nucleotide sequence of SEQ ID NO: 6.

Preferably the nucleic acid encodes for a CEA tumor antigen antibody, more preferably it has the nucleotide sequence of SEQ ID NO: 8. Alternatively it has the nucleotide sequence of SEQ ID NO: 10. Alternatively it has the nucleotide sequence of SEQ ID NO: 12.

Preferably the nucleic acid encodes for a MCF7 breast carcinoma cells antibody, more preferably it has the nucleotide sequence of SEQ ID NO: 14. Alternatively it has the nucleotide sequence of SEQ ID NO: 16. Alternatively it has the nucleotide sequence of SEQ ID NO: 18. Alternatively it has the nucleotide sequence of SEQ ID NO: 20.

It is a further object of the present invention a host cell transformed with the vector of the invention able to express the antibody.

It is another object of the invention a method for improving the selection and/or maturation of a recombinant antibody comprising the step of using as cloning and expression vector the vector of the invention as above described.

The invention will be now described by means of non limiting examples referring to the following figures:

DETAILED DESCRIPTION OF THE DRAWINGS

FIG. 1. It is schematically described the essential elements of pKM16 plasmid useful for the production of soluble antibodies in scFv format and the essential elements of pKM17, pKM18 and pKM19 plasmids useful for production of phage-displayed antibodies. These plasmids direct antibody expression under control of pLac promoter. The unique NcoI and NotI cloning sites allow insertion of an antibody gene to express single-chain antibodies with a leader peptide of the bacterial periplasmic enzyme, alkaline phosphatase (PhoA leader). Plasmid pKM17 encodes the entire protein pIII (406 aa) and plasmids pKM18 and pKM19 encode the carboxy-terminal part of pIII (197 aa). Plasmid pKM19 contains amber codon in PhoA leader.

FIGS. 2a, 2b, 2c. It is described the detailed structure of pKM19 phagemid vector (SEQ ID NO: 1). The specific modification made are reported in the figure and described in the text.

Figure 3:
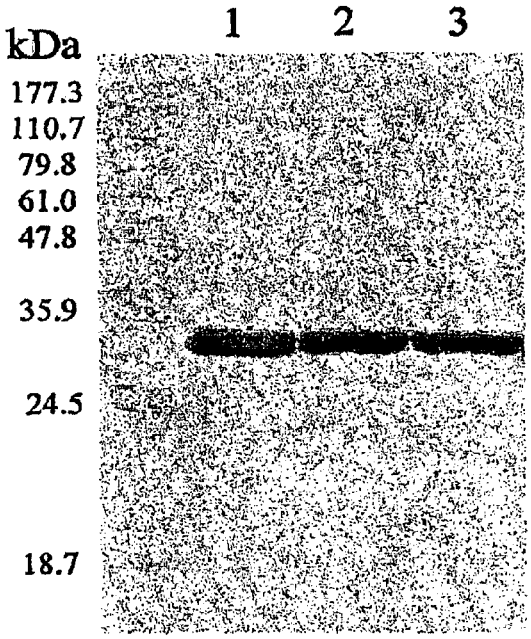

FIG. 3. Soluble scFv production by using pKM16 plasmid. Three independent clones obtained by cloning scFv anticarcino-embryonic antigen (CEA) gene in pKM16 were tested for soluble scFv production (gel lines 1-3). Periplasmic protein fractions were purified from bacteria by freeze and thaw method. The protein size marker is included. Western blot membrane was developed with an anti-FLAG AP-conjugated secondary antibody. Bands corresponding to soluble scFv antibodies (expected molecular weight 26 kDa) migrate between 24.5 and 35.9 kDa bands.

Figure 4:
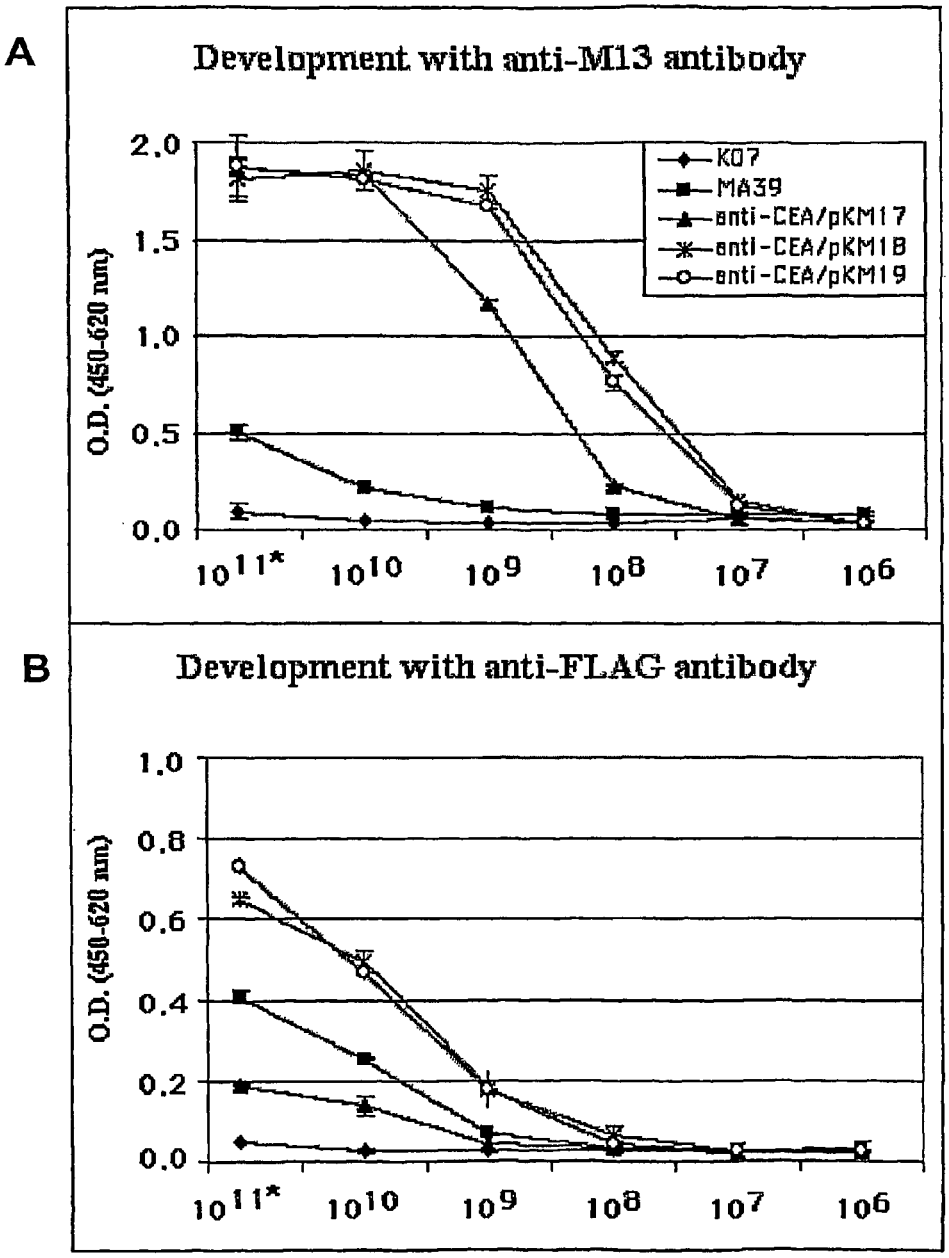

FIG. 4. Display efficiency of pKM17, pKM18 and pKM19 plasmids in comparison with a classic phagemid system. Anti-CEA scFv antibodies displayed by the three different plasmids, were assayed by ELISA against CEA protein and compared with MA39 phage (anti-CEA/pDN322). The helper phage, M13K07, that does not display antibody fragments, was included as negative control. Data reported are the average values of assays performed in duplicate. The highest phage concentration, labeled by asterisk, corresponds to the $10^{11}$ TU for all phages and $3\times10^{10}$ TU for anti-CEA/pKM17. The ELISA was performed by using the anti-M13 (panel A), or alternatively, the anti-FLAG secondary antibody (panel B).

Figure 5:
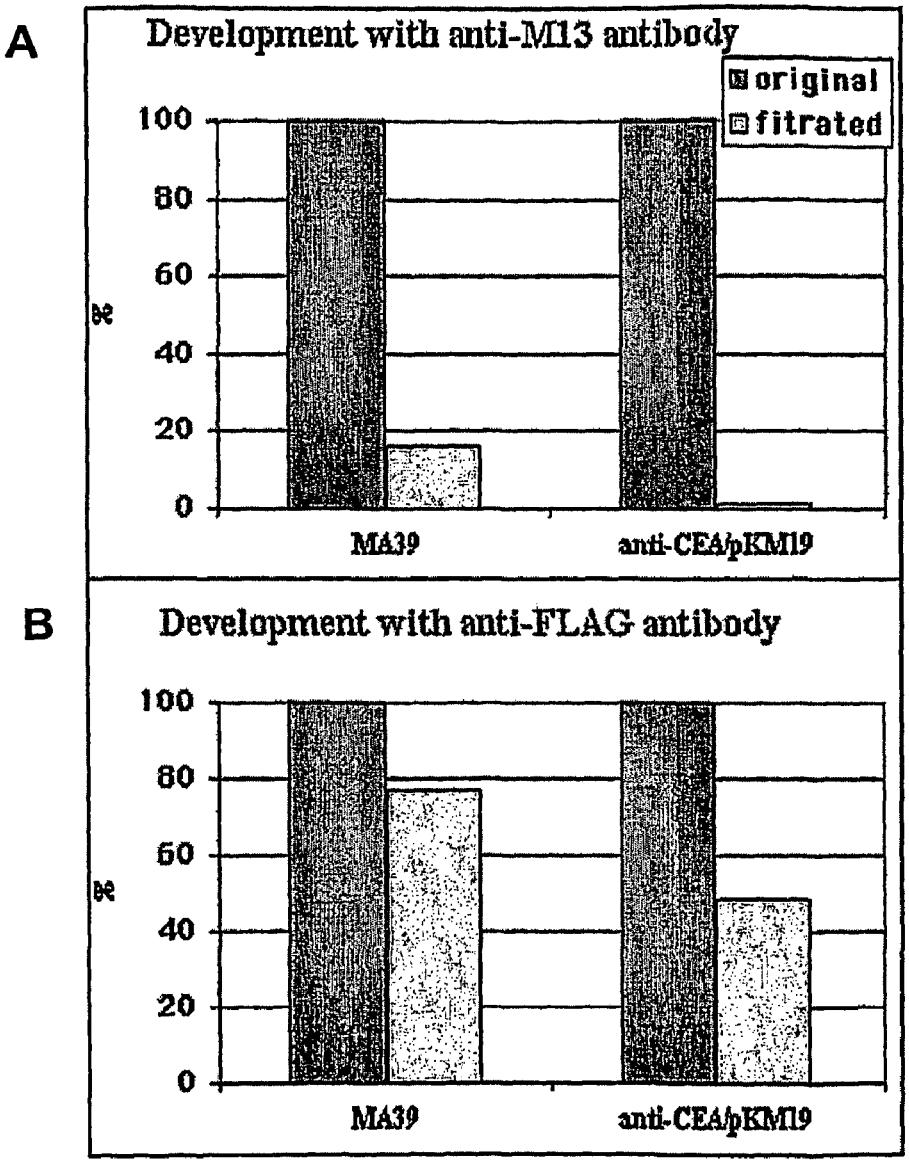

FIG. 5. Filtration of phage samples. About $2\times10^{11}$ TU/well of each preparation or the corresponding quantity of filtrate samples were tested in ELISA and developed either with anti-M13 (panel A) or anti-FLAG (panel B) secondary antibodies. Data reported are the average values of assays performed in duplicate. The data show reactivity of filtrates against CEA as percentage of original reactivity of non-filtrated samples (100%).

Figure 6:
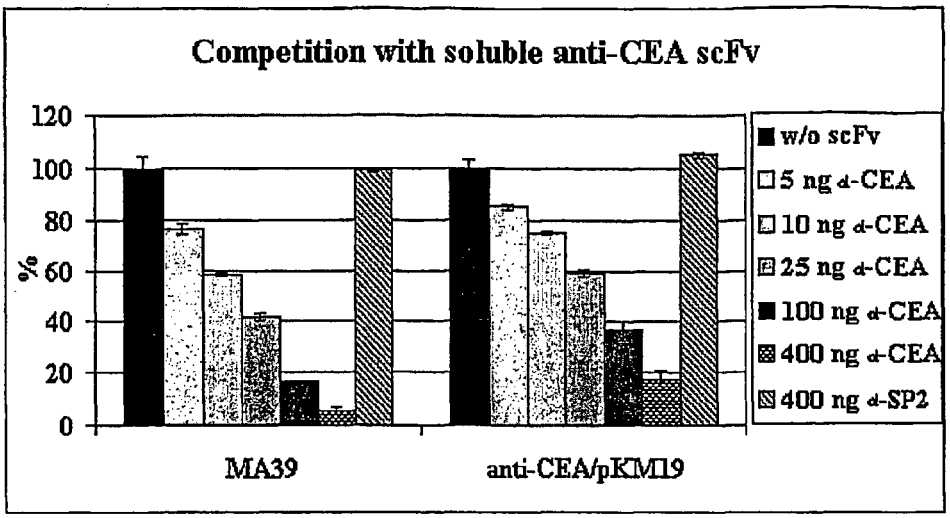

FIG. 6. Competition with soluble anti-CEA scFv. Freshly prepared supernatants of MA39 (10 μL) and anti-CEA/pKM19 (5 μL) phages competed with various amounts of the purified soluble anti-CEA antibody. The data are expressed as percentage of reactivity of the supernatants without competitors. The irrelevant soluble anti-SP2 scFv was used as negative control.

Figure 7:
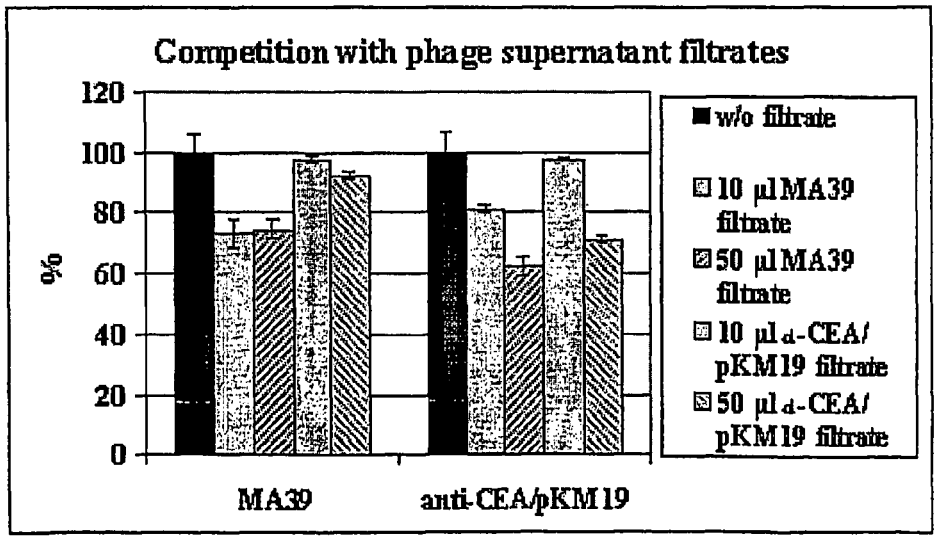

FIG. 7. Competition with phage supernatant filtrates. Freshly prepared supernatants of MA39 (10 μL) and anti-CEA/pKM19 (5 μL) phages were competed with 10 μL or 50 μL of filtrates of the same phage supernatants. The data are expressed as percentage of reactivity of the supernatants without competitors.

Figure 8:
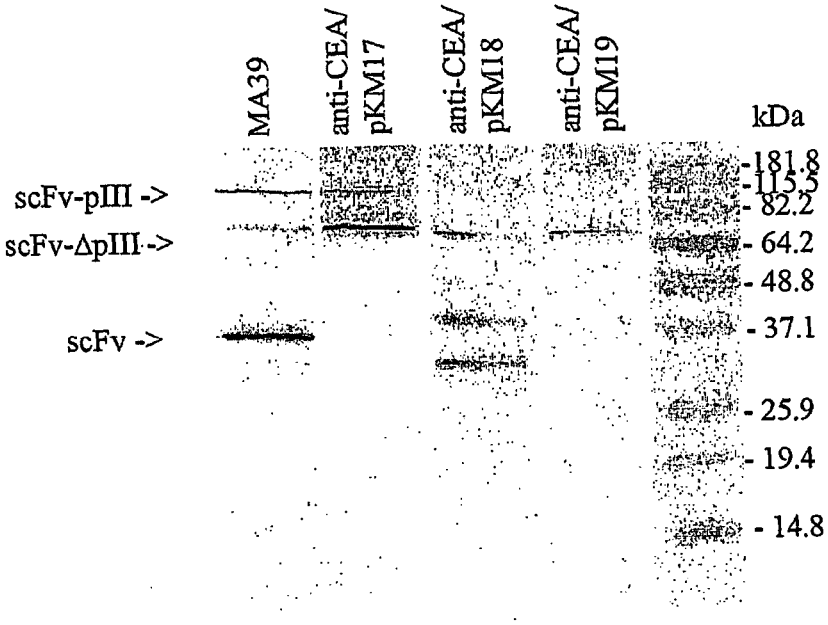

FIG. 8. Western blot of PEG-purified recombinant phages. Protein extracts from about $5\times10^9$ PFU of phages MA39, anti-CEA/pKM18 and anti-CEA/pKM19, and $1\times10^9$ PFU of anti-CEA/pKM17 were fractionated by SDS-PAGE and transferred onto a nitrocellulose membrane. The membrane strips were developed with an anti-FLAG AP-conjugated antibody. The protein size marker is included (last strip). The scFv-pIII (66.1 kDa) and scFv-ΔpIII (45.2 kDa) proteins migrate as higher molecular weight bands because of an anomalous moiety of the pIII protein described earlier (Goldsmith and Konigsberg, 1977).

Figure 9:
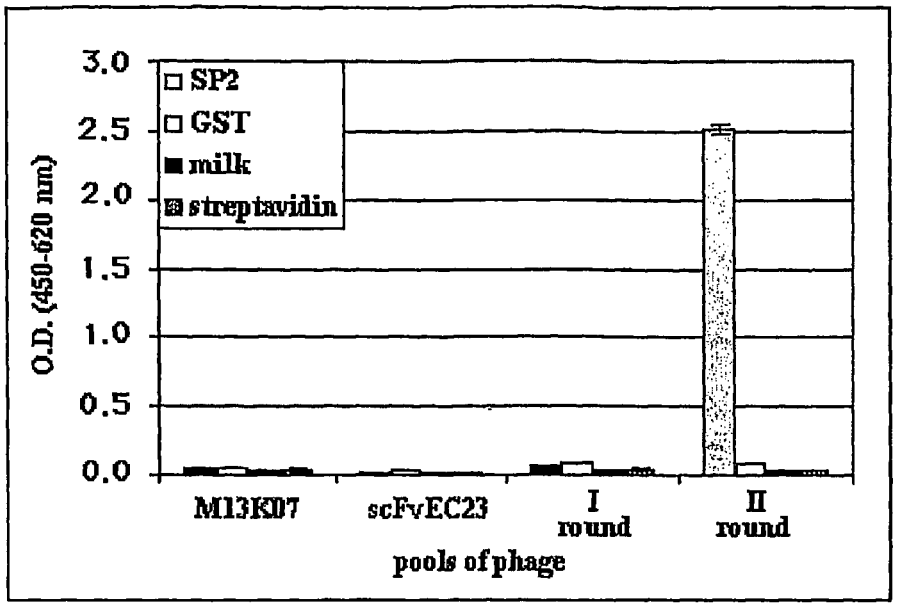

FIG. 9. Selection against SP2-GST protein. Reactivity of the phage pools derived from first and second rounds of panning of the scFvEC23 library is shown. GST (glutathione S-transferase), milk and streptavidin, present in the selection system, are included as negative controls. Data reported are the average values of assays performed in duplicate. Phage input was normalized since $3\times10^9$ TU per single well of each preparation were tested in ELISA.

Figure 10:
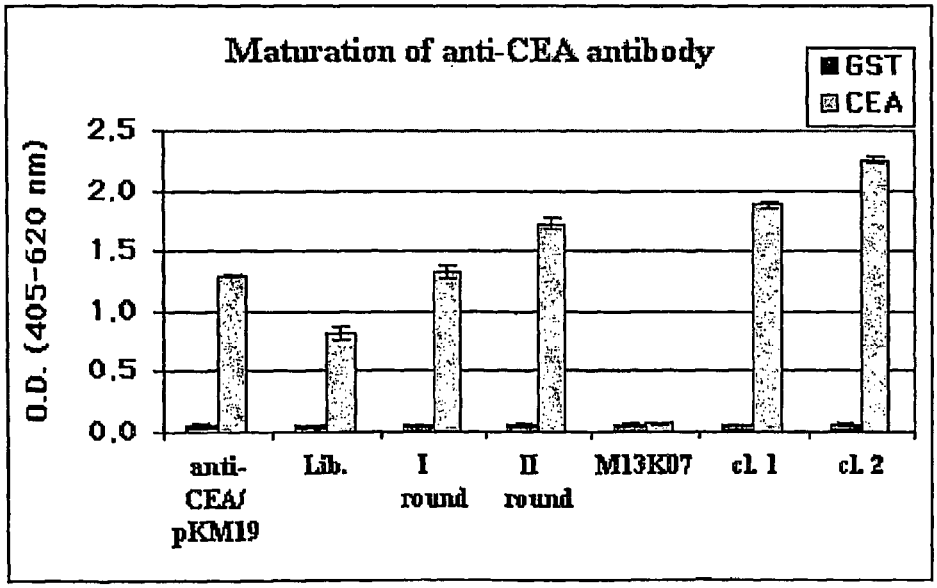

FIG. 10 Affinity selection of maturated anti-CEA gene from a maturation library. In this assay, positive immunoreactions were developed by an anti-FLAG AP-conjugated secondary antibody, in order to moderate positive signals and make visible the increasing reactivity during the selection process. The helper phage, M13K07, that does not display antibody fragments, was included as negative control. The reactivity of the original anti-CEA antibody in pKM19 (anti-CEA/pKM19), maturation library (Lib.), pools of phage after first and second round of selection (I round, II round) and single clones (c1.1, c1.2) from the phage pool after second round of affinity selection, tested on CEA and irrelevant GST protein, are shown. Data reported are the average values of assays performed in duplicate. Phage input was normalized. About $3\times10^{10}$ TU per single well of each preparation were tested in ELISA.

Figure 11:
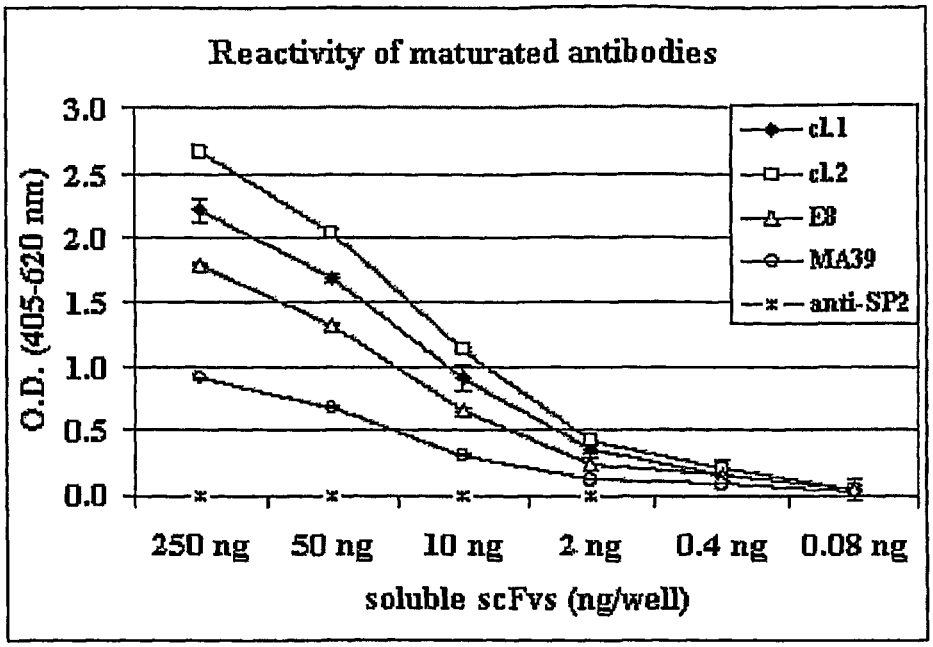

FIG. 11. ELISA reactivity of soluble maturated scFvs. Various amounts of soluble antibodies were assayed on CEA-coated plates. Bound scFvs were developed by using an anti-FLAG secondary antibody. Data reported are the average values of assays performed in duplicate. The irrelevant anti-SP2 antibody and maturated anti-CEA ES antibody, obtained earlier (Pavoni et al., 2006), were included as controls.

Figure 12:
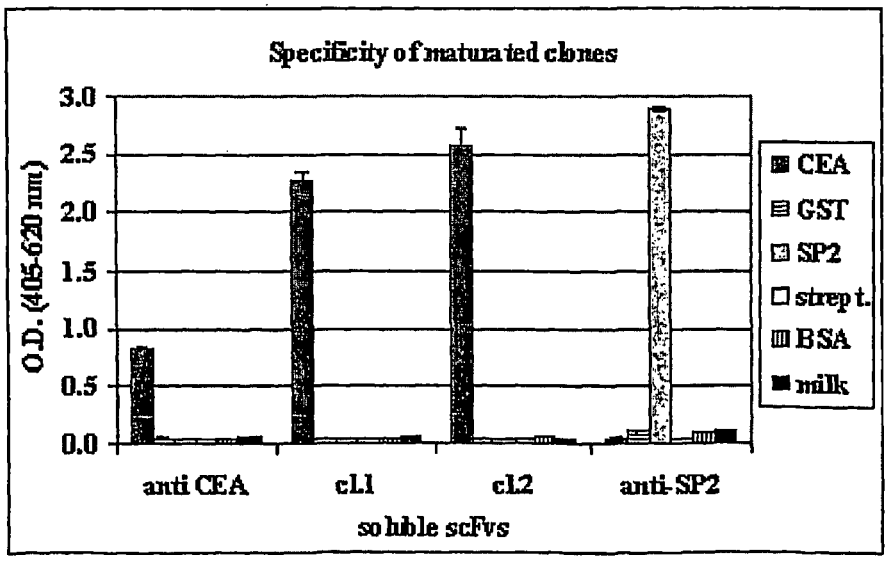

FIG. 12. Specificity of maturated clones. About 250 ng per well of original and maturated antibodies in soluble form were assayed with CEA and various irrelevant proteins. The irrelevant anti-SP2 antibody was included as negative control. Data reported are the average values of assays performed in duplicate.

Figure 13:
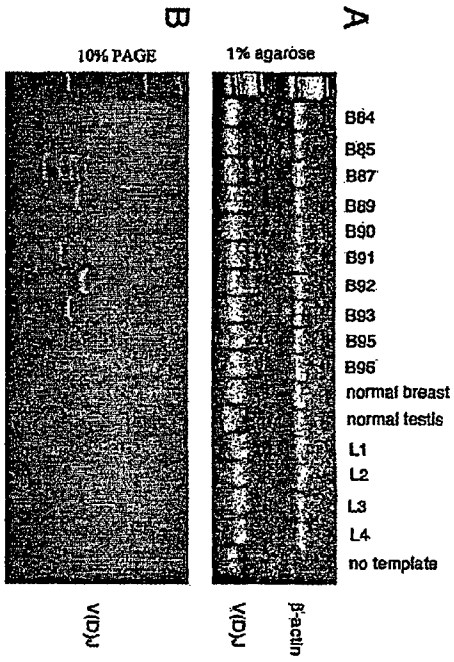

FIG. 13. V(D)J analysis of TIL-derived antibody genes. A. SMART cDNAs derived from 10 different tumor samples (patients B84, B85, B87, B89, B90, B91, B92, B93, B95, B96), from normal breast, normal testis and lymphocytes from four healthy donors (L1, L2, L3, L4), were used, as template for amplification of V(D)J antibody regions. Samples of the cDNAs were normalized by amplification of β-actin housekeeping gene. V(D)J fragments were amplified well from all templates excluding normal testis cDNA. B. The same PCR products were fractionated by PAGE giving a higher resolution for DNA bands.

Figure 14:
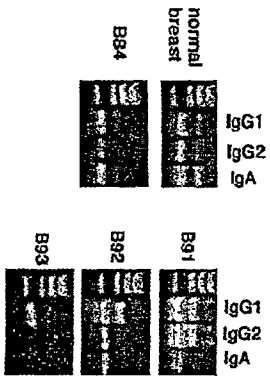

FIG. 14. Antibody subclass distributions. PCR-amplified normal breast and B84 cDNA samples, not showing oligoclonal bands in the V(D)J test, have prevalence of IgA bands in comparison to IgG1 and IgG2 (left panel), while three samples, showing strong oligoclonal bands in previous test (B91, B92 and B93), have IgG1 or both IgG1 and IgG2 bands prevalence in comparison with IgA (right panel).

FIG. 15. Amino acid sequences of variable regions of 30 random clones obtained by cloning γ-chain antibody genes derived from B92 (SEQ ID NO: 54 to SEQ ID NO:64) and B93 (SEQ ID NO: 65 to SEQ ID NO: 77) cDNAs. Peptide sequence is reported in single-letter code. Identical amino acids a in similar clones are represented by a dash.

Figure 16:
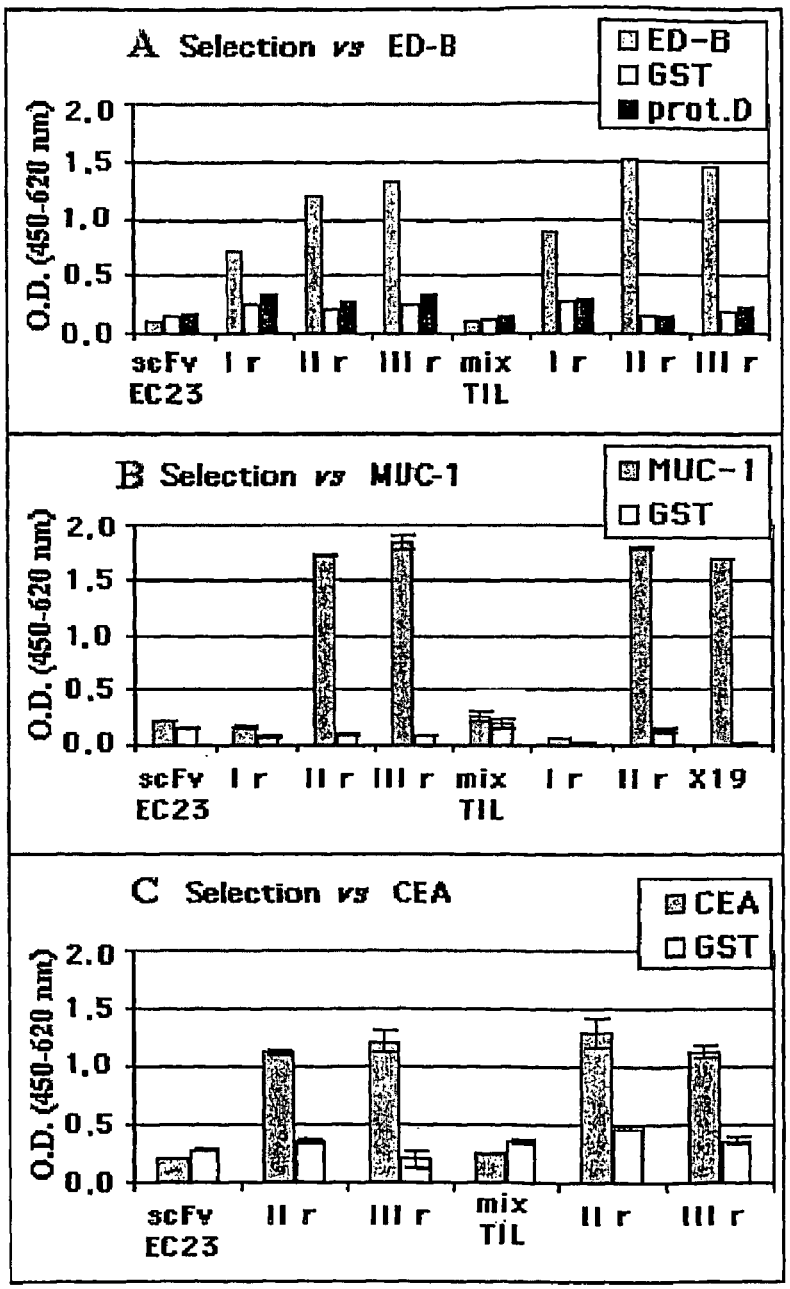

FIG. 16. Selection on ED-B, MUC1 and CEA proteins. Reactivity of phage pools derived from second and third rounds of panning in comparison with original libraries were tested. GST is included as a negative control. Additional negative control, protein D possessing 6His tail as a target protein used in the selection was used in case of ED-B panning. Data reported are the average values of assays performed in duplicate. Library ScFvEC23 derives from PBL. MixTIL is a mixture of 4 TIL-derived libraries (ScFvB87, ScFvB95, ScFvB96 and ScFvmix) as indicated in table 1.

Figure 17:
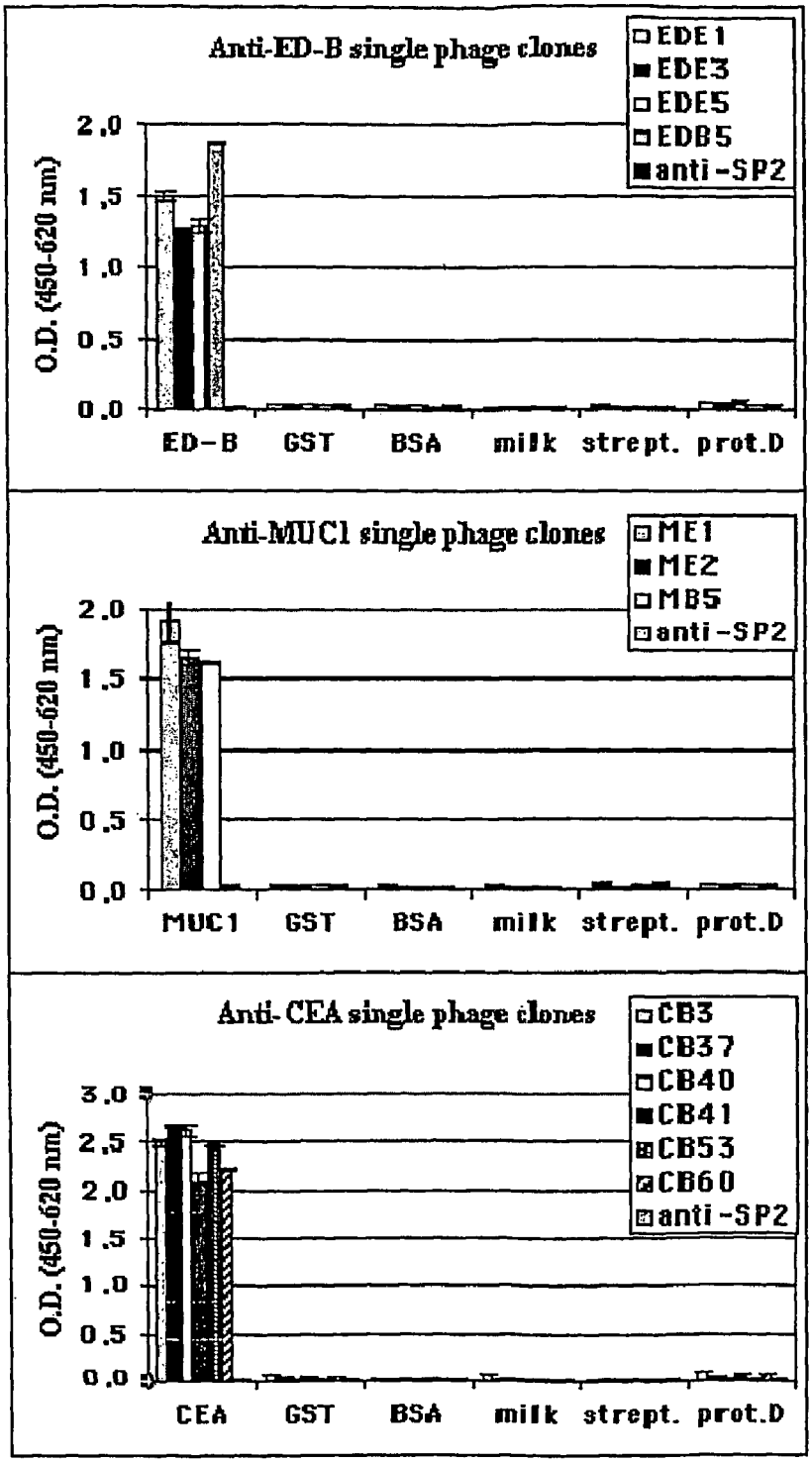

FIG. 17. ELISA reactivity of single phage clones displayed scFv antibodies. Reactivity of single phage clones selected against ED-B (clones EDE1, EDE3, EDE5, EDB5, table 5), MUC1 (clones ME 1, ME2, MB5, table 5) and CEA (clones CB3, CB37, CB40, CB41, CB53, CB60, table 5) after third round of selection was tested using respective proteins. Data reported are the average values of assays performed in duplicate. Several irrelevant proteins and an anti-SP2 irrelevant phage antibody are included as negative controls.

Figures 18, 19:
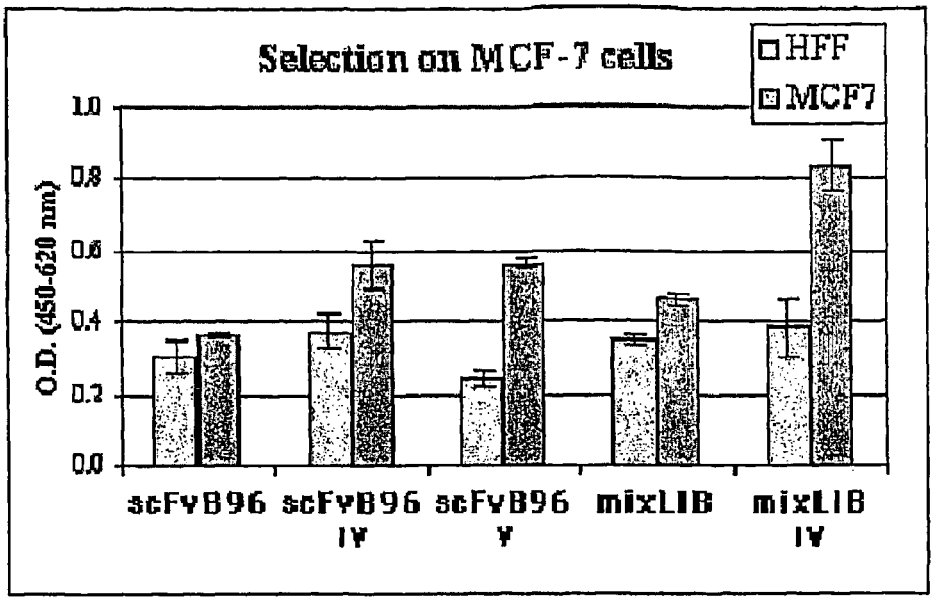

FIG. 18. Cell-based panning reactivity against fixed breast carcinoma (MCF7) and human fibroblast (HFF) cells of phage pools derived from fourth and fifth rounds of panning in comparison with original libraries, were tested. Data reported are the average values of assays performed in triplicate. Libraries scFvB96 and mixLIB are defined in Table 2.

FIG. 19. Cell-ELISA reactivity against fixed cells of single phage clones. Data reported are the average values of assays performed in triplicate. Cell developing with irrelevant anti-SP2 antibody is included as negative control. MCF7 and MDA-MB-468: fixed breast carcinoma cells; HFF: human fibroblast and MCF10-2A: normal breast epithelium cells.

Figure 20:
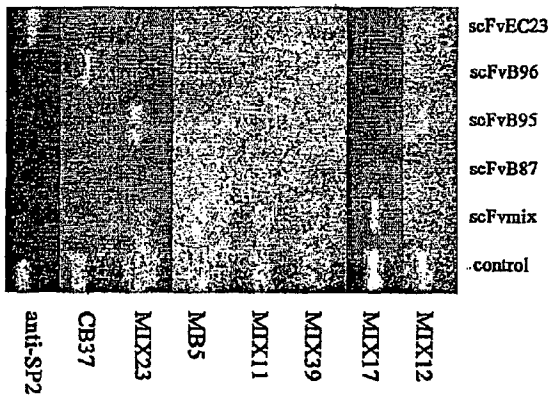

FIG. 20. Origin of anti-MCF7 scFv antibodies. One μL of each scFv phage library was amplified by PCR by using oligonucleotide primers specific for analyzed antibody genes. Corresponding PEG-purified phage was used as positive control (last line). The irrelevant anti-SP2 antibody gene of known origin, selected earlier from scFvEC23 library; derived from PBL, was also tested. Anti-MUC1 MB5 antibody and anti-CEA CB37 antibody were selected from mixture of TIL-derived libraries. Mix 11, mix 12, mix17 and mix39 antibodies were selected from mixture of TIL-derived and PBL-derived libraries Antibodies are defined in Table 5.

Figure 21:
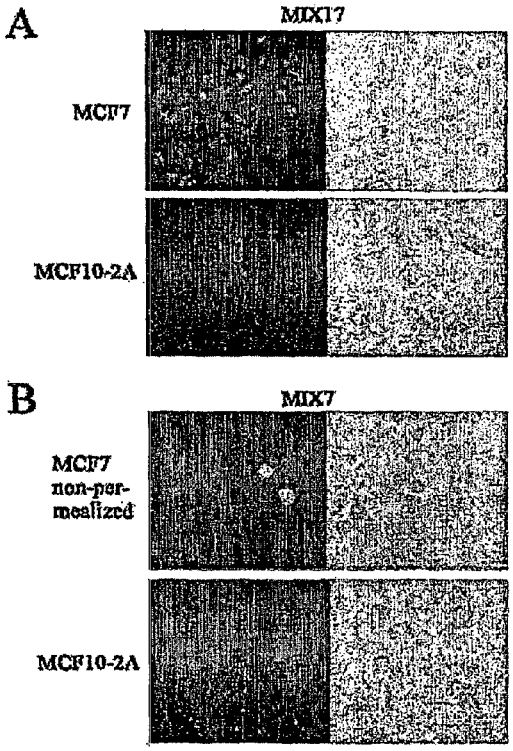

FIG. 21. Fluorescent staining of non-permealized breast carcinoma MCF7 and normal breast epithelium MCF10-2A fixed cells by phage-displayed scFv antibodies (mix17 (A), mix7 (B)).

Figure 22:
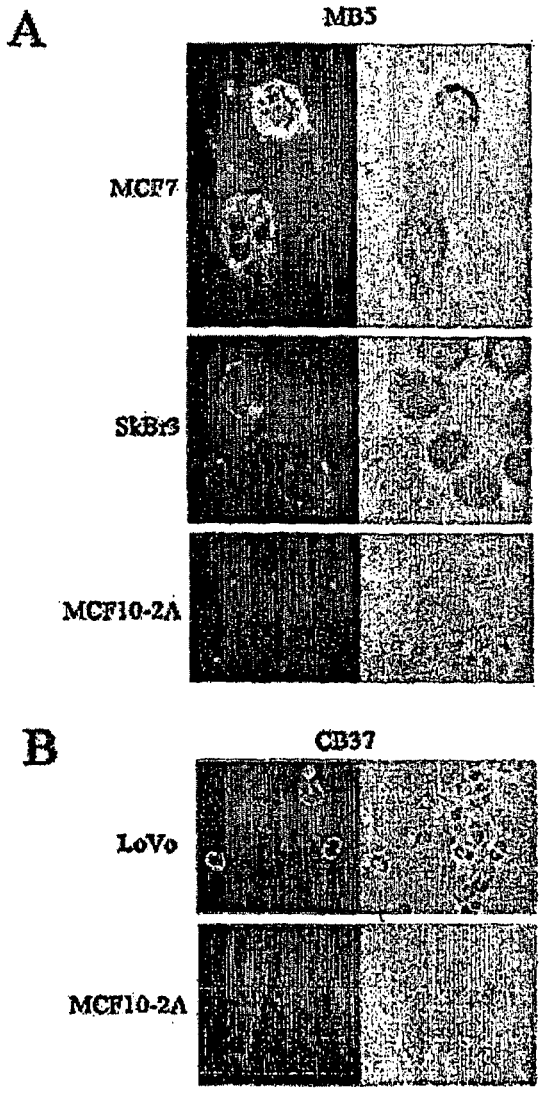

FIG. 22. A. Fluorescent staining of breast carcinoma cells MCF7, SkBr3 expressing MUC1 tumor antigen and normal breast epithelium cells MCF 10-2A by using phage-displayed anti-MUC1 MB5 scFv antibody; B. Staining of colorectal adenocarcinoma cells LoVo expressing CEA by phage-displayed anti-CEA CB37 scFv antibody. Staining of negative control MCF10-2A cells is included.

The following examples illustrates the invention.

Example 1

Construction of Novel pKM19 Phagemid Vector for Display of Single-Chain Antibodies on Filamentous Phage Introduction This work describes construction of a novel pKM19 phagemid vector for the display of single-chain antibodies on filamentous phage. This vector is characterized by several differences compared to canonical systems.

a) Amber Codon

The classic phagemids contain an amber codon between the scFv and gpIII genes, thus directing production of free scFvs and scFv-pIII fusion antibodies in suppressor bacteria, such as TG1, or DH5αF', or XL1-Blue, generally used for phage amplification. These bacterial strains, carrying the supE mutation, are glutamine-inserting suppressors with suppression efficiency dependent on the codon following the TAG (J. Mol. Biol. 1983 164(1):59-71; Mol. Gen. Genet. 1987 207(2-3):517-518). In such system, the produced free soluble scFv antibodies are secreted into the periplasm and then leak from the periplasm into the medium. Under standard phage purification protocol by PEG/NaCl, the free scFv antibodies are co-precipitated with phage particles. As a result, the concentration of free antibodies in phage suspension may be five to ten times higher than the concentration of scFv-pIII-fused proteins assembled in the phage particle. In a subsequent selection, the abundant free antibodies compete with phage-displayed antibodies for target binding. This interferes with panning efficiency and delays the selection process, specially:

i) when antigen concentration is limited (e.g. biopanning on living cells, ex-vivo cells), ii) in later panning rounds, where concentration of specific phage is relatively high, or iii) in maturation libraries, containing many relative antibodies with the same specificity.

Therefore classic phagemids need to be modified for an improved selection and/or maturation of antibodies.

As expected from literature data, the presence of an amber codon positioned in a sequence encoding for a phosphatase alkaline leader peptide in pKM19, leads to a relatively low expression level of recombinant antibodies in the amber-suppressor bacteria harboring this plasmid.

It was shown (Gene 1999 228: 23-31) that inhibition of lac promoter only by catabolic repression with glucose is not sufficient to equilibrate growth rates of different clones with or without stop codons. The lower scFv expression achieved using pKM49, reduces the toxicity of recombinant antibodies for the bacterial host and has no influence on display efficacy.

Using pKM19 the authors demonstrated:

(i) that the present level of antibody expression is sufficient to produce highly reactive phage antibodies, giving a similar signal in ELISA test as compared to pKM18 phage without amber codon;

(ii) that specific antibodies can be easily isolated from an scFv library constructed from peripheral blood lymphocytes of a patient with antibodies against a target protein after only two selection rounds;

(iii) that maturation of anti-CEA antibody leads to isolation of improved scFv clones without stop codons in comparison with maturation performed by using canonical vector (BMC Cancer 2006 6:41).

b) Gene III Protein

The pKM19 vector allows the cloning of scFv fragments as amino terminal fusion of the deleted gene III protein.

Commonly used phage display vectors for scFv lead to incorporation into the phage particles of the entire pIII fused to the antibody fragment (in Antibody Engineering—A practical approach: McCafferty, J. Hoogenboom, H. & Chiswell D., eds, pp. 325, Oxford University Press, 1996), while in the case of pComb3 plasmid utilized for Fab display (Proc. Natl. Acad. Sci. USA 1991 88(18):7978-7982), the antibody fragment is fused to the carboxy terminal half of the pIII. Infectivity of such recombinant phages is obtained during their propagation, since superinfection with a helper phage provides the native gene III protein.

According to the present data, fusion of the single-chain antibody to the C-terminal part of pIII improves phage production and display efficiency of an antibody in comparison with wt pIII protein fusion. These data are in agreement with Kretzschmar's earlier data (Gene 1995 155(1):61-65). The improved display efficiency in combination with elimination of free scFv antibodies from the incubation mixture facilitates affinity selection and results in faster enrichment of the phage pools for specific clones. This may also contribute to reduction of stop codons in selected clones since a lower number of panning/amplification rounds are necessary to complete selection. Rapidly growing defective clones have less chance of being isolated.

c) PhoA Leader Peptide

In bacteria harboring the pKM19 vector, after synthesis of recombinant protein, the PhoA leader peptide is cleaved off by leader peptidase upon membrane translocation, and scFv-pIII is assembled into the phage particle. In this way, the entire cleavage site of the alkaline phosphatase, a genuine periplasmic protein of E. coli, is preserved to guarantee efficient and correct processing and antibody assembly. As a result, the mature protein contains two additional amino acids at the N-terminus of scFv. In the described system, it is necessary to reclone the antibody gene in the appropriate plasmid for the subsequent production of soluble antibodies. At this stage, the additional amino acids can be conserved or eliminated according to specific requirements.

In conclusion, the combination of relatively low expression of displayed antibodies by introducing the amber codon before antibody gene with improved display efficiency makes the novel pKM19 phagemid useful both for selection of the recombinant scFv antibodies against desired targets from large libraries, as for their affinity maturation. The plasmid guarantees efficient display and allows reduction of biological bias against "difficult" antibodies in the delicate initial selection step. Moreover, this vector is particularly useful for the affinity maturation of antibodies, since high expression levels may increase avidity of phage particles displaying Ab, leading to selection of antibodies with only modest affinity.

Methods

Bacterial Strains and Phages

Bacterial strain DH5αF' (supE44 ΔlacU169 (100 lacZΔM15) hsdR17 recA1 endA1 gyrA96 thi-1 re1A1 F' [traD36 proAB$^+$ lacI$^q$lacZΔM15]) was used for soluble and phage antibody production. Helper phage M13 KO7 (Sambrook J, Fritsch E F, Maniatis T. Molecular cloning: A laboratory manual. Cold Spring Harbor Laboratory Press, Cold Spring Harbor, 1989) was used for phage preparation.

The anti-CEA phage antibody, MA39 (BMC Cancer 2006 6: 41), in pDN322 plasmid (J. Biol. Chem. 1998 273(34): 21169-21776) was used as source of anti-CEA antibody gene.

Construction of Plasmids

The pC89 plasmid (J. Mol. Biol. 1991 222(2): 301-310) was amplified by inverse PCR with the KM161, I(M162 oligonucleotides, containing HindIII and NotI sites (underlined) (KM161 5'-GAGG AAGCTTCCATTAAACGGGTAAAATAC-3' (SEQ ID 78); KM162 5'-TGCAATG GCGGCCGCTAATATTGTTCTGGATATTACCAGC-3' [SEQ ID 79]). In inverse PCR a Taq polymerase mixture with Pfu DNA polymerase was used to increase fidelity of DNA synthesis. Twenty-five cycles of amplification (95° C.-30 sec, 55° C.-30 sec, 72° C.-20 min) were done. The PCR product was digested with HindIII and NotI endonucleases and ligated with a KM163-KM164 oligonucleotide duplex encoding FLAG peptide and His-tail (KM163 5'-AGCTTC-CTC ATG TAG GCG GCC GCA GGA GAC TAC AAA GAC GAC GAC GAC AAA CAC CAC CAT CAC CAC CAT TAA-3' [SEQ ID 80]; KM164 5'-GGCC TTA ATG GTG GTG ATG GTG GTG TTT GTC GTC GTC GTC TTT GTA GTC TCC TGC GGC CGC CTA CAT GAGGA-3' [SEQ ID 81]). The cloned DNA duplex contained an internal NotI site, upstream of FLAG peptide encoding sequence, while the NotI site, used for cloning of the duplex, was not restored. The resulting pKM15 plasmid was newly digested with HindIII, NotI endonucleases and ligated with KM175-KM176 duplex encoding the leader sequence and the first two amino acids of the PhoA bacterial protein, containing the NcoI cloning site (KM175 5'-AGC TTA TAA AGG AGG AAA TCC TCA TGA AAC AGA GCA CCA TCG CAC TGG CAC TGT TAC CGT TAC TGT TCA CCC CGG TTA CCA AAG CAC GTA CCA TGG TTT CCC TTGC-3' [SEQ ID 82]; KM176 5'-GGC CGC AAG GGA AAC CAT GGT ACG TGC TTT GGT AAC CGG GGT GAA CAG TAA CGG TAA CAG TGC CAG TGC GAT GGT GCT CTG TTT CAT GAG GAT TTC CTC CTT TATA-3' [SEQ ID 83]). This new pKM16 plasmid was destined for soluble single-chain antibody production (FIG. 1).

The plasmid pKM16 was amplified by inverse PCR with the KM181, KM182 oligonucleotides, presenting EcoRI and BamHI restriction sites, respectively (KM181 5'-GTG GTG ATG GAATTC TTT GTC GTC GTC GTC TTT GTA GTC-3' [SEQ ID 84]; KM182 5'-CAC CAT TAA GGATCC TAA TAT TGT TCT GGA TAT TAC CAG C-3' [SEQ ID 85]). The full-length gene III (Accession number V00604) and the 3' part of the gene encoding the last 197 aa of the pIII were amplified by using the oligonucleotides KM183-KM185 or KM184-KM185 containing BamHI and EcoRI sites (underlined) and ligated into digested pKM16, giving the new plasmids pKM17 and pKM18, respectively (KM183 5'-TC TAT TCT GAATTC GCT GAA ACT GTT GAA AGT TGT TTA GC-3' [SEQ ID 86]; KM184 5'-GC CAA TCG GAA TTC CTG CCT CAA CCT CCT GTC AAT GCT-3' [SEQ ID 87]; KM185 5'-GAA CTG GGA TCC TTA AGA CTC CTT ATT ACG CAG TAT G-3' [SEQ ID 88]).

A short fragment of the pKM18 plasmid encoding the leader sequence was PCR-amplified with KM186-KM180 primers, introducing an amber mutation in PhoA leader peptide gene (KM186 5'-ACC CGT AAG CTT ATA AAG GAG GAA ATC CTC ATG AAA TAG AGC ACC ATC GC-3' [SEQ ID 89]; KM180 5'-TAG CCC CCT TAT TAG CGT TTG-3' [SEQ ID 90]). The resulting PCR product was digested with HindIII and NotI and cloned into pKM18, digested with HindIII and NotI and purified from agarose, to construct the pKM19 plasmid.

Soluble Antibody Production

A single colony was inoculated into 50 mL of LB containing 100 μg/mL Ap and 2% glucose. The culture was grown at 37° C. for 2-3 h up to O.D.=0.8. The cells recovered by centrifugation were resuspended in 50 mL of LB with Ap and 1 mM IPTG and incubated overnight at 30-32° C. Cell pellet was resuspended in 500 μL of PBS. After three cycles of freeze and thaw, cell debris was pelleted by centrifugation. The resulting supernatant was used for ELISA or for Western blot.

Purification of Lymphocytes from Peripheral Blood and cDNA Synthesis

The lymphocytes were isolated from 10 mL of fresh peripheral blood from patient EC23 (with advanced stage of breast cancer) with an anticoagulant using Ficoll-Paque Plus (Amersham Pharmacia Biotech, Sweden) according to manufacturer's instructions. mRNA was isolated from lymphocytes by using Dynabeads mRNA DIRECT Kit (Dynal, Norway). The mRNA was isolated from lymphocytes by using Dynabeads mRNA DIRECT Kit (Dynal, Oslo, Norway). One μg of the poly(A)$^+$ RNA from the lymphocytes was used to synthesize full-length cDNA by using SMART cDNA Library Construction Kit (Clontech, Palo Alto, Calif.).

ScFv Library Construction

The antibody gene repertoire was amplified using a set of primers designed for amplification of VH and VL antibody domains, while entire scFv fragments were assembled in vitro as it was described in [Pope, A. R., Embleton, M. J. & Mernaugh R. (1996) Construction and use of antibody gene repertoires. In: Antibody Engineering—A practical approach (McCafferty, J., Hoogenboom, H. & Chiswell D., eds), pp. 325, Oxford University Press]. The latter were then amplified by PCR with appropriate extension primers, incorporating NcoI, NotI restriction sites, and allowing the cloning of scFv genes into a pKM19 vector. The resulting PCR products were purified on 1% low-melting agarose gel (NuSieve 3:1 agarose, Rockland, Me.), cut with NcoI/NotI and inserted into digested plasmid. The transformed library scFvEC23 contained $1.77\times10^7$ independent clones with full-length scFv insert. The scFvEC23 library derives from PBL obtained from a single patient EC23 with advanced stage of breast cancer.

Construction of Mutated Anti-CEA scFv Library

The maturation library for the anti-CEA scFv was constructed as earlier described (BMC Cancer 2006 6:41). Briefly, mutated scFv gene fragments were generated by PCR amplification with primers: KM144-KM143 (KM143, 5'-GTCATCGTCGGAATCGTCATCTGC-3' [SEQ ID 91]; KM144, 5'-TGTGCGAAA AGTAATGAGTTTCTTTTT GACTACTGGGGC-3' [SEQ ID 92]) and KM148-KM145 (KM148, 5'-CTATTGCCTACGGCAGCCGCTGGA-3' [SEQ ID 93]; KM145, 5'-TCCGCCGAATACCAC ATAGGGCAACCACGGATAAGAGGAGTTACAGTAAT AGT CAGCC-3' [SEQ ID 94]) introducing random mutations in CDR3 regions of heavy or light chains with low frequency. Each underlined base of KM144 and KM145 oligonucleotides was replaced with mixture of G/A/T/C with a frequency of 10%. Missing scFv antibody gene parts were amplified with KM148-KM157 and KM158-KM143 primers for HC and LC, respectively (KM157 5'-TTT CGC ACA GTA ATA TAC GG-3' [SEQ ID 95]; KM158 5'-TAT GTG GTA TTC GGC GGA-3' [SEQ ID 96]). In order to reconstruct the entire gene, the corresponding fragments were combined and amplified in a PCR-like process without oligonucleotide primers. The resulting product was utilized to amplify the entire gene with external primers KM148, KM143. The final DNA fragment was agarose-purified, digested with restriction enzymes NcoI and NotI, and ligated with the digested plasmid pKM19. The resulting library contained $2.2\times10^6$ mutated antibody clones.

Competition with Soluble scFv

ELISA plates were coated, blocked and washed as above. Various quantities of anti-CEA soluble antibody MA39 (BMC Cancer 2006 6: 41) in 100 μL of blocking buffer were added to the wells and incubated for 30 min at 37° C. Then, 10 μL ($4.5\times10^9$ TU) of MA39 phage supernatant or 5 μL ($3\times10^8$ TU) of anti-CEA/pKM19 supernatant were added to the wells and incubated for another 1 h at 37° C. The plates were washed and the bound phage detected by an anti-M13 HRP-conjugated antibody. An irrelevant soluble anti-SP2 scFv (Table 5), was used at a high concentration (400 ng/well) as negative control. A lower quantity of the anti-CEA/pKM19 phage, as compared to MA39, was used to moderate ELISA reactivity of this phage.

In the case of competition with filtrates of phage supernatants, 10 μL or 50 μL of the MA39 or pKM19/anti-CEA filtrates in 100 μL of blocking buffer were used as competitors. The phage filtrates were obtained from freshly prepared phage supernatant by using filtration column Microcon 100.

Western Blot of PEG-Purified Phages

Phage was purified according to standard PEG/NaCl precipitation (Sambrook J, Fritsch E F, Maniatis T. Molecular cloning: A laboratory manual. Cold Spring Harbor Laboratory Press, Cold Spring Harbor, 1989). Protein extracts from phage samples were fractionated by SDS-PAGE and transferred onto a nitrocellulose membrane. The membrane strips were developed with an anti-FLAG AP-conjugated antibody.

Phage ELISA

Multiwell plates (Immunoplate Maxisorb, Nunc, Roskilde, Denmark) were coated ON at 4° C. with a protein solution at a concentration of 10 mg/mL in 50 mM NaHCO3, pH 9.6. After discarding coating solution, plates were blocked for 1 h at 37° C. with ELISA blocking buffer (5% non-fat dry milk, 0.05% Tween-20 in PBS). Plates were washed several times with washing buffer (0.05% Tween-20 in PBS). PEG-purified phage in blocking buffer (1:1) was added to each well and incubated for 1 h at 37° C. The plates were washed and the bound phage was detected by an anti-M13 HRP-conjugated (27-9421-01, Amersham Biosciences, Uppsala, Sweden), or anti-FLAG HRP-conjugated (A9044, Sigma, St. Louis, Mo.), or anti-FLAG AP-conjugated (A9469, Sigma) secondary antibody. In the case of HRP-conjugates, the immunoreaction was developed by incubation with TMB liquid substrate (Sigma) for 15 min and stopped by the addition of 25 μL 2 M $H_2SO_4$. The results were expressed as the difference between absorbances at 450 and 620 nm, determined by an automated ELISA reader. The AP-conjugated antibody was detected by incubation with 1 mg/mL solution of p-nitrophenyl phosphate in substrate buffer (10% diethanolamine buffer, 0.5 mM MgCl2, pH 9.8) for 60 min. The results were expressed as the difference between absorbances at 405 and 620 nm.

Antibodies are defined in table 5.

Results

The pKM16 plasmid (FIG. 1) used for production of soluble antibodies in scFv configuration is constructed as described above. This plasmid directs protein expression under the control of lacP promoter. The unique NcoI and NotI cloning sites allow insertion of an antibody gene able to express single-chain antibodies with a leader peptide of the bacterial periplasmic enzyme, alkaline phosphatase (AP), and with the first two amino acids of the mature AP protein, at the antibody's amino-terminus; and FLAG/His-tail at carboxyl-terminus of antibody. In order to confirm the plasmid's practical qualities, a gene of a single-chain antibody of known specificity, the anti-CEA MA39, was amplified by PCR and cloned into the pKM16 vector. The authors then analyzed freeze-thaw purified periplasmic proteins in Western blot developed with an anti-FLAG secondary antibody (FIG. 3). Single-chain antibody bands migrated as proteins with the expected molecular weight. N-terminal protein sequencing by Edman degradation confirms the correct processing of the leader peptide.

Phagemids for Display of scFv Antibody

A classic phagemid (pDN322) displaying the anti-CEA single-chain antibody, MA39, was compared with pKM17, pKM18 and pKM19 vectors displaying the same antibody, for phage particle production and display efficiency. The pKM17 and pKM18 plasmids (FIG. 1) allow display of antibody fragments on a phage particle by fusion to, respectively, the entire pIII (1-406 aa) or the carboxy terminal domain only (210-406 aa) of the protein. The pKM19 plasmid, derivative of pKM18, harbors an amber codon in leader sequence, thus leading to lower production of scFv-pIII fusion proteins as compared to pKM18. This is in agreement with data showing that in supE bacteria, suppression efficiency of this TAG codon, which depends on nucleotide context, is about 10-15% (J. Mol. Biol. 1983 164(1): 59-71; Mol. Gen. Genet. 1987 207(2-3): 517-518).

The authors performed functional tests by cloning the anti-CEA single-chain antibody gene into the three novel plasmids and confronting them with the original MA39 clone (anti-CEA in pDN322).

Three single colonies for each clone were incubated in 10 mL of media and phage was amplified as described in Example 2. After phagemid rescue the supernatants were titered. The authors obtained a range between 5 to $1\times10^{11}$ TU/mL for MA39, pKM18 and pKM19, displaying the anti-CEA antibody, while anti-CEA/pKM17 generated five to ten times lower titers (Table 1).

TABLE 1

Phage production by different phagemid vectors encoding the same anti-CEA gene.

| Phage | Clone | Titer | Phage | Clone | Titer |
|---|---|---|---|---|---|
| MA39 | 1 | $1.5 \times 10^{11}$ | anti-CEA/pKM18 | 1 | $2.52 \times 10^{11}$ |
| | 2 | $2.55 \times 10^{11}$ | | 2 | $2.5 \times 10^{11}$ |
| | 3 | $5.1 \times 10^{11}$ | | 3 | $1.75 \times 10^{11}$ |

TABLE 1-continued

Phage production by different phagemid vectors encoding the same anti-CEA gene.

| Phage | Clone | Titer | Phage | Clone | Titer |
|---|---|---|---|---|---|
| anti-CEA/pKM17 | 1 | $6 \times 10^{10}$ | anti-CEA/pKM19 | 1 | $3 \times 10^{11}$ |
| | 2 | $4.1 \times 10^{10}$ | | 2 | $1.8 \times 10^{11}$ |
| | 3 | $1.95 \times 10^{10}$ | | 3 | $2.8 \times 10^{11}$ |

Phage preparations were tested in ELISA, where developing was performed by using the anti-M13, or alternatively, the anti-FLAG secondary antibody. Applying different amounts of the phage per ELISA well, the authors demonstrated higher display efficiency for pKM18 and pKM19 phages in comparison with pKM17 and much higher as compared to MA39 (FIG. 4). It is interesting that the MA39 clone, which produces a higher level of antibodies than anti-CEA/pKM17, as shown by developing with anti-FLAG antibody (FIG. 4B), has a weaker signal when ELISA is developed with the anti-M13 secondary antibody (FIG. 4A).

This indicates that free scFvs, produced by the classic phagemid system, leak into the medium and coprecipitate with phage particles, consequently competing with phage-displayed antibodies for target binding. This phenomenon is due to the presence of an amber codon between scFv and pIII genes.

In order to verify this hypothesis, the authors filtered fresh preparations of MA39 and anti-CEA/pKM19 phage by using Microcon 100 Centrifugal Filter Devices (Millipore Corporation, Bedford, Mass.), able to retain large phage particles and pass through soluble scFvs. The ELISA test of phage preparations, before and after filtration, developed with anti-M13 or anti-FLAG antibodies, shows that:

(i) filtrates from both MA39 and pKM19 practically lose antibodies displayed on the phage particles, as expected;

(ii) the free antibodies are present in both preparations (FIG. 5).

However, the level of free antibodies in the anti-CEA/pKM19 sample is markedly lower. The free antibodies in this sample are the result of antibody shedding, inevitable during phage preparation and which might increase as a result of contact with components of the filtration system; while the free antibodies in MA39 samples are the result of free antibody expression and leakage into medium together with shedding.

To test the competitive ability of free antibodies in phage supernatants we had the phage supernatants of the MA39 and anti-CEA/pKM19 phages compete either with the soluble anti-CEA antibody of known concentration (FIG. 6) or with different quantities of supernatant filtrates of both phages (FIG. 7). These two experiments show that the free scFvs efficiently compete with the phage antibodies. Ten μL of the MA39 filtrate already competes with 10 μL of its own phage supernatant and 5 μL of anti-CEA/pKM19 supernanant, while the same quantity of anti-CEA/pKM19 filtrate has no effect. Marked competition is observed only by a ten-fold excess of anti-CEA/pKM19 filtrate with the same phage supernatant (50 μL of filtrate to 5 μL of supernatant). Western blot analysis (FIG. 8) of various PEG-purified phages developed with an anti-FLAG antibody detects: (i) the upper band in each sample corresponding to scFv-pIII fusion in case of MA39 and anti-CEA/pKM17 phages, and scFv-ΔpIII in case of anti-CEA/pKM18 or anti-CEA/pKM19; (ii) a notable presence of free antibodies in MA39 sample; (iii) presence of degradation products in the phage samples as previously described (Gene 1995 155(1):61-65).

Generation of scFv Antibody-Displayed Library and Isolation of Binding Specificities Using New pKM19 Plasmid The pKM19 plasmid, a derivative of pKM18, harboring amber codon in leader sequence was used for generation of scFv library to study whether low production of fused antibodies allows efficient selection of a specific antibody against a target molecule.

An scFv antibody library was constructed from human peripheral blood lymphocytes as described in Materials and Methods. The library was selected against GST fusion of a 168 aa-long SP2 Streptoccocus pneumoniae polypeptide (FEMS Microbiol. Lett. 2006 262(1):14-21), which was reactive with the blood sample utilized for the scFv library construction.

A selection procedure was designed to create a high concentration of the target protein in small incubation volume, by using biotinylated protein for panning and streptavidin-coated Dynabeads for isolation of bound phage, as described in Example 2. After completion of two panning rounds, we tested the reactivity of the phage pools in ELISA (FIG. 9). The phage pool, after the second round of affinity selection, was highly reactive with the fusion protein and negative with irrelevant proteins, such as GST, milk and streptavidin, which presented either as protein carrier or components of the selection system and all used as negative controls in ELISA, thus indicating successive selection of specific antibodies.

Finally, the authors isolated and sequenced a number of positive clones to confirm correct scFv sequence. One of the identified scFv genes was cloned in pKM16 for production of soluble anti-SP2 antibody (Table 5), which was used as an irrelevant antibody control in experiments described in FIGS. 6, 11 and 12.

Maturation of Anti-CEA scFv Antibody by Using pKM19 Vector

Affinity selection from a maturation library was carried out as described in BMC Cancer 2006 6:41. FIG. 10 shows that phage reactivity against the CEA protein grows in each successive selection round. Single phage clones with improved reactivity were isolated (FIG. 10). The authors sequenced 19 random clones from the phage pool after the second round of selection. None of the phage pool sequenced clones having increased affinity (0 of 19) presented stop codons in their sequence, whereas 70% (9 of 13) of classic phagemid system clones contained such mutations (P=0.00002, calculated according to chi square test). Thus, the use of the pKM19 vector for maturation of an anti-CEA antibody significantly improves selection results.

Two antibody genes isolated from maturation library (clones 1 and 2), were cloned in pKM16, and soluble antibodies were produced and compared with the original soluble anti-CEA MA39 and the maturated E8 antibody obtained with canonical phagemid (Pavoni et al., 2006). FIG. 11 confirms the higher affinity of the maturated antibodies.

The specificity test on newly selected scFvs shows their low background reactivity with irrelevant proteins, comparable with that of the original antibody (FIG. 12).

Example 2

Construction of the Libraries Derived from TIL and Antibody Selection

Introduction

Identification of tumor-specific recombinant antibodies from display libraries derived from lymph nodes of cancer patients is described in [Clin. Exp. Immunol. 1997 109(1): 166-74; Int. J. Mol. Med. 2004 14(4):729-35; World J. Gastroenterol. 2004 10(18):2619-23].

It is known that about 7% of lymph node-derived, and between 18-68% of TIL-derived heavy chain antibody sequences belong to clonal groups (Cancer Immunol. Immunother. 2003 52(12):715-738). This indicates both tumor-draining lymph nodes and tumor-infiltrating lymphocytes are promising sources of tumor-specific antibodies. The authors showed, by PCR amplification of specific antibody gene regions deriving from ten primary breast tumors (none being of the rare MBC histological type) of patients aged between 49-79 years, that 7 of 10 of these samples (70%), have a prominence of IgG antibody expression, as compared with IgA subclass, which correlates with the oligoclonality of the hypervariable region of heavy chain antibodies, suggesting a specific immune response to tumor-expressed antigens. Clonality of tumor-derived antibodies was confirmed by sequencing analysis.

The authors identified a panel of tumor-specific antibodies from described libraries which were reactive with ED-B domain, MUC1, CEA and MCF7 breast carcinoma cells used in respective selections. It is interesting that in performing cell-based selection without subtractive panning step on normal breast epithelium, in contrast with numerous previously described selection protocols [Int J Mol Med. 2004 14(4): 729-35; World J Gastroenterol. 2004 10(18):2619-23; Int J Oncol. 2000 16(1):187-95; Cancer Res. 1999 59(11):2718-23; Biochem Biophys Res Cmmun. 2001 280(2):548-52], the authors isolated only one scFv out of 10 was not tumor-specific and recognized normal breast epithelium as well. This probably indicates that our modest-sized libraries contain a very restricted naturally occurring antibody repertoire provided by TIL-B, rather than a vast antibody repertoire created by antibody chain shuffling. Moreover, antibody selection from a mixture of PBL and TIL-derived libraries clearly shows the latter libraries to be more efficient in cell-based panning. In fact, all isolated anti-MCF7 single-chain antibodies appeared to be derived from tumor-infiltrating lymphocytes. In summary, TIL-derived libraries gave good results in all performed selections, providing a panel of human tumor-specific antibodies, which recognize tumor cell-surface antigens useful for therapy and diagnosis of cancer.

In this study we demonstrated that application of novel improved phage-display vector pKM19 led to the isolation of a large panel of antibodies derived from pieces of tumor tissue removed in tumor surgery, against known tumor antigens and entire tumor cells, and which are potentially useful in therapy of cancer. These results are similar to the results obtained by direct screening of soluble TIL-derived antibody expression libraries (Cancer Immunol. Immunother. 2002 51(2):79-90). The direct screening is an unbiased screening strategy which does not depend from phage amplification steps and results more efficient as compared to affinity selection performed with canonical display vectors, which failed to select tumor-specific antibodies in analogous works (Cancer Res. 2001 61(21):7889-99; Proc. Natl. Acad. Sci. U.S.A. 2001 98(22): 12659-64; Int. J. Cancer 2001 93:832-40). Our results indicate that pKM19 vector improves the selection results in comparison with classic display vectors and at the same time, provides possibility to apply affinity selection methodologies, facilitating manipulation with large libraries.

In conclusion, our results indicate that naturally occurring immune responses to tumor-related antigens exist in a majority of patients with breast cancer, not only in hystologically-defined MCB. Tumor samples as small as 0.2 g obtained as surgical material and, can be exploited as an appropriate source for generation of recombinant phage display libraries enriched for tumor-specific antibodies. Isolation of a panel of anti-tumor scFvs through selection against desirable protein targets, as well as against living breast carcinoma cells, shows this approach to be very promising for development of human therapeutic antibodies. Moreover, investigation of the protein targets eliciting production of tumor cell-specific antibodies in a tumor microenvironment may (i) provide important details about individual immunoreactivity of a given patient, affording a prognostic value; (ii) open a large perspective for discovery of novel tumor-specific antigens.

Methods

Tissue and Blood Samples

Specimens of breast carcinoma and fresh peripheral blood from breast cancer patients (B81-B96, EC23) were obtained from M. G. Vannini Hospital, Rome. All the human biological samples were obtained through informed consent.

Cell Lines

The breast carcinoma cell lines MCF-7 (ATCC Number: HTB-22), MDA-MB-468 (ATCC Number: HTB-132) and SkBr3 (ATCC Number: HTB-30), and colon adenocarcinoma cell line LoVo (ATCC Number: CCL-229) were maintained according to manufacturer's instructions. Human foreskin fibroblasts (HFF) were cultivated in DMEM supplemented with 10% FBS and 1% L-glutamine. Immortal breast epithelial cells MCF10-2A (ATCC number CRL-10781) [Cancer Res. 1990 50(18):6075-86] were propagated according to manufacturer's instructions, and used as negative controls in ELISA tests.

Purified Tumor Antigen Proteins

Human CEA protein, purified from colon carcinoma and liver metastases, was purchased from USBiological (#C1300-16, United States Biological, Swampscott, Mass.).

Biotinylated recombinant ED-B domain of fibronectin was obtained from Sigma-Tau S.p.A. (Pomezia, Rome).

Recombinant MUC1 protein was obtained in several steps. Two over-lapping oligonucleotides KM358 5'-ACT TCA GCT CCG GAC ACC CGT CCG GCT CCG GGT TCC ACC GCT CCG CCG GCT CAC GGT GTC-3' [SEQ ID 97] and KM359 5'-CGG AGC CGG ACG GGT GTC CGG AGC TGA AGT GAC ACC GTG AGC CGG CGG AGC GGT GGA ACC-3' [SEQ ID 98] encoded for 20-aa MUC1 repeat, were assembled in PCR-like process, in which 25 cycles of PCR amplification were performed with 0.2 μM/μL of KM358 and KM359. High-weight DNA band was then cut from agarose gel and ligated with a short adapter, obtained by annealing a KM328 5'-CT AGT TCG TCG GGT TCG TCG GGA-3' [SEQ ID 99] oligonucleotide and a phospharylated one: KM329 5'-TCC CGA CGA ACC CGA CGA A-3' [SEQ ID 100]. The resulting DNA fragment was purified from adapter excess, phosphorylated and cloned into digested and dephospharylated pGEX-SN [Int J Cancer. 2003 106(4):534-44], derived from pGEX-3X plasmid [Gene 1988 67:31-40] . GST-fused MUC1 recombinant protein, containing a 107-aa MUC1 sequence, containing 5.3 repeats, was purified according to standard methods [Gene 1988 67:31-40].

Purification of Lymphocytes from Peripheral Blood

The lymphocytes were isolated from 10 mL of fresh peripheral blood mixed with anticoagulant by using Ficoll-Paque Plus (Amersham Pharmacia Biotech, Sweden) according to manufacturer's instructions. mRNA was isolated from lymphocytes by using Dynabeads mRNA DIRECT Kit (Dynal, Norway).

RNA Extraction and cDNA Synthesis

Tumor specimens of about 200 mg from breast carcinoma patients were obtained as surgical discard samples and immediately frozen in liquid nitrogen. Total RNA was prepared by Total RNA Isolation System (Promega, Madison, Wis.) and purified to poly $A^+$ RNA using PolyATract mRNA Isolation Systems (Promega). Five hundred ng of poly$(A)^+$ RNA from breast carcinomas or 1 μg of the poly$(A)^+$ RNA from the lymphocytes were used to synthesize full-length cDNAs by using SMART cDNA library construction kit (Clontech, Palo Alto, Calif.).

Analysis of Antibody Gene Expression by PCR

The hypervariable V(D)J antibody region was amplified by PCR from cDNA templates by using site-specific primers 5'-GGACACGGCT(G/C)TGTATTACTG-3' [SEQ ID 101] and 5'-GCTGAGGAGACGGTGACC-3' [SEQ ID 102] designed in designed in a study by Hansen and colleagues [Proc Natl Acad Sci USA 2001 98(22):12659-64]. IgG1, IgG2 and IgA subclass determination was done as described in [J Immunol. 2002 169(5):2701-11] by individually combining constant region-specific primers for IgG1, IgG2 and IgA genes (CG1d, CG2a and CA1, respectively) with a set of variable heavy chain primers: VH135, VH3a, VH3f, VH4, VH4b. These primers were designed for construction of human Fab libraries [Barbas C F III, Burton DR (1994) Monoclonal antibodies from combinatorial libraries. Cold Spring Harbor Laboratory Course Manual].

ScFv Library Construction

Antibody gene repertoire was amplified using set of primers designed for amplification of VH and VL antibody domains [Pope, A. R., Embleton, M. J. & Memaugh R. (1996) Construction and use of antibody gene repertoires. In: Antibody Engineering—A practical approach (McCafferty, J., Hoogenboom, H. & Chiswell D., eds), pp. 325, Oxford University Press] and scFv fragments were assembled in vitro as described earlier [Pope A Ret al., 1996]. The scFv fragments were then amplified by PCR with appropriate extension primers, incorporating NcoI, NotI restriction sites, permitting the cloning of the scFv genes into pKM19 vector. The resulting PCR products were purified on a 1% low-melting agarose gel (NuSieve 3:1 agarose, Rockland, Me.). The DNA fragments were digested with NcoI/NotI and inserted into pKM19 vector. The ligated DNA was used to transform competent bacterial cells DH5αF' (supE44 ΔlacU169 (ϕ80 lacZΔM15) hsdR17 recA1 endA1gyrA96 thi-1 re1A1 F' [traD36proAB$^+$ lacI$^q$lacZΔM15]) by electroporation. The transformed cells were plated on 20 agar dishes (ø15 cm), containing LB agar, 100 μg/mL ampicillin and 1% glucose. After overnight incubation at 37° C., bacterial colonies were scraped from the plates and resuspended in LB, containing 10% of glycerol. Aliquots of this cell suspension were stored at −80° C. and used for phage amplification.

Phage Amplification

Forty μL of scraped bacterial cells were incubated in 40 mL of LB containing ampicillin and 1% glucose up to O.D.=0.2. The bacteria were collected by centrifuging and resuspended in 40 mL of LB with ampicillin without glucose. About $6\times10^9$ pfu of helper M13K07 were added to each mL of cell suspension, incubated for 15 min at 37° C. without agitation and a further 2 h in a shaker. Kanamycin was added to final concentration 20 μg/mL and cells were incubated ON at 32° C. Phage was purified according to standard PEG/NaCl precipitation [Sambrook J, Fritsch E F, Maniatis T. Molecular cloning: A laboratory manual. Cold Spring Harbor Laboratory Press, Cold Spring Harbor, 1989].

Cell-Based Selection of Antibodies from Phage-Displayed Library

MCF-7 semi-confluent cells (about $2\times10^7$) were rinsed 3 times with PBS buffer and incubated with 2 mL of 2 mM EDTA in PBS for 15 min at 37° C. Ten mL of PBS containing 10 mM $MgCl_2$ were added to the cells, they were accurately removed by pipetting. The cells were collected by centrifuging, washed once with 10 mL of PBS/$MgCl_2$ and finally resuspended in 1 mL of freshly prepared blocking buffer: 4% non-fat dry milk, 0.05% Tween 20, $5\times10^{11}$ pfu of f1 UV-killed phage. The cells were blocked for 30 min at RT on rotating wheel, then collected and incubated for 1 h at 37° C. on the wheel with about $5\times10^{11}$ TU of freshly amplified scFv antibody library in 1 mL of blocking buffer. The cells were washed 5 times with PBS/Tween. The bound phage was eluted by adding 400 μL of 0.1 M HCl, pH 2.2 (adjusted by glycine). Cell suspension was incubated with elution solution for 10 min at RT, neutralized by 40 μL of 2M Tris-HCl, pH 9.6 and used for infection of bacterial cells. The bacteria were plated on two LB agar dishes (ø15 cm), containing 100 μg/mL ampicillin and 1% glucose. Scraped bacteria were used for phage amplification.

Affinity Selection on Purified Protein Targets.

CEA and MUC1 were biotinylated as described in [Harlow E. & Lane D. Antibody: A laboratory manual. Cold Spring Harbor Laboratory Press, Cold Spring Harbor, 1988]. About $5\times10^{11}$ TU of freshly amplified scFv antibody libraries were preincubated with 50 μL of AD202 bacterial extract in blocking buffer for 30 min at 37° C. Twenty γ of a biotinylated protein were added to the reaction mixture and incubated for another h at 37° C. under gentle agitation. The bound phage was captured by using streptavidin-coated Dynabeads M-280 (112.05, Dynal, Oslo, Norway) according to manufacturer's instructions, washed 5-10 times with PBS/Tween, then, eluted and amplified as above.

ELISA Experiments

The cells were grown in 96-well plate until almost confluent. After discarding the growth medium, 100 μL of freshly prepared 4% paraformadehyde (#15710, Electron Microscopy Science, Hatfield, Pa.) in PBS were rapidly added for 10 min. The fixing solution was removed by pipetting and cells were incubated with blocking buffer (5% milk, 0.05% Tween 20 in PBS) for 30 min at RT. PEG purified phage in blocking buffer (1:1) was added to cells and incubated for 1 h at 37° C. under gentle agitation. The cells were washed 3 times and an anti-M13 HRP-conjugated antibody (Pharmacia) was used for developing the reaction. All assays were done in triplicate.

Immunofluorescence Staining

The cells were grown in a 24-well plate for cell culture (Nunc, Roskilde, Denmark), fixed as above and blocked with 3% BSA in PBS for 1 h at room temperature. PEG-purified phage in 1% BSA/PBS was added to the cells and incubated for 1 h under gentle agitation at 37° C. The cells were washed three times with 1% BSA/PBS and incubated with an anti-M13 mouse monoclonal antibody (27-9420-01, Amersham Biosciences) for 30 min at 37° C. The cells were washed as above and then incubated with an FITC-conjugated anti-mouse goat polyclonal antibody (554001, BD Biosciences Pharmingen, San Jose, Calif.) at a concentration of 5 μg/mL for 30.1 min at 37° C. under gentle agitation. After the last incubation, cells were washed five times, dried in the dark, mounted with Vectashield medium (Vector Laboratories, Inc. Burlingame, Calif.) and cover glasses, and analyzed using an inverted fluorescence microscope.

All antibodies are defined in table 5.

Results

Characterization of the Lymphoplasmatic Cell Infiltrate in Breast Tumor Samples

Ten tumor specimens from breast cancer patients (aged 47-79 years) for presence and nature of TIL-B by PCR amplification of V(D)J antibody segments (CDR3) and by comparison of representation of IgG and IgA antibody classes were examined.

The expression patterns of the antibody fragment genes was analyzed by semi-quantitative PCR from SMART cDNA template. The panel of cDNAs from ten breast carcinomas, from samples of normal breast, normal testis and peripheral blood lymphocytes from healthy donors were normalized by PCR amplification of a housekeeping gene, β-actin and are shown in FIG. 13A.

Hypervariable heavy chain antibody regions (V(D)J) were amplified as described in Materials and Methods. After analysis by agarose gel electrophoresis, the same PCR products were fractionated by high resolving 10% PAGE (FIG. 13B). In applying this technique, the authors observe that 7 out of 10 tumor-deriving samples contain various numbers of discrete bands, characterizing oligoclonality of the immune response in these patients, while the well-amplified normal breast and peripheral lymphocyte DNA fragments do not contain intensive bands and form a smear, consisting of the bands of different length. The observed oligoclonality of the immunoglobulins does not correlate with the age of the patients.

In order to analyze the antibody subclass distributions we amplified Ig genes from breast carcinoma cDNAs and normal breast, using subclass-specific primers. In agreement with previous assay, the 3 cDNA tumor samples, not containing oligoclonal bands in PCR-amplified V(D)J regions, have a prevalence of the IgA band in comparison with IgG1 and IgG2 bands, just as in a sample of normal breast where IgA generally represents the major Ig class (Br. Med. J. 1976 2(6034):503-506). On the other hand, samples showing oligoclonality in the first assay contain IgG1, or both IgG1 and IgG2 as dominant antibody bands, in contrast to normal breast. FIG. 14 shows four more characteristic examples along with normal breast sample.

Oligoclonality of TIL-B Derived Antibodies in Breast Cancer Patients was Confirmed by Sequencing The authors chose two cDNA samples (B92, B93) giving strongest single bands in V(D)J test, for sequencing analysis. The nucleotide sequences of 17 and 13 randomly picked clones containing γ antibody genes deriving from B92 and B93 cDNA, respectively, were determined and their amino acid sequences were deduced. All 30 clones encoded in-frame correct organized heavy chains. More frequently isolated antibodies (B92-A and B93-A1) contained V(D)J regions of the exact length corresponding to the strong bands earlier observed in FIG. 13B (lines with B92 and B93 samples) (FIG. 15), thus indicating that both PCR amplification with variable heavy chain primers and the cloning step do not introduce any particular bias interfering with heavy chain frequencies in the constructed library.

As indicated FIG. 15, six somatic mutations were identified in antibody fragments. These mutations are localized in variable CDRs of γ chain of the same specificity, while only one mutation is found out of variable regions (P=0.0002). Therefore, oligoclonality of antibody repertoire derived from tumor tissue is a natural immune response occurring within tumor tissue driven by tumor antigens, and not an artifact introduced by PCR amplification.

Library Construction

Four scFv antibody libraries were constructed using seven cDNAs as template, characterized by oligoclonality of the immune response (see list of libraries in Table 2). Only library scFvEC23 (described in Example 1) was constructed from peripheral blood lymphocytes, obtained from a single patient with advanced stage of breast cancer.

TABLE 2

ScFv-antibody library list.

| Library | Source of Ig genes | Patient (age) | Library complexity |
|---|---|---|---|
| ScFvB87 | TIL | B87 (55) | $4.7 \times 10^5$ |
| ScFvB95 | TIL | B95 (73) | $1.1 \times 10^7$ |
| ScFvB96 | TIL | B96 (72) | $2.6 \times 10^7$ |
| ScFvmix | TIL | B85 (47), B91 (70), B92 (79), B93 (66) | $2.4 \times 10^7$ |
| ScFvEC23 | PBL | EC23 (65) | 1.8 × 107 |
| mixTIL | TIL | — | ScFvB87 + ScFvB95 + |
| mixLIB | TIL + PBL | | scFvB87 + scFvB95 + scFvmix + scFvEC23 |

Selection of Specific Anti-Tumor Antibodies from Phage Display Libraries Generated from TIL-B and PBL The authors examined directly the possibility of selecting specific antibody fragments from phage libraries against common cancer antigens including ED-B domain of fibronectin [EMBO J. 1987 6(8):2337-42], MUC1 [Cancer Res. 1992 52(22):6365-70; Hum Pathol. 1995 26(4):432-9], and CEA [J. Clin. Lab. Anal. 5: 344-366; Semin Cancer Biol. 1999 9:67-81; Cancer Res. 2002 62:5049-5057]. Under conditions described in Materials and Methods a mixture of four TIL-derived scFv antibody-displayed libraries (scFvB87, scFvB95, scFvB96 and scFvmix) named mixTIL library (Table 2) and the scFvEC23 library were panned separately against three protein targets in several rounds. In every case we observed that pools of phage were already positive against the selecting antigen after second and third rounds of panning (FIG. 16). Randomly picked clones were tested for binding reactivity against the antigens. Results of the test of random phage clones from third round phage pools are summarized in Table 3. Positive clones were analyzed by fingerprinting using HaeIII and AluI double digestion and unique antibody clones were sequenced. FIG. 17 represents ELISA of single scFv-phages selected on purified antigens. The analyzed single clones strongly bind respective antigens and does not react with irrelevant proteins. This result indicates the pKM19 vector is a suitable tool for selection of anti-tumor antibodies from TIL and PBL-derived libraries.

TABLE 3

Result of selections through the use of three purified tumor antigens.

| Target antigen | Library | Positive clones/ tested clones | Isolated antibody genes |
|---|---|---|---|
| ED-B | mixTIL | 10/10 | 1 |
| | scFvEC23 | 10/10 | 3 |
| MUC1 | mixTIL | 2/16 | 1 |
| | scFvEC23 | 6/8 | 2 |
| CEA | mixTIL | 17/20 | 4 |
| | scFvEC23 | 15/20 | 3 |

Cell-Based Selection of Tumor-Specific Antibodies

The authors tested functionality of a single TIL-derived library (scFvB96) by selecting breast cancer-specific antibodies through cell-based panning on MCF-7 breast carcinoma cell line. Four libraries, including scFvB87, scFvB95, scFvmix and scFvEC23, were pooled together (library named mixLIB, table 2) and panned on the same type of cells. Four or five selection rounds on MCF-7 cells were necessary for mixLIB or scFvB96 libraries, respectively, in order to enrich the phage pools for specific cell binders (FIG. 18). Then, randomly picked clones were analyzed for entire scFv antibody presence. The full-length scFv-phage clones were tested by cell-based ELISA, and analyzed by fingerprinting, and various positive clones were sequenced. Amino acid sequences were deduced from DNA sequences, confirming correct, in-frame antibody structures. Clone analysis data are summarized in Table 4.

TABLE 4

Result of selection on intact/living human breast carcinoma MCF7 cells.

| | MCF-7 selection | |
|---|---|---|
| Library | scFvB96 | mixLIB |
| Selection round | 5 | 4 |
| Full-length scFv/tested clones | 12/40 | 30/40 |
| Positive clones/full-length tested clones | 5/12 | 22/30 |
| Isolated antibody genes | 2 | 8 |

The reactivity and specificity of cell-selected antibodies were verified by ELISA on both breast carcinoma cell lines: MCF-7, MDA-MB-468, and normal cells, as negative controls: MCF10-2A (human breast epithelium), HFF (human fibroblasts) (FIG. 19). Among 10 different selected scFv antibodies belonging to 7 specificity groups (mix7, mix12, mix25 antibodies have the same heavy chain sequence and different light chains; mix8 and mix39 antibodies have similar sequences with minor differences), 9 are specific for breast carcinoma cells, while only B96/4F scFv antibody binds normal epithelial cells as well.

Cell-Selected Antibodies Derive from TIL

Mix11, mix12, mix17, mix23 and mix39 scFv antibodies (Table 4) were selected from a mixture of PBL and TIL-derived libraries. The authors investigated the origin of these antibodies in order to see which type of library works better in equal selection conditions. One μL of each amplified library was used as template for PCR amplification with pair of oligonucleotide primers specific for each antibody (FIG. 20). This analysis shows that the 5 tested scFv antibodies, isolated from a mixture of libraries, belong to TIL-derived antibodies. Antibody genes of mix7 and mix25 antibodies (having the same heavy chain as mix12, table 5), and mix8 (similar to mix39, table 5) are believed to have a similar origin. For irrelevant anti-SP2 antibody, which was selected from the scFvEC23 library, its origin from PBL-derived library was confirmed. Anti-MUC1 MB5 and anti-CEA CB37 antibodies, which were selected from the mixture of four TIL-derived libraries (mixTIL) were shown to derive from the scFvmix and the scFvB96 libraries, respectively.

Fluorescent Staining of Tumor Cells

Binding specificities of several clones, including mix17, mix7 (FIG. 21), anti-Muc1 antibody MB5 and anti-CEA CB37 (FIG. 22) were assayed by immunofluorescent staining of tumor cells directly with scFvs antibodies displayed on the phage. Mix17 scFv recognizes major part of non-permealized MCF7 breast carcinoma cells in this experiment (FIG. 21A), while mix7 stains a low percentage of cells, probably apoptotic cells.

MB5 antibody intensively stains MCF7 cells, known for high MUC1 expression, and reacts well also with another breast carcinoma cell line, SkBr3(FIG. 22). CB37 antibody stains LoVo cells. No background staining for normal breast epithelium was observed for both MB5 and C1337 antibodies.

Example 3

Maturation of Anti-MUC1 and Anti-CEA scFv Antibodies

To increase affinity of tumor specific antibodies CB37 and MB5 we performed affinity maturation of the antibodies in vitro. The new maturation libraries were created by combination of genes of single VH chains derived from CB37 and MB5, respectively, with various genes of VL chains derived from TIL and PBL of tumor patients. The libraries were constructed as described in Example 1 and 2.

Methods

Affinity Selection

The affinity selection was performed by using biotinylated proteins as described in Example 2, with the difference that for first round of affinity selection we used 10 μg of the protein and for second only 50 ng. Clones found positive in ELISA were screened by PCR and fingerprinting with restriction enzymes AluI and HaeIII to identify different clones. The DNA sequence of the clones were determined. The antibody genes from clones having reactivity against target proteins higher than original antibodies were cloned in pKM16 to produce scFvs in soluble form as described in Example 1.

Characterization of Maturated Antibodies

The maturated antibody fragments were characterized for antigen binding.

The new anti-MUC1 antibodies MB5/C'1 and MB5/C'3 and anti-CEA maturated antibodies CB37/3B and CB37/9C (Table 5) in soluble form were characterized by Surface Plasmon Resonance (Biacore) as described in BMC Cancer 2006 6:41. Results are shown in table 6.

TABLE 5

Selected antibodies. MixTIL and MixLIB are mixture of libraries defined in table 2.

| Anti-body | Anti-gen | Library used for selection | Nucleotide/Amino acid sequence |
|---|---|---|---|
| EDE1 | ED-B | scFvEC23 | CAGGTGCAGCTGCAGGAGTCTGGGGCTGAGGTGAAGAAG<br>CCTGGGGCCTCAGTGAAGGTCTCCTGCAAGGCTTCTGGA<br>TACACCTTCACCGGCTACTATATGCACTGGGTGCGACAG<br>GCCCCTGGACAAGGGCTTGAGTGGATGGGATGGATCAAC<br>CCTAACAGTGGTGGCACAAACTATGCACAGAAGTTTCAG<br>GGCAGGGTCACCATGACCAGGGACACGTCCATCAGCACA<br>GCCTACATGGAGCTGAGCAGGCTGAGATCTGACGACACG<br>GCCGTGTATTACTGTGCGAGAGATTCGCCACAAAATTGT<br>ACTAATGGTGTATGCCACCGGGGGAGTCATGTCCACTAC<br>TACGGTATGGACGTCTGGGGCCAAGGCACCCTGGTCACC<br>GTCTCTTCAGGTGGGGGCGGTTCAGGCGGAGGTGGCTCT<br>GGCGGTGGCGGATCGCAGTCTGCCCTGACTCAGCCTGCC<br>TCCGCGGCCGGGTCTCCTGGACAGTCAGTCACCATCTCC<br>TGCACTGGAACCAGCAGTGATGTTGGTGGTTATAACTAT<br>GTCTCCTGGTACCAACAGCACCCAGGCAAAGCCCCCAAA<br>CTCATGATTTATGACGTCAATAAGCGGCCCTCAGGGGTC<br>CCTGATCGCTTCTCTGCCTCCAAGTCTGGCAACACGGCC<br>TCCCTGACCGTCTCTGGGCTCCAGGCTGACGATGAGGCT<br>GATTACTACTGCGCTTCATATGCAGGCACCTACAGTTAT<br>GTCTTCGGAACTGGGACCCAGCTCACCGTTTTAGGTGCG<br>GCCGCAGGAGA [Seq ID 22]<br><br>QVQLQESGAEVKKPGASVKVSCKASGYTFTGYYMHWVRQ<br>APGQGLEWMGWINPNSGGTNYAQKFQGRVTMTRDTSIST<br>AYMELSRLRSDDTAVYYCARDSPQNCTNGVCHRGSHVHY<br>YGMDVWGQGTLVTVSSGGGGSGGGGSGGGGSQSALTQPA<br>SAAGSPGQSVTISCTGTSSDVGGYNYVSWYQQHPGKAPK<br>LMIYDVNKRPSGVPDRFSASKSGNTASLTVSGLQADDEA<br>DYYCASYAGTYSYVFGTGTQLTVLGAAA [Seq ID 23] |
| EDE3 | ED-B | scFvEC23 | GAGGTGCAGCTGTTGCAGTCTGGGGCCGAGGTGAAGAAG<br>CCTGGGGCCTCAGTGAAGGTCTCCTGCAAGGCTTCTGGA<br>TACACCTTCACCGGCTACTATATGCACTGGGTGCGACAG<br>GCCCCTGGACAAGGGCTTGAGTGGATGGGATGGATCAAC<br>CCTAACAGTGGTGGCACAAACTATGCACAGAAGTTTCAG<br>GGCAGGGTCACCATGACCAGGGACACGTCCATCAGCACA<br>GCCTACATGGAGCTGAGCAGGCTGAGATCTGACGACACG<br>GCCGTGTATTACTGTGCGAGAGATTCGCCACAAAATTGT<br>ACTAATGGTGTATGCCACCGGGGGAGTCATGTCCACTAC<br>TACGGTATGGACGTCTGGGGCCAGGGAACCCTGGTCACC<br>GTCTCCTCAGGTGGGGGCGGTTCAGGCGGAGGTGGCTCT<br>GGCGGTGGCGGATCGCAGTCTGCCCTGACTCAGCCTGCC<br>TCCGCGGCCGGGTGTCTTGGACAGTCAGTCACCATCTCC<br>TGCACTGGAACCAGCAGTGATGTTGGTGGTTATAAATAT<br>GTCTCCTGGTACCAACAGCACCCAGGCAAAGCCCCCAAA<br>CTCATGATTTATGACGTCAATAAGCGGCCCTCAGGGGTC<br>CCTGATCGCTTCTTTGCCTCCAAGTCTGGCAACACGGCC<br>TCCCTGACCGTCTCTGGGCTCCAGGCTGACGATGAGGCT<br>GATTACTACTGCGCTTCATATGCAGGCACCTACAGTTAT<br>GTCTTCGGAACTGGGACCCAGCTCACCGTTTTAGGTGCG<br>GCCGCA [Seq ID 24]<br><br>EVQLLQSGAEVKKPGASVKVSCKASGYTFTGYYMHWVRQ<br>APGQGLEWMGWINPNSGGTNYAQKFQGRVTMTRDTSIST<br>AYMELSRLRSDDTAVYYCARDSPQNCTNGVCHRGSHVHY<br>YGMDVWGQGTLVTVSSGGGGSGGGGSGGGGSQSALTQPA |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | SAAGCGLQSVTISCTGTSSDVGGYKYVSWYQQHPGKAPK<br>LMIYDVNKRPSGVPDRFPASKSGNTASLTVSGLQADDEA<br>DYYCASYAGTYSYVFGTGTQLTVLGAAA [Seq ID 25] |
| EDES | ED-B | scFvEC23 | GAGGTGCAGCTGGTGGAGTCTGGGGCTGAGGTGAAGAAG<br>CCTGGGGCCTCAGTGAAGGTCTCCTGCAAGGCTTCTGGA<br>TACACCTTCACCGGCTACTATATGCACTGGGTGCGACAG<br>GCCCCTGGACAAGGGCTTGAGTGGATGGGATGGATCAAC<br>CCTAACAGTGGTGGCACAAACTATGCACAGAAGTTTCAG<br>GGCAGGGTCACCATGACCAGGGACACGTCCATCAGCACA<br>GCCTACATGGAGCTGAGCAGGCTGAGATCTGACGACACG<br>GCCGTGTATTACTGTGTGAGAGGTTCGCCACAAAATTGT<br>ACTAATGGTGTATGCCACCGGGGGAGTCATGTCCACTAC<br>TACGGTATGGACGTCTGGGGCCAAGGGACCACGGTCACC<br>GTCTCCTCAGGTGGGGGCGGTTCAGGCGGAGGTGGCTCT<br>GGCGGTGGCGGATCGCAGTCTGCCCTGACTCAGCCTGCC<br>TCCGTGTCTGGGTCTCCTGGACAGTCGATCACCATCTCC<br>TGCACTGGAACCAGCAGTGATGTTGGGAGTTATAACCTT<br>GTCTCCTGGTACCAACAGCACCCAGGCAAAGCCCCCAAA<br>CTCATGATTTATGAGGTCAGTAATCGGCCCTCAGGGGTT<br>TGTAATCGCTTCTCTGGCTCCAAGTCTGGCAACACGGCC<br>TCCCTGACCATCTCTGGGCTCCAGGCTGAGGACGAGGCT<br>GATTATTACTGCAGCTCATATACAAGCAGCAGCACTCTC<br>GAGGTGTTCGGCGGAGGGACCCAGCTCACCGTTTTAGGT<br>GCGGCCGCA [Seq ID 26] |
| | | | EVQLVESGAEVKKPGASVKVSCKASGYTFTGYYMHWVRQ<br>APGQGLEWMGWINPNSGGTNYAQKFQGRVTMTRDTSIST<br>AYMELSRLRSDDTAVYYCVRGSPQNCTNGVCHRGSHVHY<br>YGMDVWGQGTTVTVSSGGGGSGGGGSGGGGSQSALTQPA<br>SVSGSPGQSITISCTGTSSDVGSYNLVSWYQQHPGKAPK<br>LMIYEVSNRPSGVCNRFSGSKSGNTASLTISGLQAEDEA<br>DYYCSSYTSSSTLEVFGGGTQLTVLGAAA [Seq ID 27] |
| EDBS | ED-B | mixTIL | CAGGAGGTGCAGCTGGTGGAGTCTGGGGGTGGCTTGGTC<br>CAGCCTGGGGGGTCCCTGAGACTCTCCTGTGCAGCCTCT<br>GGATTCACCCTCAGTAGCTATGCTATGCACTGGGTCCGC<br>CAGGCTCCAGGGAAGGGGCTGGAGTGGGTCTCAACTATT<br>AGTGGTGGTGGTGGTAGCACATACTACGCAGACTCCGTG<br>AAGGGCCGGTTCACCATCTCCAGAGACAATTCCAAGAAC<br>ACGCTGTATCTGCAAATGAACAGCCTGAGAGCCGAGGAC<br>ACGGCCGTATATTACTGTGCGAGACGGGGGCGGGCTTTT<br>GATATCTGGGGCCAAGGGACCACGGTCACCGTCTCCTTA<br>GGTGGAGGCGGTTCAGGCGGAGGTGGCTCTGGCGGTGGC<br>GGATCGCAGTCTGTGTTGACGCAGCCGCCCTCAGTGTCT<br>GGGGCCCCAGGGCAGAGGGTCACCATCTCCTGCACTGGG<br>AGCAGCTCCAACATCGGGGCGGGGTATGATGTACACTGG<br>TACCAGCAGCTTCCAGGAACAGCCCCCAAACTCCTCATT<br>TATGGTAACAGCAATCGGCCCTCAGGGGTCCCTGACCGA<br>TTCTCTGGCTCCAAGTCTGGCACCTCAGCCTCCCTGGCC<br>ATCACTGGGCTCCAGGCTGAGGATGAGGCTGATTATTAT<br>TGCTCCAGTCCTATGATCAGCAGCCTGAGTGGTCATGTG<br>GTATTCGGCGGAGGGACCAAGGTGACCGTCCTAGGTGCG<br>GCCGCA [Seq ID 28] |
| | | | QEVQLVESGGGLVQPGGSLRLSCAASGFTLSSYAMHWVR<br>QAPGKQLEWVSTISGGGGSTYYADSVKGRFTISRDNSKN<br>TLYLQMNSLRAEDTAVYYCARRGRAFDIWGQGTTVTVSL<br>GGGGSGGGGSGGGGSQSVLTQPPSVSGAPGQRVTISCTG<br>SSSNIGAGYDVHWYQQLPGTAPKLLIYGNSNRPSGVPDR<br>FSGSKSGTSASLAITGLQAEDEADYYCSSPMISSLSGHV<br>VFGGGTKVTVLGAAA [Seq ID 29] |
| ME1 | MUC1 | scFvEC23 | CAGGTGCAGCTGGTGCAGTCTGGGGCTGAGGTGAAGAAG<br>CCTGGGGCCTCAGTGAAGGTCTCCTGCAAGGCTTCTGGA<br>TACACCTTCACCGGCTACTATATGCACTGGGTGCGACAG<br>GCCCCTGGACAAGGGCTTGAGTGGATGGGATGGATCAAC<br>CCTAACAGTGGTGGCACAAACTATGCACAGAAGTTCCAG<br>GGCAGGGTCACCATGACCAGGGACACGTCCATTGGCACA<br>GTCTACATGGAGTTGAGCAGCCTGACATCTGACGACACG<br>GCCATGTATTATTGTGCGAGAAACAATGTTGCTATGGGT<br>TATACTATGGACGTCTGGGGCCAAGGGACAATGGTCACC<br>GTCTCTTCAGGTGGAGGCGGTTCAGGCGGAGGTGGCTCT |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | GGCGGTGGCGGATCGCAGTCTGCCCTGACTCAGCCTGCC<br>TCCGCGTCCGGGTCTCCTGGACAGTCAGTCACCATCTCC<br>TGCACTGGAACCAGCAGTGACGTTGGTGGTTATAACTAT<br>GTCTCCTGGTACCAACAGCACCCAGGCAAAACCCCCAAA<br>CTCTTGATTTATGAGGTCAGTAGTCGGCCCTCAGGGGTT<br>TCTAATCGCTTCTCTGGCTCCAAGCCTGGCAACACGGCC<br>TCCCTGACCATCTCTGGTCTCCAGGCTGAGGACGAGGCT<br>GATTATTACTGCATCTCATATACAAGCAGCAACACTTGG<br>GTGTTCGGCGGAGGGACCCAGCTCACCGTTTTAGGTGCG<br>GCCGCA [Seq ID 30] |
| | | | QVQLVQSGAEVKKPGASVKVSCKASGYTFTGYYMHWVRQ<br>APGQGLEWMGWINPNSGGTNYAQKFQGRVTMTRDTSIGT<br>VYMELSSLTSDDTAMYYCARNNVAMGYTMDVWGQGTMVT<br>VSSGGGGSGGGGSGGGGSQSALTQPASASGSPGQSVTIS<br>CTGTSSDVGGYNYVSWYQQHPGKTPKLLIYEVSSRPSGV<br>SNRFSGSKPGNTASLTISGLQAEDEADYYCISYTSSNTW<br>VFGGGTQLTVLGAAA [Seq ID 31] |
| ME2 | MUC1 | scFvEC23 | GAGGTGCAGCTGTTGCAGTCTGGGGCGGAGGTGAAGAAG<br>CCTGGGGCCTCAGTGAAGGTCTCCTGCAAGGCTTCTGGA<br>TACACCTTCACCGGCTACTATATGCACTGGGTGCGACAG<br>GCCCCTGGACAAGGGCTTGAGTGGATGGGATGGATCAAC<br>CCTAACAGTGGTGGCACAAACTATGCACAGAAGTTTCAG<br>GGCAGAGTCACCATGACCAGGAACACCTCCATAAGCACA<br>GCCTACATGGAGCTGAGCAGCCTGAGATCTGAGGACACG<br>GCCGTGTATTACTGTGCGGGTCAGGAGGCACATGGGGAC<br>GGTATGGACGTCTGGGGCCAAGGGACCACGGTCACCGTC<br>TCCTCGGTGGAGCGAGGTGGCTCTGGCGGTGGCGGATCG<br>CAGTCTGCCCTGACTCAGCCTGCCTCCGCGTCCGGGTCT<br>CCTGGACAGTCGATCACCATCTCCTGCACTGGAACCAGC<br>GGTGACGTTGGTGGTTATAACTATGTCTCCTGGTACCAA<br>CAGCACCCAGGCAAAGCCCCCAAACTCATGATTTATGAA<br>GTCAGTAATCGGCCCTCAGGGGTTTCTAATCGCTTCTCT<br>GGCTCCAAGTCTGGCAGCACGGCCTCCCTGACCATCTCT<br>GGGCTCCAGGCTGAGGACGAGGCTGATTATTACTGCGTC<br>TCATATACAAGCAGAAACACTTATGTCTTCGGATCCGGG<br>ACCCAGCTCACCGTTTTAGGTGCGGCCGCGA [Seq ID 32] |
| | | | EVQLLQSGAEVKKPGASVKVSCKASGYTFTGYYMHWVRQ<br>APGQGLEWMGWINPNSGGTNYAQKFQGRVTMTRNTSIST<br>AYMELSSLRSEDTAVYYCAGQEAHGDGMDVWGQGTTVTV<br>SSVERGGSGGGGSQSALTQPASASGSPGQSITISCTGTS<br>GDVGGYNYVSWYQQHPGKAPKLMIYEVSNRPSGVSNRFS<br>GSKSGSTASLTISGLQAEDEADYYCVSYTSRNTYVFGSG<br>TQLTVLGAAA [Seq ID 33] |
| MB5 | MUC1 | mixTIL | GAGGTGCAGCTGGTGGAGTCTGGAGCTGAGGTGAAGAAG<br>CCCGGGGCCTCAGTGAAGGTCTCCTGCAAGGCTTCTGGA<br>TACACCTTCACCGCCTCCTATATGCACTGGGTGCGACAG<br>GCCCCTGGACAAGGGCTTGAGTGGATGGGATGGTTCAAC<br>CCTAATAGTGGTGGCACAAACTATGCACAGAAGTTTCAG<br>GGCAGGGTCACCATGACCGGGGACACGTCCACCAGCACA<br>GGCTATATGGAGCTGAGCAGGCTGACATCTGACGACGCG<br>NCCGTGTATTATTGTGCGAGAGATCGGGCCTCTGCTATG<br>GGCGTCTGGGGCCAAGGCACCCTGGTCACCGTCTCCTCA<br>GGTGGAGGCGGTTCAGGCGGAGGTGGCTCTGGCGGNGGC<br>CGATCGCAGTCTGCCCTGACTCAGCCTGCCTCCGCGTCC<br>GGGTCTCCTGGACAGTCAGTCACCATCTCCTGCACTGGA<br>ACCAGCAGTGACGTTGGTGGTTATAACTATGTCTCCTGG<br>TACCAACAGCACCCAGGCAAAGCCCCCAAACTCATGATT<br>TATGACGTCAATAAGCGGCCCTCAGGGGTCCCTGATCGC<br>TTCTCTGGCTCCAAGTCTGGCAACACGGCCTCCCTGACC<br>GTCTCTGGGCTCCAGGCTGAGGATGAGGCTGATTATTAC<br>TGCAGCTCATATGCAGGTAGTAACACTTTCCTATTCGGC<br>GGAGGGACCCAGCTCACCGTTTTAGGTGCGGCCGCA<br>[Seq ID 2] |
| | | | EVQLVESGAEVKKPGASVKVSCKASGYTFTASYMHWVRQ<br>APGQGLEWMGWFNPNSGGTNYAQKFQGRVTMTGDTSTST<br>GYMELSRLTSDDATVYYCARDRASAMGVWGQGTLVTVSS<br>GGGGSGGGGSGGGGSQSALTQPASASGSPGQSVTISCTG |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | TSSDVGGYNYVSWYQQHPGKAPKLMIYDVNKRPSGVPDR<br>FSGSKSGNTASLTVSGLQAEDEADYYCSSYAGSNTFLFG<br>GGTQLTVLGAAA [Seq ID 3] |
| MB5/ C'1 | MUC1 | maturation library based on MB5 clone, as described in Example 3 | ATGGAGGAGGTGCAGCTGCAGGAGTCTGGAGCTGAGGTG<br>AAGAAGCCCGGGGCCTCAGTGAAGGTCTCCTGCAAGGCT<br>TCTGGATACACCTTCACCGCCTCCTATATGCACTGGGTG<br>CGACAGGCCCCTGGACAAGGGCTTGAGTGGATGGGATGG<br>TTCAACCCTAATAGTGGTGGCACAAACTATGCACAGAAG<br>TTTCAGGGCAGGGTCACCATGACCGGGGACACGTCCACC<br>AGCACAGGCTATATGGAGCTGAGCAGGCTGACATCTGAC<br>GACGCGGCCGTGTATTATTGTGCGAGAGATCGGGCCTCT<br>GCTATGGGCGTCTGGGGCCAAGGAACCCTGGTCACCGTC<br>TCCTCAGGTGGAGGCGGTTCAGGCGGAGGTGGCTCTGGC<br>GGTGGCGGATCCCAGTCTGCCCTGACTCAGCCTGCCTCC<br>GTGTCTGGGTCTCCTGGACAGTCGATCACCATCTCCTGC<br>ACTGGAACCAGCAGTGACGTTGGTGGTTATAACTATGTC<br>TCCTGGTACCAACAGCACCCAGGCAAAGCCCCCAAACTC<br>ATGATTTATGATGTCAGTCATCGGCCCTCAGGGATTTCT<br>AATCGCTTCTCTGGCTCCAAGTCTGGCAACACGGCCTCC<br>CTGACCATCTCTAGGCTCCAGGCTGAGGACGAGGCTGAT<br>TATTACTGCAGCTCATATACAAGCAGTAACACTTTCATC<br>TTCGGAACTGGGACCCAGCTCACCGTTTTAGGTGCGGCC<br>GC [Seq ID 4] |
| | | | MEEVQLQESGAEVKKPGASVKVSCKASGYTFTASYMHWV<br>RQAPGQGLEWMGWFNPNSGGTNYAQKFQGRVTMTGDTST<br>STGYMELSRLTSDDAAVYYCARDRASAMGVWGQGTLVTV<br>SSGGGGSGGGGSGGGGSQSALTQPASVSGSPGQSITISC<br>TGTSSDVGGYNYVSWYQQHPGKAPKLMIYDVSHRPSGIS<br>NRFSGSKSGNTASLTISRLQAEDEADYYCSSYTSSNTFI<br>FGTGTQLTVLGAA [Seq ID 5] |
| MB5/ C'3 | MUC1 | maturation library based on MB5 clone, as described in Example 3 | ATGGAGCAGGTGCAGCTGGTGCAGTCTGGAGCTGAGGTG<br>AAGAAGCCCGGGGCCTCAGTGAAGGTCTCCTGCAAGGCC<br>TCTGGATACACCTTCACCGCCTCCTATATGCACTGGGTG<br>CGACAGGCCCCTGGACAAGGGCTTGAGTGGATGGGATGG<br>TTCAACCCTAATAGTGGTGGCACAAACTATGCACAGAAG<br>TTTCAGGGCAGGGTCACCATGACCGGGGACACGTCCACC<br>AGCACAGGCTATATGGAGCTGAGCAGGCTGACATCTGAC<br>GACGCGGCCGTGTATTATTGTGCGAGAGATCGGGCCTCT<br>GCTATGGGCGTCTGGGGCCAAGGCACCCTGGTCACCGTC<br>TCCTCAGGTGGAGGCGGTTCAGGCGGAGGCGGCTCTGGC<br>CGTGGCGGATCGCAGTCTGCCCTGACTCAGCCTGCCTCC<br>GTGTCTGGGTCTCCTGGACAGTCGATCACCATCTCCTGC<br>ACTGGAACCAGCAGTGACGTTGGTGGTTATAACTATGTC<br>TCCTGGTACCAACAGCACCCAGGCAAAGCCCCCAAACTC<br>ATGATTTATGATGTCACTAATCGGCCTTCAGGGGTTTCT<br>AGTCGCTTCTCTGGCTCCAAGTCTGGCAACACGGCCTCC<br>CTGACCATCTCTGGACTCCAGACTGAGGACGAGGCTGAT<br>TATTACTGCAACTCATTTACAAGCAGCAACACTTATGTC<br>TTCGGAACTGGGACCCAGCTCACCGTTTTAGGTGCGGCC<br>GC [Seq ID 6] |
| | | | MEQVQLVQSGAEVKKPGASVKVSCKASGYTFTASYMHWV<br>RQAPGQGLEWMGWFNPNSGGTNYAQKFQGRVTMTGDTST<br>STGYMELSRLTSDDAAVYYCARDRASAMGVWGQGTLVTV<br>SSGGGGSGGGGSGGGGSQSALTQPASVSGSPGQSITISC<br>TGTSSDVGGYNYVSWYQQHPGKAPKLMIYDVTNRPSGVS<br>SRFSGSKSGNTASLTISGLQTEDEADYYCNSFTSSNTYV<br>FGTGTQLTVLGAA [Seq ID 7] |
| CB3 | CEA | mixTIL | GAGGTGCAGCTGTTGCAGTCTGGGGCTGAGGTGAAGAAG<br>CCTGGGGCCTCAGTGAAGGTCTCCTGCAAGGCTTCTGGA<br>TACACCTTCACCGGCTCCTATATTCACTGGGTGCGACAG<br>GCCCCTGGACAAGGGCTTGAGTGGATGGGACGGATGAAC<br>CCTAACAGTGGTGACACAAACTATGCACAGAAGTTTCAG<br>GGCCGGGTCACCATGACCAGGGACACGTCCATCAGCACA<br>GCCTACATGGAGCTGAGCAGGCTGAGATCTGACGACACG<br>GCCGTGTACTACTGTGCGACGGAGGGAGTGGCTTTACGT<br>CCCGGTGCTTTTGATTTCTGGGGCCAAGGGACCCAGCTC<br>ACCGTTTTAGGTGCGGCCGCA [Seq ID 34] |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | EVQLLQSGAEVKKPGASVKVSCKASGYTFTGSYIHWVRQ<br>APGQGLEWMGRMNPNSGDTNYAQKFQGRVTMTRDTSIST<br>AYMELSRLRSDDTAVYYCATEGVALRPGAFDFWGQGTQL<br>TVLGAAA [Seq ID 35] |
| CB37 | CEA | mixTIL | GAGGAGGTGCAGCTGGTGCAGTCTGGAGGAGGCTTGATC<br>CAGCCGGGGGGGTCCCTGAGACTCTCTTGTGTAGCCTCT<br>GAGTTCAACGTCAGAAGCAACTACATGAGCTGGGTCCGC<br>CAGGCTCCAGGGAAGGGGCTGGAGTGGGTCTCAGTTATG<br>TATGACGGCGGTAGTACATACTACGCAGACTCCGTGAAG<br>GGCCGATTCACCATCTCCAGAGACAATTCTAAGAACACG<br>GTGTATCTTCAAATGAACAGCCTGAGAGCCGAGGACACG<br>GCCGTCTATTACTGTGCGAGAGGCGGATTGGGGTTGCCT<br>ACAATCGCGTCTTGGGAGATCTGGGGCCAAGGGACAATG<br>GTCACCGTCTCTTCAGGTGGAGGCGGTTCTGGCGGAGGT<br>GGCTCTGGCGGTGGCGGATCGTCCTATGTGCTGACTCAG<br>CCACCCTCGGTGTCAGTGGCCCCAGGAAAGACGGCCACG<br>ATTACCTGTGCGGGAAACAATATAGGAAGTAACAGTGTA<br>TACTGGTACCAGCAGAAACCAGGCCTGGCCCCTGTACTG<br>GTCGTCTATGATGATAGAGACCGGCCCTCAGGGATCCCT<br>GAGCGATTCTCTGGCTCCAAATCCGGGAACACGGCCACC<br>CTGACCATCAGCAGGGTCGAGGCCGGGGATCAGGCCGAC<br>TATTCTTGTCAGGTGTGGGATCCTAGTAGTGATCACCTC<br>TATGTCTTCGGAACTGGGACCCAGCTCACCGTTTTAGGT<br>GCGGCCGCA [Seq ID 8] |
| | | | EEVQLVQSGGGLIQPGGSLRLSCVASEFNVRSNYMSWVR<br>QAPGKGLEWVSVMYDGGSTYYADSVKGRFTISRDNSKNT<br>VYLQMNSLRAEDTAVYYCARGGLGLPTIASWEIWGQGTM<br>VTVSSGGGGSGGGGSGGGGSSYVLTQPPSVSVAPGKTAT<br>ITCAGNNIGSNSVYWYQQKPGLAPVLVVYDDRDRPSGIP<br>ERFSGSKSGNTATLTISRVEAGDEADYSCQVWDPSSDHL<br>YVFGTGTQLTVLGAAA [Seq ID 9] |
| CB40 | CEA | mixTIL | =CB37 |
| CB41 | CEA | mixTIL | GAGGAGGTGCAGCTGGTGGAGTCTGGGGGAGGCTTGGTC<br>CAGCCTGGGGGGTCCCTGAGACTCTCCTGTGCAGCCTCT<br>GGATTCACCGTCAGTAGCAACTACATGAGCTGGGTCCGC<br>CAGGCTCCAGGGAAGGGGCTGGAGTGGGTCTCAGTTGTT<br>TATAGCGGTGGTAGCACATACTACGCAGACTCCGTGAAG<br>GGCCGATTCACCATCTCCAGAGACAATTCCAAGAACACG<br>CTGTATCTTCAAATGAACAGCCTGAGAGCTGAGGACACG<br>GCTGTGTATTACTGTGCGACAGACCTAGGGGGGACTACA<br>GTTTGGCGCTACTACGGTATGGACGTCTGGGGCCAAGGG<br>ACCACGGTCACCGTCTCCTCAGGTGGAGGCGGTTCAGGC<br>GGAGGTGGCTCTGGCGGTGGCGGATCGTCCTATGTGCTG<br>ACTCAGCCACCCTCGGTGTCAGTGGCCCCAGGAAAGACG<br>GCCACGATTACCTGTGCGGGAAACAATATAGGAAGTAAC<br>AGTGTATACTGGTACCAGCAGAAACCAGGCCTGGCCCCT<br>GTACTGGTCGTCTATGATGATAGAGACCGGCCCTCAGGG<br>ATCCCTGGGCGATTCTCTGGCTCCAAATCCGGGAACACG<br>GCCACCCTGACCATCAGCAGGGTCGAGGCCGGGGATGAG<br>GCCGACTATTCTTGTCAGGTGTGGGATCCTAGTAGTGAT<br>CACCTCTATGTCTTCGGAACTGGGACCCAGCTCACCGTT<br>TTAGGTGCGGCCGCA [Seq ID 36] |
| | | | EEVQLVESGGGLVQPGGSLRLSCAASGFTVSSNYMSWVR<br>QAPGKGLEWVSVVYSGGSTYYADSVKGRFTISRDNSKNT<br>LYLQMNSLRAEDTAVYYCARDLGGTTVWRYYGMDVWGQG<br>TTVTVSSGGGGSGGGGSGGGGSSYVLTQPPSVSVAPGKT<br>ATITCAGNNIGSNSVYWYQQKPGLAPVLVVYDDRDRPSG<br>IPGRFSGSKSGNTATLTISRVEAGDEADYSCQVWDPSSD<br>HLYVFGTGTQLTVLGAAA [Seq ID 37] |
| CB53 | CEA | mixTIL | GAGGAGGTGCAGCTGGTGGAGTCTGGAGGAGACTTGATC<br>CAGCCTGGGGGGTCCCTGAGACTCTCCTGTGCAGCCTCT<br>GGGTTTACCGTCGGTAGCAACTACATGAGCTGGGTCCGC<br>CAGGCTCCAGGGAAGGGGCTGGAATGGGTCTCAGTTATT<br>TATAGCGGTGGTAGTACATACTACGCAGACTCCGTGAAG<br>GGCCGATTCACCATCTCCAGAGACAATTCCAAGAACACG<br>CTGTATCTTCAAATGAACAGCCTGAGAGCCGAGGACACG<br>GCCGTGTATTACTGTGTGAGAGATAGGGGTGATGCTTTT |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | GATATCTGGGGCCAAGGGACAATGGTCACCGTCTCTTCA<br>GGTGGAGGCGTTCCAGGCGGAGGTGGCTCTGGCGGTGGC<br>GGATCGTCCTATGCGCTGACTCAGCCACCCTCGGTGTCA<br>GTGGCCCCAGGAAAGACGGCCACGATTACCTGTGCGGGA<br>AACAATATAGGAAGTAACAGTGTATACTGGTACCAGCAG<br>AAACCAGGCCTGGCCCCTGTACTGGTCGTCTATGATGAT<br>AGCGACCGGCCCTCAGGGATGTCTGAGCGATTCTCTGGC<br>TCCAAATCCGGGAACACGGCCACCCTGACCATCAGCAGG<br>GTCGAGGCCGGGGATGAGGCCGACTATTCTTGTCAGGTG<br>TGGGATCCTAGTAGTGATCACCTCTATGTCTTCGGAACT<br>GGGACCCAGCTCACCGTTTTAGGTGCGGCCGCA [Seq ID 38]<br><br>EEVQLVESGGDLIQPGGSLRLSCAASGFTVGSNYMSWVR<br>QAPGKGLEWVSVIYSGGSTYYADSVKGRFTISRDNSKNT<br>LYLQMNSLRAEDTAVYYCVRDRGDAFDIWGQGTMVTVSS<br>GGGVPGGGGSGGGGSSYALTQPPSVSVAPGKTATITCAG<br>NNIGSNSVYWYQQKPGLAPVLVVYDDSDRPSGMSERFSG<br>SKSGNTATLTISRVEAGDEADYSCQVWDPSSDHLYVFGT<br>GTQLTVLGAAA [Seq ID 39] |
| CB60 | CEA | mixTIL | =CB41 |
| CB37/ 3B | CEA | maturation library based on CB37 clone, as described in Example 3. | ATGGAGGAGGTGCAGCTGGTGCAGTCTGGAGGAGGCTTG<br>ATCCAGCCGGGGGGGTCCCTGAGACTCTCTTGTGTAGCC<br>TCTGAGTTCAACGTCAGAAGCAACTACATGAGCTGGGTC<br>CGCCAGGCTCCAGGGAAGGGGCTGGAGTGGGTCTCAGTT<br>ATGTATGACGGCGGTAGTACATACTACGCAGACTCCGTG<br>AAGGGGCGATTCACCATCTCCAGAGACAATTCTAAGAAC<br>ACGGTGTATCTTCAAATGAACAGCCTGAGAGCCGAGGAC<br>ACGGCCGTCTATTACTGTGCGAGAGGCGGATTGGGGTTG<br>CCTACAATCGCGCCTTGGGAGATCTGGGGCCAAGGGACA<br>ATGGTCACCGTCTCTTCAGGTGGAGGCGGTTCAGGCGGA<br>GGTGGCTCTGGCGGTGGCGGATCGTCCTATGTGCTGACT<br>CAGCCACCCTCGGTGTCAGTGGCCCCAGGAAAGACGGCC<br>ACGATTACCTGTGCGGGAAACAATATAGGAAGTAACAGT<br>GTATACTGGTACCAACAAAAACCAGGCCTGGCCCCTGTA<br>CTGGTCGTCTATGATGATAGAGACCGGCCCTCAGGGATC<br>CATGAGCGATTCTCTGGCTCCAAATCCGGGAACACGGCC<br>ACCCTGACCATCAGCAGGGTCGAGGCCGGGGATGAGGCC<br>GACTATTCTTGTCAGGTGTGGGATCCTAGTAGTGATCAC<br>CTCTATGTCTTCGGAACTGGGACCCAGCTCACCGTTTTA<br>GGTGCGGCCGC [Seq ID 10]<br><br>MEEVQLVQSGGGLIQPGGSLRLSCVASEFNVRSNYMSWV<br>RQAPGKGLEWVSVMYDGGSTYYADSVKGRFTISRDNSKN<br>TVYLQMNSLRAEDTAVYYCARGGLGLPTIAPWEIWGQGT<br>MVTVSSGGGGSGGGGSGGGGSSYVLTQPPSVSVAPGKTA<br>TITCAGNNIGSNSVYWYQQKPGLAPVLVVYDDRDRPSGI<br>HERFSGSKSGNTATLTISRVEAGDEADYSCQVWDPSSDH<br>LYVFGTGTQLTVLGAA [Seq ID 11] |
| CB37/ 9C | CEA | maturation library basedon CB37 clone,as described inExample 3. | ATGGAGGAGGTGCAGCTGGTGCAGTCTGGAGGAGGCTTG<br>ATCCAGCCGGGGGGGTCCCTGAGACTCTCTTGTGTAGCC<br>TCTGAGTTCAACGTCAGAAGCAACTACATGAGCTGGGTC<br>CGCCAGGCTCCAGGGAAGGGGCTGGAGTGGGTCTCAGTT<br>ATGTATGACGGCGGTAGTACATACTACGCAGACTCCGTG<br>AAGGGCCGATTCACCATCTCCAGAGACAATTCTAAGAAC<br>ACGGTGTATCTTCAAATGAACAGCCTGAGAGCCGAGGAC<br>ACGGCCGTCTATTACTGTGCGAGAGGCGGATTGGGGTTG<br>CCTACAATCGCGTCTTGGGAGATCTGGGGCCAAGGGACA<br>ATGGTCACCGTCTCTTCAGGTGGAGGCGGTTCAGGCGGA<br>GGTGGCTCTGGCGGTGGCGGATCGTCCTATGTGCTGACT<br>CAGCCACCCTCGGTGTCAGTGGCCCCAGGAAAGACGGCC<br>ACGATTACCTGTGCGGGAAACAATATAGGAAGTAACAGT<br>GTATACTGGTACCAGCAGAAACCAGGCCTGGCCCCTGTA<br>CTGGTCGTCTATGATGATAGAGACCGGCCCTCAGGGCTC<br>CCCGGGCGATTCTCTGGCTCCAAATCCGGGAACACGGCC<br>ACCCTGACCATCAGCAGGGTCGAGGCCGGGGATGAGGCC<br>GACTATTCTTGTCAGGTGTGGGATCCTAGTAGTGATCAC<br>CTCTATGTCTTCGGAACTGGGACCCAGCTCACCGTTTTA<br>GGTGCGGCCGC [Seq ID 12] |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | MEEVQLVQSGGGLIQPGGSLRLSCVASEFNVRSNYMSWV<br>RQAPGKGLEWVSVMYDGGSTYYADSVKGRFTISRDNSEN<br>TVYLQMNSLRAEDTAVYYCARGGLGLPTIASWEIWGQGT<br>MVTVSSGGGGSGGGGSGGGGSSYVLTQPPSVSVAPGKTA<br>TITCAGNNIGSNSVYWYQQKPGLAPVLVVYDDRDRPSGL<br>PGRFSGSKSGNTATLTISRVEAGDEADYSCQVWDPSSDH<br>LYVFGTGTQLTVLGAA [Seq ID 13] |
| anti-SP2 | SP2 | scFvEC23 | ATGGAGGAGGTGCAGCTGGTGGAGTCTGGGGGAGCCTTG<br>GTACAGCCTGGGGGGTCCCTGAGAATCTCTTGTGTAGGC<br>TCTGGATTCACCTTCCGACAGCATGACATGAGCTGGGTC<br>CGCCAGGCTCCTGGGAAGGGGCTGGAGTGGGTCGCAACT<br>ATAAGTGGAAGTGCTGATAACACATTTTACGCAGACTCC<br>GTGAAGGGCCGGTTCACCATCTCCAGAGACAATTCCAAG<br>AACACGCTGTATCTGCAGATGAACACCCTGAAAGCCGAC<br>GACACGGCCGTATATTACTGTGCGAAGAAATATATAGAA<br>CCAGGTGCTACCCGATTTGACTACTGGGGCCAGAGAACC<br>CTGGTCACCGTCTCCTCAGGTGGAGGCGGTTCAGGCGGA<br>GGTGGCTCTGGCGGTGGCGGATCGGATGTTGTGATGACT<br>CAGTCTCCACTCTCTCTGTCCGTCACCCCTGGACAGCCG<br>GCCTCCATCTCCTGCAAGTCTAGTCAGAGCCTCCTGCAT<br>AGTGATGGAAAGACCTATTTGTATTGGTACCTGCAGAAG<br>CCAGGCCAGTCTCCACAGCTCCTGATCTATGAAGTTTCC<br>AACCGGTTCTCTGGAGTGCCAGATAGGTTCAGTGGCAGC<br>GGGTCAGGGACAGATTTCACACTGAAAATCAGCCGGGTG<br>GAGGCTGAGGATGTTGGGGTTTATTACTGCATGCAAAGT<br>ATACAGCTCCCGATCACCTTCGGCCAAGGGACACGACTG<br>GAGATTAAACGTGCGGCCGC [Seq ID 40]<br><br>MEEVQLVESGGALVQPGGSLRISCVGSGFTFRQHDMSWV<br>RQAPGKGLEWVATISGSADNTFYADSVKGRFTISRDNSK<br>NTLYLQMNTLKADDTAVYYCAKKYIEPGATRFDYWGQRT<br>LVTVSSGGGGSGGGGSGGGGSDVVMTQSPLSLSVTPGQP<br>ASISCKSSQSLLHSDGKTYLYWYLQKPGQSPQLLIYEVS<br>NRFSGVPDRFSGSGSGTDFTLKISRVEAEDVGVYYCMQS<br>IQLPITFGQGTRLEIKRAA [Seq ID 41] |
| mix7 | MCF7 cells | mixLIB | GAGCAGGTGCAGCTGGTGCAGTCTGGGGCGGAGGTGAAG<br>AAGCCTGGGGCCTCAGTGAGAGTTTCCTGCCAGGCATCT<br>GGATACACATTCAGCAGGTACCATATGCACTGGGTGCGA<br>CAGGCCCCTGGACAAGGGCTTGAGTGGATGGGAGTGATC<br>GACCCCAATAGTGGTAGAGTAAGTTACTCACAGAAGTTC<br>CAGGACAGAGTTACCATGACCAGGGACACGTCCACGAGC<br>ACAGTATACATGGAGCTGAACAGCCCGAGATCTGAGGAC<br>ACGGCCGTTTATTATTGTGCGAGAGATCGAGGATATTGT<br>AATGGTGGCAGGTGCTTTATGGATGCATTTGACTACTGG<br>GGCCAGGGGACAATGGTCACCGTCTCTTCAGGTGGAGGC<br>GGTTTAGGCGGAGGTGGCTCTGGCGGTGGCGGATCGTCC<br>TATGTGCTGACTCACCCACCCTCATTGTCTGGGGCCCCA<br>GGGCAGAGCATCACCATCTCCTGCACTGGGAGCAGTTCC<br>AACATCGGGGCAGGTTTTCATATACACTGGTACCAGCAG<br>TTTCCAAAAACAGCCCCCAAACTCCTTATCTATGGTAGT<br>AGTAATCGACCCTCAGGGGTCCCTGACCGCTTCTCTGGC<br>TCCAGGTCTGGCTCCTCAGGCTCCCTGGCCATCACTGGG<br>CTCCAGGCAGACGATGAGGCTGATTATTACTGTGTGGGA<br>TGGGATGGCAGCCTGAGTGGTTATGTCTTCGGAACTGGG<br>ACCCAGCTCACCGTTTTAGGTGCGGCCGCA [Seq ID 16]<br><br>EQVQLVQSGAEVKKPGASVRVSCQASGYTFSRYHMHWVR<br>QAPGQGLEWMGVIDPNSGRVSYSQKFQDRVTMTRDTSTS<br>TVYMELNSPRSEDTAVYYCARDRGYCNGGRCFMDAFDYW<br>GQGTMVTVSSGGGGLGGGGSGGGGSSYVLTHPPSLSGAP<br>GQSITTSCTGSSSNIGAGFHIHWYQQFPKTAPKLLIYGS<br>SNRPSGVPDRFSGSRSGSSGSLAITGLQADDEADYYCVG<br>WDGSLSGYVFGTGTQLTVLGAAA [Seq ID 17] |
| mix8 | MCF7 cells | mixLIB | GAGCAGGTGCAGCTGGTGCAGTCTGGGGGAGGCGTGGTC<br>CAGCCTGGGAGGTCCCTGAGACTCTCCTGTGCAGCCTCT<br>GGATTCAGCTTCAGTAACTATGTTATGCACTGGGTCCGC<br>CAGGCTCCAGGCAAGGGGCTGGAGTGGGTGGCAGTTATA<br>TCACATGATGGAAGCAATAAATACTACGCAGACTCCGTG<br>AAGGGCCGATTCACCATCTCCAGAGACAATTCCAAGAAC<br>ACGCTATATCTGCAAATGAAAAGCCTGAGACCTGAGGAC |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | ACGGCTGTGTATTACTGTGCGAGAAGTAGTGGCTGGTAC<br>CTTCTCTTTGATGCTTTTGATATCTGGGGCCAAGGGACA<br>ATGGTCACCGTCTCTTCAGGTGGAGGCGGTTCAGGCGGA<br>GGTGGCTCTGGCGGTGGCGGATCGGACATCCAGATGACC<br>CAGTCTCCAGACTCCCTGCCTGTGTCTCTGGGCGAGAGG<br>GCCACCATCAACTGCAGGTCCAGCCAGAGTGTTTTATAC<br>AGCTCCAACAATAAGAACTACTTAGCTTGGTACCAGCAG<br>AAACCAGGACAGCCTCCTAAGCTGCTCATTTACTGGGCA<br>TCTACCCGGGAATCCGGTGTCCCTGACCGATTCAGTGGC<br>AGCGGGTCTGGGACAGATTTCACTCTCACCATCAGCAGC<br>CTGCAGGCTGAAGATGTGGCAGTTTATTACTGTCAGCAA<br>TATTATAGGATTCCGTGGACGTTCGGCCAAGGGACGAAG<br>GTGGAAATCAAACGTGCGGCCGCA [Seq ID 42] |
| | | | EQVQLVQSGGGVVQPGRSLRLSCAASGFSFSNYVMHWVR<br>QAPGKGLEWVAVISHDGSNKYYADSVKGRFTISRDNSEN<br>TLYLQMKSLRPEDTAVYYCARSSGWYLLFDAFDIWGQGT<br>MVTVSSGGGGSGGGGSGGGGSDIQMTQSPDSLPVSLGER<br>ATINCRSSQSVLYSSNNKNYLAWYQQKPGQPPKLLIYWA<br>STRESGVPDRFSGSGSGTDFTLTISSLQAEDVAVYYCQQ<br>YYRIPWTFGQGTKVEIKRAAA [Seq ID 43] |
| mix11 | MCF7 cells | mixLIB | GAGGAGGTGCAGCTGTTGCAGTCTGGGGGAGGTGTGGTA<br>CGGCCTGGGGGGTCCCTGAGACTCTCCTGTGCAGCCTCT<br>GGATTCACCTTTGATGATTATGGCATGACCTGGGTCCGC<br>CAGGCTCCAGGGAAGGGGCTGGAGTGGGTCTCAGCTATT<br>AGTGGTAGTGGTGGTAGCACATACTACGCAGACTCCGTG<br>AAGGGCCGGTTCGCCATCTCCAGAGACAATTCCAAGAAC<br>ACGCTGTATCTGCAAATGAACAGCCTGAGAGCCGAGGAC<br>ACGGCCGTATATTACTGTGCGAAATCTCGCTACTATGAT<br>AGTAGTGGTTATTACTACACCGTGCGACCTGATGCTTTT<br>GATATCTGGGGCCAAGGGGCAATGGTCACCGTCTCTTCA<br>GGTGGAGGCGGTGGAGGTGGCTCTGGCGGTGGCGGATCG<br>TCTTCTGAGCTGACTCAACCACCCTCAGTGTCCGTGTCC<br>CCAGGACAGACAGCCATCATCACCTGCTCTGGAGATAAA<br>TTGGGGGATAAATATGCTTCCTGGTATCAGCACAGGCCA<br>GGCCAGTCGCCTGTCTTGGTCATCTATCAGGATTCCAGG<br>CGGCCCTCAGACATCCCTGAGCGATTCTCTGGCTCCAAC<br>TCTGGGAACACAGCCACTCTGACCATCACCGAGGCCCAG<br>GCTTTGGATGAGGCTGACTATTATTGTCAGGCCTGGGCC<br>GGCAGATCTGTGGTCTTCGGCGGGGGGACCCAGCTCACC<br>GTTTTAGGTGCGGCCGCA [Seq ID 44] |
| | | | EEVQLLQSGGGVVRPGGSLRLSCAASGFTFDDYGMTWVR<br>QAPGKGLEWVSAISGSGGSTYYADSVKGRFAISRDNSEN<br>TLYLQMNSLRAEDTAVYYCAKSRYYDSSGYYYTVRPDAF<br>DIWGQGAMVTVSSGGGGGGSGGGGSSSELTQPPSVSVS<br>PGQTAIITCSGDKLGDKYASWYQHRPGQSPVLVIYQDSR<br>RPSDIPERFSGSNSGNTATLTITEAQALDEADYYCQAWA<br>GRSVVFGGGTQLTVLGAAA [Seq ID 45] |
| mix12 | MCF7 cells | mixLIB | GAGGAGGTGCAGCTGTTGCAGTCTGGGGCGGAGGTGAAG<br>AAGCCTGGGGCCTCAGTGAGAGTTTCCTGCCAGGCATCT<br>GGATACACATTCAGCAGGTACCATATGCACTGGGTGCGA<br>CAGGCCCCTGGACAAGGCCTTGAGTGGATGGGAGTGATC<br>GACCCCAATAGTGGTAGAGTAAGTTACTCACAGAAGTTC<br>CAGGACAGAGTCACCATGACCAGGGACACGTTCACGAGC<br>ACAGTATACATGGAGCTGAACAGCCTGAGATCTGAGGAC<br>ACGGCCGTTTATTATTGTGCGAGAGATCGAGGATATTGT<br>AATGGTGGCAGGTGCTTTATGGATGCATTTGACTACTGG<br>GGCCAGGGGACCACGGTCACCGTCTCCTCAGGTGGAGGC<br>GGTTCAGGCGGAGGTGGCCCTGGCGGTGGCGGATCGTCC<br>TATGTGCTGACTCAGCCACCCTCAGCGTCTGGGGCCCCC<br>GGACAGAGGGTCACCATCTCTTGTTCTGGAAGCAACTCC<br>AACATCGGACGTAATTGGGTATACTGGTACCAGCAACTC<br>CCAGGAACGGCCCCCAAACTCCTCATGTTTAGGAATAAT<br>GAACGGTCCTCAGGGGTCCCTGACCGATTCTCTGGCTCC<br>AAGACTGGCACCTCAGCCTCCCTGGCCATCAGTGGGCTC<br>CGGTCTGAGGATGAGGGTGATTACTACTGTGCATCATGG<br>GATGACAGTCTGCATGCTTGGGTGTTCGGCGGGGGGACC<br>CAGCTCACCGTTTTAGGTGCGGCCGCA [Seq ID 46] |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | EEVQLLQSGAEVKKPGASVRVSCQASGYTFSRYHMHWVR<br>QAPGQGLEWMGVIDPNSGRVSYSQKFQDRVTMTRDTFTS<br>TVYMELNSLRSEDTAVYYCARDRGYCNGGRCFMDAFDYW<br>GQGTTVTVSSGGGGSGGGGPGGGGSSYVLTQPPSASGAP<br>GQRVTISCSGSNSNIGRNWVYWYQQLPGTAPKLLMFRNN<br>ERSSGVPDRFSGSKTGTSASLAISGLRSEDEGDYYCASW<br>DDSLHAWVFGGGTQLTVLGAAA [Seq ID 47] |
| mix17 | MCF7 cells | mixLIB | GAGCAGGTGCAGCTGGTGCAGTCTGGGGGAGGCTTGGTA<br>CAGCCTGGGGGGTCCCTGAGACTCTCCTGTGCAGCCTCT<br>GGATTCACCTTTAGCAGCTATGCCATGAGCTGGGTCCGC<br>CAGGCTCCAGGGAAGGGGCTGGAGTGGGTCTCAGCTATT<br>AGTGGTAGTGGTGGTAGCACATACTACGCAGACTCCGTG<br>AAGGGCCGGTTCACCATCTCCAGAGAGAATTCCAAGAAC<br>ACGCTATATCTGCAAATGAATAGCCTGAGAGCCGAGGAC<br>ACGGCTGTGTATTACTGTGCGAGACAAACAAGAGTCCGT<br>GCTTTTGATATCTGGGGCCAAGGGACAATGGTCACCGTC<br>TCTTCAGGTGGAGGCGGTTCAGGCGGAGGTGGCTCTGGC<br>GGTGGCGGATCGGACATCCAGATGACCCAGTCTCCTTCC<br>GCCCTGTCTGCATCTGTAGGAGGCAGAGTCACCATCACT<br>TGCCGGGCAAGTCAGAGCACTAGTAGCGATTTAAATTGG<br>TATCAGCAAAGACCAGGGAAAGCCCCTAAACTCCTGATC<br>TCTGTTGCATCCACTTTACAAAGTGACGTCCCATCAAGG<br>TTCAGTGGCAGTGGTTCTGGGACAGATTTCAGTCTCACC<br>ATCAGCAGTCTGCAACCTGAAGACTTTGCAACTTACTTC<br>TGTCAACAGAGTTACAGCACCCCGTACACTTTTGGCCAG<br>GGGACCAAAGTGGATATCAAACGTGCGGCCGCA [Seq<br>ID 18]<br><br>EQVQLVQSGGGLVQPGGSLRLSCAASGFTFSSYAMSWVR<br>QAPGKGLEWVSAISGSGGSTYYADSVKGRFTISRENSEN<br>TLYLQMNSLRAEDTAVYYCARQTRVRAFDIWGQGTMVTV<br>SSGGGGSGGGGSGGGGSDIQMTQSPSALSASVGGRVTIT<br>CRASQSTSSDLNWYQQRPGKAPKLLISVASTLQSDVPSR<br>FSGSGSGTDFSLTISSLQPEDFATYFCQQSYSTPYTFGQ<br>GTKVDIKRAAA [Seq ID 19] |
| mix23 | MCF7 cells | mixLIB | GAGGAGGTGCAGCTGGTGGAGTCTGGGGGAAACTTGGTT<br>CAGCCTGGGGGGTCCCTGAGACTCTCCTGTGCAGCCTCT<br>GGATTCACCTTTAGCAGTTATGCCATGAGCTGGGTCCGC<br>CAGGCTCCAGGGAAGGGGCTGGAATGGGTCTCAGCTATT<br>AGTGCTAGTGGTGGCACCACATACTACGCAGATTCCGTG<br>AAGGGCCGGTTCACCATCTCCAGAGACAATTCCAAGAAC<br>ACGCTGTATCTTCAAATGAACAGCCTGAGAACTGAGGAC<br>ACGGCTGTGTATTACTGTGCGAGAGACAGCCGTGCATAC<br>AGCTATGGTTACCTCTACGTCTTTGACTACTGGGGCCAG<br>GGCACCCTGGTCACCGTCTCCTCAGGTGGAGGCGGTTCA<br>GGCGGAGGTGGCTCTGGCGGTGGCGGATCGCAGTCTGCC<br>CTGACTCAGCCTGCCTCCGTGTCTGGGTCTCCTGGACAG<br>TCGATCACCATCTCCTGCACTGGAACCAGCAATGATGTT<br>GGGAGTTATAACCTTGTCTCCTGGTACCAACAACACCCA<br>GGCAAAGCCCCCAAACTCCTGATTTATGAGGGCAGTAAG<br>CGGCCCTCAGGGATTTCTAATCGCTTCTCTGGCTCCAAG<br>TCTGGCAACACGGCCTCCCTGACCATCTCTGGGCTCCAG<br>GCTGAGGACGAGGCTGATTATTACTGCATGTCATATACG<br>AGCAGTGGCACTCCTTATGTCTTCGGAACTGGGACCCAG<br>CTCACCGTTTTAGGTGCGGCCGCA [Seq ID 48]<br><br>EEVQLVESGGNLVQPGGSLRLSCAASGFTFSSYAMSWVR<br>QAPGKGLEWVSAISASGGTTYYADSVKGRFTISRDNSEN<br>TLYLQMNSLRTEDTAVYYCARDSRAYSYGYLYVFDYWGQ<br>GTLVTVSSGGGGSGGGGSGGGGSQSALTQPASVSGSPGQ<br>SITISCTGTSNDVGSYNLVSWYQQHPGKAPKLLIYEGSK<br>RPSGISNRFSGSKSGNTASLTISGLQAEDEADYYCMSYT<br>SSGTPYVFGTGTQLTVLGAAA [Seq ID 49] |
| mix25 | MCF7 cells | mixLIB | GAGGAGGTGCAGCTGGTGGAGTCTGGGGCTGAGGTGAAG<br>AAGCCTGGGGCCTCAGTGAGAGTTTCCTGCCAGGCATCT<br>GGATACACATTCACCAGGTACCATATACACTGGGTGCGA<br>CAGGCCCCTGGACAAGGGCTTGAGTGGATGGGAGTGATC<br>GACCCCAATAGTGGTAGAATAAGTTACTCACAGAAGTTC<br>CAGGACAGAGTCACCATGACCAGGGACACGTCCACGAGC |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | ACAGTCTACATGGAGCTGAACAGCCTGAGATCTGAGGAC<br>ACAGCCATTTATTACTGTGCGAGAGATCGAGGATATTGT<br>AATGGTGGCAGGTGCTTTATGGATGCATTTGACTACTGG<br>GGCCAGGGGACCACGGTCACCGTCTCCTCAGGTGGAGGC<br>GGTTCAGGCGGAGGTGGCTCTGGCGGTGGCGGATCGCAG<br>TCTGTGTTGACGCAGCCGCCCTCAGCGTCTGGGACCCCC<br>GGGCAGAGGGTCACCATCGCTTGTTCTGGAAGCAGCTCC<br>AACATCGGAATTAATACTGTAAACTGGTACCAGCAGATC<br>CCAGGAACGGCCCCCAAACTCCTCATCTATAATAATGAT<br>CAGCGGCCCTCAGGGGTCCCTGACCGATTCTCTGGCTCC<br>AAGTCTGCCACCTCAGCCTCCCTGGCCATCACTGGGCTC<br>CAGGTTGACGATGAGGCTGATTATTACTGCCAGTCCTAT<br>GACAGCAGCCTGGGTGGTTATGTCTTCGGAACTGGGACC<br>CAGCTCACCGTTTTAGGTGCGCCCGCA [Seq ID 50] |
| | | | EEVQLVESGAEVKKPGASVRVSCQASGYTFTRYHIHWVR<br>QAPGQGLEWMGVIDPNSGRISYSQKFQDRVTMTRDTSTS<br>TVYMELNSLRSEDTAIYYCARDRGYCNGGRCFMDAFDYW<br>GQGTTVTVSSGGGGSGGGGSGGGGSQSVLTQPPSASGTP<br>GQRVTIACSGSSSNIGINTVNWYQQIPGTAPKLLIYNND<br>QRPSGVPDRFSGSKSATSASLAITGLQVDDEADYYCQSY<br>DSSLGGYVFGTGTQLTVLGAAA [Seq ID 51] |
| mix39 | MCF7 cells | mixLIB | GAGGAGGTGCAGCTGTTGCAGTCTGGGGGAGGCGTGGTC<br>CAGCCTGGGAGGTCCCTGAGACTCTCCTGTGCAGCCTCT<br>GGATTCAGCTTCAGTAACTATGTTATGCACTGGGTCCGC<br>CAGGCTCCAGGCAAGGGGCTGGAGTGGGTGGCAGTTATA<br>TCATATGATGGAAGCAATAAATACTACGCAGACTCCGTG<br>AAGGGCCGATTCACCATCTCCAGAGACAATTCCAAGAAC<br>ACGCTATATCTGCAAATGAAAGGCCTGAGACCTGAGGAC<br>ACGGCTGTGTATTACTGTGCGAGAAGTAGTGGCTGGTAC<br>CTTCTCTTTGATGCTTTTGATATCTGGGGCCAAGGGACA<br>ATGGTCACCGTCTCTTCAGGTGGAGGCGGTTCAGGCGGA<br>GGTGGCTCTGGCGGTGGCGGATCGGATGTTGTGATGACA<br>CAGTCTCCAGACTCCCTGGCTGTGTCGCTGGGCGAGAGG<br>GCCACCATCAACTGCGAGTCCAGCCAGAGTGTTTTATTC<br>AGCTCCAACAATAAGAACTACTTAGCTTGGTACCAGCAG<br>AAACCAGGACAGCCTCCTAAGCTGCTCATTTACTGGGCA<br>TCTACCCGGGAATCCGGGGTCCCTGACCGATTCAGTGGC<br>AGCGGGTCTGAGACAGATTTCACTCTCACCATCAGCAGC<br>CTGCAGGCTGAAGATGTGGCAGTTTATTACTGTCAGCAA<br>TATTATAGGATTCCGTGGACGTTCGGCCAAGGGACCAAA<br>GTGGATATCAAACGTGCGGCCGCA [Seq ID 20] |
| | | | EEVQLLQSGGGVVQPGRSLRLSCAASGFSFSNYVMHWVR<br>QAPGKGLEWVAVISYDGSNKYYADSVKGRFTISRDNSEN<br>TLYLQMKGLRPEDTAVYYCARSSGWYLLFDAFDIWGQGT<br>MVTVSSGGGGSGGGGSGGGGSDVVMTQSPDSLAVSLGER<br>ATINCESSQSVLFSSNNKNYLAWYQQKPGQPPKLLIYWA<br>STRESGVPDRFSGSGSETDFTLTISSLQAEDVAVYYCQQ<br>YYRIPWTFGQGTKVDIKRAAA [Seq ID 21] |
| B96/ 4F | MCF7 cells | scFvB96 | ATGGAGCAGGTGCAGCTGCAGGAGTCTGGGGGAGGCTTG<br>GTACAGCCTGGGGGGTCCCTGAGACTCTCCTGTGCAGCC<br>TCTGGATTCACCTTTAGTACTTATGCCATGAGCTGGGTC<br>CGCCAGGCTCCAGGGAAGGGGCTGGAGTGGGTCTCAGTT<br>ATTAGTGGTAGTGGTCATACAACAAACTACGCCGACTCC<br>GTGAAGGGCCGCGTCACCATATCCAGAGACAATTCCAAG<br>AACACACTATATCTGCAAATCAACAGCCTGAGAGCCGAC<br>GACACGGCCGTGTATTACTGTGCGAGAGATGTGTTAGTC<br>CTACAGAATGCTTTTGATATCTGGGGCCAAGGGACCACG<br>GTCACCGTCTCCTCAGGTGGAGGTGGTTCAGGCGGAGGT<br>GGCTCTGGCGGTGGCGGATCGGATGTTGTGATGACCCAG<br>TCTCCATCCTCACTGTCTGCATCTGTAGGAGACAGAGTC<br>ACCATCACTTGTCGGGCGAGTCAGGGTATTAGCAGGTGG<br>TTAGCCTGGTATCAACAGAAACCAGGGAAAGCCCCTAAG<br>CTCCTGATCTACGCTGCATCCAGTTTGCAAAGTGGGGTC<br>CCATCAAGGTTCAGTGGCAGTGGATCTGGGACAGATTTC<br>ACTCTCACCATCAGCAGTCTGCAACCTGAAGATTTTGCA<br>ACTTACATCTGTCAACAGAGTTACAGTAGGCCGCTCACT<br>TTCGGCGGAGGGACCAAGGTGGAAATCAAACGTGCGGCC<br>GCA [Seq ID 52] |

TABLE 5-continued

Selected antibodies. MixTIL and MixLIB are mixture of libraries defined in table 2.

| Anti-body | Anti-gen | Library used for selection | Nucleotide/Amino acid sequence |
|---|---|---|---|
| | | | MEQVQLQESGGGLVQPGGSLRLSCAASGFTFSTYAMSWV<br>RQAPGKGLEWVSVISGSGHTTNYADSVKGRVTISRDNSK<br>NTLYLQINSLRADDTAVYYCARDVLVLQNAFDIWGQGTT<br>VTVSSGGGGSGGGGSGGGGSDVVMTQSPSSLSASVGDRV<br>TITCRASQGISRWLAWYQQKPGKAPKLLIYAASSLQSGV<br>PSRFSGSGSGTDFTLTISSLQPEDFATYICQQSYSRPLT<br>FGGGTKVEIKRAAA [Seq ID 53] |
| B96/<br>11L | MCF7<br>cells | scFvB96 | GAGCAGGTGCAGCTGCAGGAGTCTGGGGGAGGCTTGGTA<br>CAGCCTGGGGGGTCCCTGAGACTCTCCTGTGCAGCCTCT<br>GGATTCACCTTTAGTACTTATGCCATGAGCTGGGTCCGC<br>CAGGCTCCAGGGAAGGGGCTGGAGTGGGTCTCAGTTATT<br>AGTGGTAGTGGTCATACAACAAACTACGCCGACTCCGTG<br>AAGGGCCGCGTCACCATATCCAGAGACAATTCCAAGAAC<br>ACACTATATCTGCAAATCAACAGCCTGAGAGCCGACGAC<br>ACGGCCGTGTATTACTGTGCGAGAGATGTGTTAGTCCTA<br>CAGAATGCTTTTGATATCTGGGGCCAAGGGACCACGGTC<br>ACCGTCTCCTCAGGTGGAGGTGGTTCAGGCGGAGGTGGC<br>TCTGGCGGTGGCGGATCGGATGTTGTGATGACCCAGTCT<br>CCATCCTCACTGTCTGCATCTGTAGGAGACAGAGTCACC<br>ATCACTTGTCGGGCGAGTCAGGGTATTAGCAGGTGGTTA<br>GCCTGGTATCAACAGAAACCAGGGAAAGCCCCTAAGCTC<br>CTGATCTACGCTGCATCCAGTTTGCAAAGTGGGGTCCCA<br>TCAAGGTTCAGTGGCAGTGGATCTGGGACAGATTTCACT<br>CTCACCATCAGCAGTCTGCAACCTGAAGATTTTGCAACT<br>TACATCTGTCAACAGAGTTACAGTAGGCCGCTCACTTTC<br>GGCGGAGGGACCAAGGTGGAAATCAAACGTGCGGCCGCA<br>[Seq ID 14]<br><br>EQVQLQESGGGLVQPGGSLRLSCAASGFTFSTYAMSWVR<br>QAPGKGLEWVSVISGSGHTTNYADSVKGRVTISRDNSEN<br>TLYLQINSLRADDTAVYYCARDVLVLQNAFDIWGQGTTV<br>TVSSGGGGSGGGGSGGGGSDVVMTQSPSSLSASVGDRVT<br>ITCRASQGISRWLAWYQQKPGKAPKLLIYAASSLQSGVP<br>SRFSGSGSGTDFTLTISSLQPEDFATYICQQSYSRPLTF<br>GGGTKVEIKRAAA [Seq ID 15] |

TABLE 6

Kinetic values of parental and affinity maturated single-chain antibodies. Parental anti-CEA antibody CB37 is not stable in soluble form. Maturated single-chain antibodies have nanomolar affinity. $K_a$ = association constant, $K_d$ = dissociation constant, KD = $K_a$/$K_d$, SE = standard error. Data are expressed in Molar.

| scFV | $k_a$ (+/−SE) | $k_d$ (+/−SE) | $K_D$ |
|---|---|---|---|
| MB5 | 2.13E+04 (2.45E+02) | 8.55E−03 (6.25E−05) | 4.01E−07 |
| MBB5/C'1 | 1.53E+05 (4.15E+02) | 1.45E−03 (1.29E−05) | 9.46E−09 |
| MB5/C'3 | 7.11E+04 (4.33E+02) | 1.64E−03 (2.46E−05) | 2.31E−08 |
| CB37 | — | — | — |
| CB37/3B | 1.27E+05 (9.79E+02) | 1.42E−04 (3.23E−05) | 3.66E−09 |
| CB37/9C | 1.00E+05 (5.75E+02) | 4.65E−04 (2.54E−05) | 1.42E−09 |

This study with Biacore provided quantitative measures of scFv-antigen binding and dissociation kinetics. Table 6 reports the kinetic values of the parental and affinity-maturated scFvs. The maturated antiMUC1 antibodies MB5/C'1 and MB5/C'3 have over 42 times and 17 times higher affinity to the antigen, compared to MB5, respectively. The maturated anti-CEA antibodies CB37/3B and CB37/9C have nanomolar affinity. Moreover, the maturated antibodies are more stable than original CB37, which was not reactive in soluble form. These results indicate that pKM19 vector is a suitable tool for maturation of scFv antibodies.

SEQUENCE LISTING

<160> NUMBER OF SEQ ID NOS: 102

<210> SEQ ID NO 1

<211> LENGTH: 3770

<212> TYPE: DNA

<213> ORGANISM: Escherichia coli

<400> SEQUENCE: 1 gcccaatacg caaaccgcct ctccccgcgc gttggccgat tcattaatgc agctggcacg 60 acaggtttcc cgactggaaa gcgggcagtg agcgcaacgc aattaatgtg agttagctca 120 ctcattaggc accccaggct ttacacttta tgcttccggc tcgtatgttg tgtggaattg 180 tgagcggata acaatttcac acaagatcta gctattctag agattacgcc aagcccccgta 240 ttttacccgt ttaatggaag cttataaagg aggaaatcct catgaaatag agcaccatcg 300 cactggcact gttaccgtta ctgttcaccc cggttaccaa agcacgtacc atggtttccc 360 ttgcggccgc aggagactac aaagacgacg acgacaaaga attcctgcct caacctcctg 420 tcaatgctgg cggcggctct ggtggtggtt ctggtggcgg ctctgagggt ggcggctctg 480

<400> SEQUENCE: 102 gctgaggaga cggtgacc

SEQUENCE LISTING

<160> NUMBER OF SEQ ID NOS: 102

<210> SEQ ID NO 1
<211> LENGTH: 3770
<212> TYPE: DNA
<213> ORGANISM: Escherichia coli

<400> SEQUENCE: 1 gcccaatacg caaaccgcct ctccccgcgc gttggccgat tcattaatgc agctggcacg 60 acaggtttcc cgactggaaa gcgggcagtg agcgcaacgc aattaatgtg agttagctca 120 ctcattaggc accccaggct ttacacttta tgcttccggc tcgtatgttg tgtggaattg 180 tgagcggata acaatttcac acaagatcta gctattctag agattacgcc aagccccgta 240 ttttacccgt ttaatggaag cttataaagg aggaaatcct catgaaatag agcaccatcg 300 cactggcact gttaccgtta ctgttcaccc cggttaccaa agcacgtacc atggtttccc 360 ttgcggccgc aggagactac aaagacgacg acgacaaaga attcctgcct caacctcctg 420 tcaatgctgg cggcggctct ggtggtggtt ctggtggcgg ctctgagggt ggcggctctg 480 agggtggcgg ttctgagggt ggcggctctg agggtggcgg ttccggtggc ggctccggtt 540 ccggtgattt tgattatgaa aaaatggcaa acgctaataa gggggctatg accgaaaatg 600 ccgatgaaaa cgcgctacag tctgacgcta aaggcaaact tgattctgtc gctactgatt 660 acggtgctgc tatcgatggt ttcattggtg acgtttccgg ccttgctaat ggtaatggtg 720 ctactggtga ttttgctggc tctaattccc aaatggctca agtcggtgac ggtgataatt 780 cacctttaat gaataatttc cgtcaatatt taccttcttt gcctcagtcg gttgaatgtc 840 gcccttatgt ctttggcgct ggtaaaccat atgaattttc tattgattgt gacaaaataa 900 acttattccg tggtgtcttt gcgtttcttt tatatgttgc cacctttatg tatgtatttt 960 cgacgtttgc taacatactg cgtaataagg agtcttaagg atcctaatat tgttctggat 1020 attaccagca aggccgatag tttgagttct tctactcagg caagtgatgt tattactaat 1080 caaagaagta ttgcgacaac ggttaatttg cgtgatggac agactctttt actcggtggc 1140 ctcactgatt ataaaaacac ttctcaggat tctggcgtac cgttcctgtc taaaatccct 1200 ttaatcggcc tcctgtttag ctcccgctct gattctaacg aggaaagcac gttatacgtg 1260 ctcgtcaaag caaccatagt acgcgccctg tagcggcgca ttaagcgcgg cgggtgtggt 1320 ggttacgcgc agcgtgaccg ctacacttgc cagcgcccta gcgcccgctc ctttcgcttt 1380 cttcccttcc tttctcgcca cgttcgccgg ctttccccgt caagctctaa atcgggggct 1440 ccctttaggg ttccgattta gtgctttacg gcacctcgac cccaaaaaac ttgattaggg 1500 tgatggttca cgtagtgggc catcgccctg atagacggtt tttcgccctt tgacgttgga 1560 gtccacgttc tttaatagtg gactcttgtt ccaaactgga acaacactca accctatctc 1620 ggtctattct tttgatttat aagggatttt gccgatttcg gcctattggt taaaaaatga 1680 gctgatttaa caaaaattta acgcgaattt taacaaaata ttaacgttta caatttaaat 1740 atttgcttat acaatcttcc tgtttttggg gcttttctga ttatcaaccg gggtacatat 1800 gattgacatg ctagttttac gattaccgtt catcgcaggt ggcacttttc ggggaaatgt 1860 gcgcggaacc cctatttgtt tatttttcta aatacattca aatatgtatc cgctcatgag 1920 acaataaccc tgataaatgc ttcaataata ttgaaaaagg aagagtatga gtattcaaca 1980 tttccgtgtc gcccttattc cctttttttgc ggcattttgc cttcctgttt ttgctcaccc 2040 agaaacgctg gtgaaagtaa aagatgctga agatcagttg ggtgcacgag tgggttacat 2100

```
cgaactggat ctcaacagcg gtaagatcct tgagagtttt cgccccgaag aacgttttcc   2160
aatgatgagc acttttaaag ttctgctatg tggcgcggta ttatcccgta ttgacgccgg   2220
gcaagagcaa ctcggtcgcc gcatacacta ttctcagaat gacttggttg agtactcacc   2280
agtcacagaa aagcatctta cggatggcat gacagtaaga gaattatgca gtgctgccat   2340
aaccatgagt gataacactg cggccaactt acttctgaca acgatcggag gaccgaagga   2400
gctaaccgct tttttgcaca acatgggggga tcatgtaact cgccttgatc gttgggaacc   2460
ggagctgaat gaagccatac caaacgacga gcgtgacacc acgatgcctg tagcaatggc   2520
aacaacgttg cgcaaactat taactggcga actacttact ctagcttccc ggcaacaatt   2580
aatagactgg atggaggcgg ataaagttgc aggaccactt ctgcgctcgg cccttccggc   2640
tggctggttt attgctgata aatctggagc cggtgagcgt gggtctcgcg gtatcattgc   2700
agcactgggg ccagatggta agccctcccg tatcgtagtt atctacacga cggggagtca   2760
ggcaactatg gatgaacgaa atagacagat cgctgagata ggtgcctcac tgattaagca   2820
ttggtaactg tcagaccaag tttactcata tatactttag attgatttaa aacttcattt   2880
ttaatttaaa aggatctagg tgaagatcct ttttgataat ctcatgacca aaatccctta   2940
acgtgagttt tcgttccact gagcgtcaga ccccgtagaa aagatcaaag gatcttcttg   3000
agatcctttt tttctgcgcg taatctgctg cttgcaaaca aaaaaaccac cgctaccagc   3060
ggtggtttgt ttgccggatc aagagctacc aactcttttt ccgaaggtaa ctggcttcag   3120
cagagcgcag ataccaaata ctgtccttct agtgtagccg tagttaggcc accacttcaa   3180
gaactctgta gcaccgccta catacctcgc tctgctaatc ctgttaccag tggctgctgc   3240
cagtggcgat aagtcgtgtc ttaccgggtt ggactcaaga cgatagttac cggataaggc   3300
gcagcggtcg ggctgaacgg ggggttcgtg cacacagccc agcttggagc gaacgaccta   3360
caccgaactg agatacctac agcgtgagct atgagaaagc gccacgcttc ccgaagggag   3420
aaaggcggac aggtatccgg taagcggcag ggtcggaaca ggagagcgca cgagggagct   3480
tccaggggga aacgcctggt atctttatag tcctgtcggg tttcgccacc tctgacttga   3540
gcgtcgattt ttgtgatgct cgtcaggggg gcggagccta tggaaaaacg ccagcaacgc   3600
ggccttttta cggttcctgg ccttttgctg gccttttgct cacatgttct ttcctgcgtt   3660
atcccctgat tctgtggata accgtattac cgcctttgag tgagctgata ccgctcgccg   3720
cagccgaacg accgagcgca gcgagtcagt gagcgaggaa gcggaagagc              3770
```

<210> SEQ ID NO 2
<211> LENGTH: 738
<212> TYPE: DNA
<213> ORGANISM: Escherichia coli
<220> FEATURE:
<221> NAME/KEY: CDS
<222> LOCATION: (1)..(738)
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t

<400> SEQUENCE: 2

```
gag gtg cag ctg gtg gag tct gga gct gag gtg aag aag ccc ggg gcc       48
Glu Val Gln Leu Val Glu Ser Gly Ala Glu Val Lys Lys Pro Gly Ala
1               5                   10                  15
```

```
tca gtg aag gtc tcc tgc aag gct tct gga tac acc ttc acc gcc tcc       96
Ser Val Lys Val Ser Cys Lys Ala Ser Gly Tyr Thr Phe Thr Ala Ser
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga tgg ttc aac cct aat agt ggt ggc aca aac tat gca cag aag ttt      192
Gly Trp Phe Asn Pro Asn Ser Gly Gly Thr Asn Tyr Ala Gln Lys Phe
    50                  55                  60

cag ggc agg gtc acc atg acc ggg gac acg tcc acc agc aca ggc tat      240
Gln Gly Arg Val Thr Met Thr Gly Asp Thr Ser Thr Ser Thr Gly Tyr
65                  70                  75                  80

atg gag ctg agc agg ctg aca tct gac gac gcg ncc gtg tat tat tgt      288
Met Glu Leu Ser Arg Leu Thr Ser Asp Asp Ala Xaa Val Tyr Tyr Cys
                85                  90                  95

gcg aga gat cgg gcc tct gct atg ggc gtc tgg ggc caa ggc acc ctg      336
Ala Arg Asp Arg Ala Ser Ala Met Gly Val Trp Gly Gln Gly Thr Leu
            100                 105                 110

gtc acc gtc tcc tca ggt gga ggc ggt tca ggc gga ggt ggc tct ggc      384
Val Thr Val Ser Ser Gly Gly Gly Gly Ser Gly Gly Gly Gly Ser Gly
        115                 120                 125

ggn ggc gga tcg cag tct gcc ctg act cag cct gcc tcc gcg tcc ggg      432
Gly Gly Gly Ser Gln Ser Ala Leu Thr Gln Pro Ala Ser Ala Ser Gly
    130                 135                 140

tct cct gga cag tca gtc acc atc tcc tgc act gga acc agc agt gac      480
Ser Pro Gly Gln Ser Val Thr Ile Ser Cys Thr Gly Thr Ser Ser Asp
145                 150                 155                 160

gtt ggt ggt tat aac tat gtc tcc tgg tac caa cag cac cca ggc aaa      528
Val Gly Gly Tyr Asn Tyr Val Ser Trp Tyr Gln Gln His Pro Gly Lys
                165                 170                 175

gcc ccc aaa ctc atg att tat gac gtc aat aag cgg ccc tca ggg gtc      576
Ala Pro Lys Leu Met Ile Tyr Asp Val Asn Lys Arg Pro Ser Gly Val
            180                 185                 190

cct gat cgc ttc tct ggc tcc aag tct ggc aac acg gcc tcc ctg acc      624
Pro Asp Arg Phe Ser Gly Ser Lys Ser Gly Asn Thr Ala Ser Leu Thr
        195                 200                 205

gtc tct ggg ctc cag gct gag gat gag gct gat tat tac tgc agc tca      672
Val Ser Gly Leu Gln Ala Glu Asp Glu Ala Asp Tyr Tyr Cys Ser Ser
    210                 215                 220

tat gca ggt agt aac act ttc cta ttc ggc gga ggg acc cag ctc acc      720
Tyr Ala Gly Ser Asn Thr Phe Leu Phe Gly Gly Gly Thr Gln Leu Thr
225                 230                 235                 240

gtt tta ggt gcg gcc gca                                              738
Val Leu Gly Ala Ala Ala
                245


<210> SEQ ID NO 3
<211> LENGTH: 246
<212> TYPE: PRT
<213> ORGANISM: Escherichia coli
<220> FEATURE:
<221> NAME/KEY: misc_feature
<222> LOCATION: (92)..(92)
<223> OTHER INFORMATION: The 'Xaa' at location 92 stands for Thr, Ala,
      Pro, or Ser.

<400> SEQUENCE: 3

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ala Ser
            20                  25                  30
```

```
Tyr Met His Trp Val Arg Gln Ala Pro Gly Gln Gly Leu Glu Trp Met
        35                  40                  45

Gly Trp Phe Asn Pro Asn Ser Gly Gly Thr Asn Tyr Ala Gln Lys Phe
    50                  55                  60

Gln Gly Arg Val Thr Met Thr Gly Asp Thr Ser Thr Ser Thr Gly Tyr
65                  70                  75                  80

Met Glu Leu Ser Arg Leu Thr Ser Asp Asp Ala Xaa Val Tyr Tyr Cys
                85                  90                  95

Ala Arg Asp Arg Ala Ser Ala Met Gly Val Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gln Ser Ala Leu Thr Gln Pro Ala Ser Ala Ser Gly
    130                 135                 140

Ser Pro Gly Gln Ser Val Thr Ile Ser Cys Thr Gly Thr Ser Ser Asp
145                 150                 155                 160

Val Gly Gly Tyr Asn Tyr Val Ser Trp Tyr Gln Gln His Pro Gly Lys
                165                 170                 175

Ala Pro Lys Leu Met Ile Tyr Asp Val Asn Lys Arg Pro Ser Gly Val
            180                 185                 190

Pro Asp Arg Phe Ser Gly Ser Lys Ser Gly Asn Thr Ala Ser Leu Thr
        195                 200                 205

Val Ser Gly Leu Gln Ala Glu Asp Glu Ala Asp Tyr Tyr Cys Ser Ser
    210                 215                 220

Tyr Ala Gly Ser Asn Thr Phe Leu Phe Gly Gly Gly Thr Gln Leu Thr
225                 230                 235                 240

Val Leu Gly Ala Ala Ala
                245


<210> SEQ ID NO 4
<211> LENGTH: 743
<212> TYPE: DNA
<213> ORGANISM: Escherichia coli
<220> FEATURE:
<221> NAME/KEY: CDS
<222> LOCATION: (1)..(741)

<400> SEQUENCE: 4

atg gag gag gtg cag ctg cag gag tct gga gct gag gtg aag aag ccc       48
Met Glu Glu Val Gln Leu Gln Glu Ser Gly Ala Glu Val Lys Lys Pro
1               5                   10                  15

ggg gcc tca gtg aag gtc tcc tgc aag gct tct gga tac acc ttc acc       96
Gly Ala Ser Val Lys Val Ser Cys Lys Ala Ser Gly Tyr Thr Phe Thr
            20                  25                  30

gcc tcc tat atg cac tgg gtg cga cag gcc cct gga caa ggg ctt gag      144
Ala Ser Tyr Met His Trp Val Arg Gln Ala Pro Gly Gln Gly Leu Glu
        35                  40                  45

tgg atg gga tgg ttc aac cct aat agt ggt ggc aca aac tat gca cag      192
Trp Met Gly Trp Phe Asn Pro Asn Ser Gly Gly Thr Asn Tyr Ala Gln
    50                  55                  60

aag ttt cag ggc agg gtc acc atg acc ggg gac acg tcc acc agc aca      240
Lys Phe Gln Gly Arg Val Thr Met Thr Gly Asp Thr Ser Thr Ser Thr
65                  70                  75                  80

ggc tat atg gag ctg agc agg ctg aca tct gac gac gcg gcc gtg tat      288
Gly Tyr Met Glu Leu Ser Arg Leu Thr Ser Asp Asp Ala Ala Val Tyr
                85                  90                  95

tat tgt gcg aga gat cgg gcc tct gct atg ggc gtc tgg ggc caa gga      336
```

```
Tyr Cys Ala Arg Asp Arg Ala Ser Ala Met Gly Val Trp Gly Gln Gly
            100                 105                 110

acc ctg gtc acc gtc tcc tca ggt gga ggc ggt tca ggc gga ggt ggc      384
Thr Leu Val Thr Val Ser Ser Gly Gly Gly Gly Ser Gly Gly Gly Gly
        115                 120                 125

tct ggc ggt ggc gga tcc cag tct gcc ctg act cag cct gcc tcc gtg      432
Ser Gly Gly Gly Gly Ser Gln Ser Ala Leu Thr Gln Pro Ala Ser Val
    130                 135                 140

tct ggg tct cct gga cag tcg atc acc atc tcc tgc act gga acc agc      480
Ser Gly Ser Pro Gly Gln Ser Ile Thr Ile Ser Cys Thr Gly Thr Ser
145                 150                 155                 160

agt gac gtt ggt ggt tat aac tat gtc tcc tgg tac caa cag cac cca      528
Ser Asp Val Gly Gly Tyr Asn Tyr Val Ser Trp Tyr Gln Gln His Pro
                165                 170                 175

ggc aaa gcc ccc aaa ctc atg att tat gat gtc agt cat cgg ccc tca      576
Gly Lys Ala Pro Lys Leu Met Ile Tyr Asp Val Ser His Arg Pro Ser
            180                 185                 190

ggg att tct aat cgc ttc tct ggc tcc aag tct ggc aac acg gcc tcc      624
Gly Ile Ser Asn Arg Phe Ser Gly Ser Lys Ser Gly Asn Thr Ala Ser
        195                 200                 205

ctg acc atc tct agg ctc cag gct gag gac gag gct gat tat tac tgc      672
Leu Thr Ile Ser Arg Leu Gln Ala Glu Asp Glu Ala Asp Tyr Tyr Cys
    210                 215                 220

agc tca tat aca agc agt aac act ttc atc ttc gga act ggg acc cag      720
Ser Ser Tyr Thr Ser Ser Asn Thr Phe Ile Phe Gly Thr Gly Thr Gln
225                 230                 235                 240

ctc acc gtt tta ggt gcg gcc gc                                       743
Leu Thr Val Leu Gly Ala Ala
                245


<210> SEQ ID NO 5
<211> LENGTH: 247
<212> TYPE: PRT
<213> ORGANISM: Escherichia coli

<400> SEQUENCE: 5

Met Glu Glu Val Gln Leu Gln Glu Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ala Ser Tyr Met His Trp Val Arg Gln Ala Pro Gly Gln Gly Leu Glu
        35                  40                  45

Trp Met Gly Trp Phe Asn Pro Asn Ser Gly Gly Thr Asn Tyr Ala Gln
    50                  55                  60

Lys Phe Gln Gly Arg Val Thr Met Thr Gly Asp Thr Ser Thr Ser Thr
65                  70                  75                  80

Gly Tyr Met Glu Leu Ser Arg Leu Thr Ser Asp Asp Ala Ala Val Tyr
                85                  90                  95

Tyr Cys Ala Arg Asp Arg Ala Ser Ala Met Gly Val Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ser Ala Leu Thr Gln Pro Ala Ser Val
    130                 135                 140

Ser Gly Ser Pro Gly Gln Ser Ile Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175
```

```
Gly Lys Ala Pro Lys Leu Met Ile Tyr Asp Val Ser His Arg Pro Ser
            180                 185                 190

Gly Ile Ser Asn Arg Phe Ser Gly Ser Lys Ser Gly Asn Thr Ala Ser
        195                 200                 205

Leu Thr Ile Ser Arg Leu Gln Ala Glu Asp Glu Ala Asp Tyr Tyr Cys
    210                 215                 220

Ser Ser Tyr Thr Ser Ser Asn Thr Phe Ile Phe Gly Thr Gly Thr Gln
225                 230                 235                 240

Leu Thr Val Leu Gly Ala Ala
                245


<210> SEQ ID NO 6
<211> LENGTH: 743
<212> TYPE: DNA
<213> ORGANISM: Escherichia coli
<220> FEATURE:
<221> NAME/KEY: CDS
<222> LOCATION: (1)..(741)

<400> SEQUENCE: 6

atg gag cag gtg cag ctg gtg cag tct gga gct gag gtg aag aag ccc       48
Met Glu Gln Val Gln Leu Val Gln Ser Gly Ala Glu Val Lys Lys Pro
1               5                   10                  15

ggg gcc tca gtg aag gtc tcc tgc aag gcc tct gga tac acc ttc acc       96
Gly Ala Ser Val Lys Val Ser Cys Lys Ala Ser Gly Tyr Thr Phe Thr
            20                  25                  30

gcc tcc tat atg cac tgg gtg cga cag gcc cct gga caa ggg ctt gag      144
Ala Ser Tyr Met His Trp Val Arg Gln Ala Pro Gly Gln Gly Leu Glu
        35                  40                  45

tgg atg gga tgg ttc aac cct aat agt ggt ggc aca aac tat gca cag      192
Trp Met Gly Trp Phe Asn Pro Asn Ser Gly Gly Thr Asn Tyr Ala Gln
    50                  55                  60

aag ttt cag ggc agg gtc acc atg acc ggg gac acg tcc acc agc aca      240
Lys Phe Gln Gly Arg Val Thr Met Thr Gly Asp Thr Ser Thr Ser Thr
65                  70                  75                  80

ggc tat atg gag ctg agc agg ctg aca tct gac gac gcg gcc gtg tat      288
Gly Tyr Met Glu Leu Ser Arg Leu Thr Ser Asp Asp Ala Ala Val Tyr
                85                  90                  95

tat tgt gcg aga gat cgg gcc tct gct atg ggc gtc tgg ggc caa ggc      336
Tyr Cys Ala Arg Asp Arg Ala Ser Ala Met Gly Val Trp Gly Gln Gly
            100                 105                 110

acc ctg gtc acc gtc tcc tca ggt gga ggc ggt tca ggc gga ggc ggc      384
Thr Leu Val Thr Val Ser Ser Gly Gly Gly Gly Ser Gly Gly Gly Gly
        115                 120                 125

tct ggc ggt ggc gga tcg cag tct gcc ctg act cag cct gcc tcc gtg      432
Ser Gly Gly Gly Gly Ser Gln Ser Ala Leu Thr Gln Pro Ala Ser Val
    130                 135                 140

tct ggg tct cct gga cag tcg atc acc atc tcc tgc act gga acc agc      480
Ser Gly Ser Pro Gly Gln Ser Ile Thr Ile Ser Cys Thr Gly Thr Ser
145                 150                 155                 160

agt gac gtt ggt ggt tat aac tat gtc tcc tgg tac caa cag cac cca      528
Ser Asp Val Gly Gly Tyr Asn Tyr Val Ser Trp Tyr Gln Gln His Pro
                165                 170                 175

ggc aaa gcc ccc aaa ctc atg att tat gat gtc act aat cgg cct tca      576
Gly Lys Ala Pro Lys Leu Met Ile Tyr Asp Val Thr Asn Arg Pro Ser
            180                 185                 190

ggg gtt tct agt cgc ttc tct ggc tcc aag tct ggc aac acg gcc tcc      624
Gly Val Ser Ser Arg Phe Ser Gly Ser Lys Ser Gly Asn Thr Ala Ser
        195                 200                 205
```

```
ctg acc atc tct gga ctc cag act gag gac gag gct gat tat tac tgc      672
Leu Thr Ile Ser Gly Leu Gln Thr Glu Asp Glu Ala Asp Tyr Tyr Cys
    210                 215                 220

aac tca ttt aca agc agc aac act tat gtc ttc gga act ggg acc cag      720
Asn Ser Phe Thr Ser Ser Asn Thr Tyr Val Phe Gly Thr Gly Thr Gln
225                 230                 235                 240

ctc acc gtt tta ggt gcg gcc gc                                       743
Leu Thr Val Leu Gly Ala Ala
                245


<210> SEQ ID NO 7
<211> LENGTH: 247
<212> TYPE: PRT
<213> ORGANISM: Escherichia coli

<400> SEQUENCE: 7

Met Glu Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ala Ser Tyr Met His Trp Val Arg Gln Ala Pro Gly Gln Gly Leu Glu
        35                  40                  45

Trp Met Gly Trp Phe Asn Pro Asn Ser Gly Gly Thr Asn Tyr Ala Gln
    50                  55                  60

Lys Phe Gln Gly Arg Val Thr Met Thr Gly Asp Thr Ser Thr Ser Thr
65                  70                  75                  80

Gly Tyr Met Glu Leu Ser Arg Leu Thr Ser Asp Asp Ala Ala Val Tyr
                85                  90                  95

Tyr Cys Ala Arg Asp Arg Ala Ser Ala Met Gly Val Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ser Ala Leu Thr Gln Pro Ala Ser Val
    130                 135                 140

Ser Gly Ser Pro Gly Gln Ser Ile Thr Ile Ser Cys Thr Gly Thr Ser
145                 150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Asp Val Thr Asn Arg Pro Ser
            180                 185                 190

Gly Val Ser Ser Arg Phe Ser Gly Ser Lys Ser Gly Asn Thr Ala Ser
        195                 200                 205

Leu Thr Ile Ser Gly Leu Gln Thr Glu Asp Glu Ala Asp Tyr Tyr Cys
    210                 215                 220

Asn Ser Phe Thr Ser Ser Asn Thr Tyr Val Phe Gly Thr Gly Thr Gln
225                 230                 235                 240

Leu Thr Val Leu Gly Ala Ala
                245


<210> SEQ ID NO 8
<211> LENGTH: 750
<212> TYPE: DNA
<213> ORGANISM: Escherichia coli
<220> FEATURE:
<221> NAME/KEY: CDS
<222> LOCATION: (1)..(750)

<400> SEQUENCE: 8
```

```
gag gag gtg cag ctg gtg cag tct gga gga ggc ttg atc cag ccg ggg       48
Glu Glu Val Gln Leu Val Gln Ser Gly Gly Gly Leu Ile Gln Pro Gly
1               5                   10                  15

ggg tcc ctg aga ctc tct tgt gta gcc tct gag ttc aac gtc aga agc       96
Gly Ser Leu Arg Leu Ser Cys Val Ala Ser Glu Phe Asn Val Arg Ser
            20                  25                  30

aac tac atg agc tgg gtc cgc cag gct cca ggg aag ggg ctg gag tgg      144
Asn Tyr Met Ser Trp Val Arg Gln Ala Pro Gly Lys Gly Leu Glu Trp
        35                  40                  45

gtc tca gtt atg tat gac ggc ggt agt aca tac tac gca gac tcc gtg      192
Val Ser Val Met Tyr Asp Gly Gly Ser Thr Tyr Tyr Ala Asp Ser Val
    50                  55                  60

aag ggc cga ttc acc atc tcc aga gac aat tct aag aac acg gtg tat      240
Lys Gly Arg Phe Thr Ile Ser Arg Asp Asn Ser Lys Asn Thr Val Tyr
65                  70                  75                  80

ctt caa atg aac agc ctg aga gcc gag gac acg gcc gtc tat tac tgt      288
Leu Gln Met Asn Ser Leu Arg Ala Glu Asp Thr Ala Val Tyr Tyr Cys
                85                  90                  95

gcg aga ggc gga ttg ggg ttg cct aca atc gcg tct tgg gag atc tgg      336
Ala Arg Gly Gly Leu Gly Leu Pro Thr Ile Ala Ser Trp Glu Ile Trp
            100                 105                 110

ggc caa ggg aca atg gtc acc gtc tct tca ggt gga ggc ggt tct ggc      384
Gly Gln Gly Thr Met Val Thr Val Ser Ser Gly Gly Gly Gly Ser Gly
        115                 120                 125

gga ggt ggc tct ggc ggt ggc gga tcg tcc tat gtg ctg act cag cca      432
Gly Gly Gly Ser Gly Gly Gly Gly Ser Ser Tyr Val Leu Thr Gln Pro
    130                 135                 140

ccc tcg gtg tca gtg gcc cca gga aag acg gcc acg att acc tgt gcg      480
Pro Ser Val Ser Val Ala Pro Gly Lys Thr Ala Thr Ile Thr Cys Ala
145                 150                 155                 160

gga aac aat ata gga agt aac agt gta tac tgg tac cag cag aaa cca      528
Gly Asn Asn Ile Gly Ser Asn Ser Val Tyr Trp Tyr Gln Gln Lys Pro
                165                 170                 175

ggc ctg gcc cct gta ctg gtc gtc tat gat gat aga gac cgg ccc tca      576
Gly Leu Ala Pro Val Leu Val Val Tyr Asp Asp Arg Asp Arg Pro Ser
            180                 185                 190

ggg atc cct gag cga ttc tct ggc tcc aaa tcc ggg aac acg gcc acc      624
Gly Ile Pro Glu Arg Phe Ser Gly Ser Lys Ser Gly Asn Thr Ala Thr
        195                 200                 205

ctg acc atc agc agg gtc gag gcc ggg gat gag gcc gac tat tct tgt      672
Leu Thr Ile Ser Arg Val Glu Ala Gly Asp Glu Ala Asp Tyr Ser Cys
    210                 215                 220

cag gtg tgg gat cct agt agt gat cac ctc tat gtc ttc gga act ggg      720
Gln Val Trp Asp Pro Ser Ser Asp His Leu Tyr Val Phe Gly Thr Gly
225                 230                 235                 240

acc cag ctc acc gtt tta ggt gcg gcc gca                              750
Thr Gln Leu Thr Val Leu Gly Ala Ala Ala
                245                 250


<210> SEQ ID NO 9
<211> LENGTH: 250
<212> TYPE: PRT
<213> ORGANISM: Escherichia coli

<400> SEQUENCE: 9

Glu Glu Val Gln Leu Val Gln Ser Gly Gly Gly Leu Ile Gln Pro Gly
1               5                   10                  15

Gly Ser Leu Arg Leu Ser Cys Val Ala Ser Glu Phe Asn Val Arg Ser
            20                  25                  30

Asn Tyr Met Ser Trp Val Arg Gln Ala Pro Gly Lys Gly Leu Glu Trp
```

```
        35                  40                  45

Val Ser Val Met Tyr Asp Gly Gly Ser Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Gly Leu Pro Thr Ile Ala Ser Trp Glu Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Ser Tyr Val Leu Thr Gln Pro
    130                 135                 140

Pro Ser Val Ser Val Ala Pro Gly Lys Thr Ala Thr Ile Thr Cys Ala
145                 150                 155                 160

Gly Asn Asn Ile Gly Ser Asn Ser Val Tyr Trp Tyr Gln Gln Lys Pro
                165                 170                 175

Gly Leu Ala Pro Val Leu Val Val Tyr Asp Asp Arg Asp Arg Pro Ser
            180                 185                 190

Gly Ile Pro Glu Arg Phe Ser Gly Ser Lys Ser Gly Asn Thr Ala Thr
        195                 200                 205

Leu Thr Ile Ser Arg Val Glu Ala Gly Asp Glu Ala Asp Tyr Ser Cys
    210                 215                 220

Gln Val Trp Asp Pro Ser Ser Asp His Leu Tyr Val Phe Gly Thr Gly
225                 230                 235                 240

Thr Gln Leu Thr Val Leu Gly Ala Ala Ala
                245                 250


<210> SEQ ID NO 10
<211> LENGTH: 752
<212> TYPE: DNA
<213> ORGANISM: Escherichia coli
<220> FEATURE:
<221> NAME/KEY: CDS
<222> LOCATION: (1)..(750)

<400> SEQUENCE: 10

atg gag gag gtg cag ctg gtg cag tct gga gga ggc ttg atc cag ccg       48
Met Glu Glu Val Gln Leu Val Gln Ser Gly Gly Gly Leu Ile Gln Pro
1               5                   10                  15

ggg ggg tcc ctg aga ctc tct tgt gta gcc tct gag ttc aac gtc aga       96
Gly Gly Ser Leu Arg Leu Ser Cys Val Ala Ser Glu Phe Asn Val Arg
            20                  25                  30

agc aac tac atg agc tgg gtc cgc cag gct cca ggg aag ggg ctg gag      144
Ser Asn Tyr Met Ser Trp Val Arg Gln Ala Pro Gly Lys Gly Leu Glu
        35                  40                  45

tgg gtc tca gtt atg tat gac ggc ggt agt aca tac tac gca gac tcc      192
Trp Val Ser Val Met Tyr Asp Gly Gly Ser Thr Tyr Tyr Ala Asp Ser
    50                  55                  60

gtg aag ggc cga ttc acc atc tcc aga gac aat tct aag aac acg gtg      240
Val Lys Gly Arg Phe Thr Ile Ser Arg Asp Asn Ser Lys Asn Thr Val
65                  70                  75                  80

tat ctt caa atg aac agc ctg aga gcc gag gac acg gcc gtc tat tac      288
Tyr Leu Gln Met Asn Ser Leu Arg Ala Glu Asp Thr Ala Val Tyr Tyr
                85                  90                  95

tgt gcg aga ggc gga ttg ggg ttg cct aca atc gcg cct tgg gag atc      336
Cys Ala Arg Gly Gly Leu Gly Leu Pro Thr Ile Ala Pro Trp Glu Ile
            100                 105                 110
```

```
tgg ggc caa ggg aca atg gtc acc gtc tct tca ggt gga ggc ggt tca      384
Trp Gly Gln Gly Thr Met Val Thr Val Ser Ser Gly Gly Gly Gly Ser
        115                 120                 125

ggc gga ggt ggc tct ggc ggt ggc gga tcg tcc tat gtg ctg act cag      432
Gly Gly Gly Gly Ser Gly Gly Gly Gly Ser Ser Tyr Val Leu Thr Gln
    130                 135                 140

cca ccc tcg gtg tca gtg gcc cca gga aag acg gcc acg att acc tgt      480
Pro Pro Ser Val Ser Val Ala Pro Gly Lys Thr Ala Thr Ile Thr Cys
145                 150                 155                 160

gcg gga aac aat ata gga agt aac agt gta tac tgg tac caa caa aaa      528
Ala Gly Asn Asn Ile Gly Ser Asn Ser Val Tyr Trp Tyr Gln Gln Lys
                165                 170                 175

cca ggc ctg gcc cct gta ctg gtc gtc tat gat gat aga gac cgg ccc      576
Pro Gly Leu Ala Pro Val Leu Val Val Tyr Asp Asp Arg Asp Arg Pro
            180                 185                 190

tca ggg atc cat gag cga ttc tct ggc tcc aaa tcc ggg aac acg gcc      624
Ser Gly Ile His Glu Arg Phe Ser Gly Ser Lys Ser Gly Asn Thr Ala
        195                 200                 205

acc ctg acc atc agc agg gtc gag gcc ggg gat gag gcc gac tat tct      672
Thr Leu Thr Ile Ser Arg Val Glu Ala Gly Asp Glu Ala Asp Tyr Ser
    210                 215                 220

tgt cag gtg tgg gat cct agt agt gat cac ctc tat gtc ttc gga act      720
Cys Gln Val Trp Asp Pro Ser Ser Asp His Leu Tyr Val Phe Gly Thr
225                 230                 235                 240

ggg acc cag ctc acc gtt tta ggt gcg gcc gc                           752
Gly Thr Gln Leu Thr Val Leu Gly Ala Ala
                245                 250


<210> SEQ ID NO 11
<211> LENGTH: 250
<212> TYPE: PRT
<213> ORGANISM: Escherichia coli

<400> SEQUENCE: 11

Met Glu Glu Val Gln Leu Val Gln Ser Gly Gly Gly Leu Ile Gln Pro
1               5                   10                  15

Gly Gly Ser Leu Arg Leu Ser Cys Val Ala Ser Glu Phe Asn Val Arg
            20                  25                  30

Ser Asn Tyr Met Ser Trp Val Arg Gln Ala Pro Gly Lys Gly Leu Glu
        35                  40                  45

Trp Val Ser Val Met Tyr Asp Gly Gly Ser Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Gly Gly Leu Gly Leu Pro Thr Ile Ala Pro Trp Glu Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Ser Tyr Val Leu Thr Gln
    130                 135                 140

Pro Pro Ser Val Ser Val Ala Pro Gly Lys Thr Ala Thr Ile Thr Cys
145                 150                 155                 160

Ala Gly Asn Asn Ile Gly Ser Asn Ser Val Tyr Trp Tyr Gln Gln Lys
                165                 170                 175

Pro Gly Leu Ala Pro Val Leu Val Val Tyr Asp Asp Arg Asp Arg Pro
```

```
            180                 185                 190

Ser Gly Ile His Glu Arg Phe Ser Gly Ser Lys Ser Gly Asn Thr Ala
        195                 200                 205

Thr Leu Thr Ile Ser Arg Val Glu Ala Gly Asp Glu Ala Asp Tyr Ser
    210                 215                 220

Cys Gln Val Trp Asp Pro Ser Ser Asp His Leu Tyr Val Phe Gly Thr
225                 230                 235                 240

Gly Thr Gln Leu Thr Val Leu Gly Ala Ala
                245                 250


<210> SEQ ID NO 12
<211> LENGTH: 752
<212> TYPE: DNA
<213> ORGANISM: Escherichia coli
<220> FEATURE:
<221> NAME/KEY: CDS
<222> LOCATION: (1)..(750)

<400> SEQUENCE: 12

atg gag gag gtg cag ctg gtg cag tct gga gga ggc ttg atc cag ccg       48
Met Glu Glu Val Gln Leu Val Gln Ser Gly Gly Gly Leu Ile Gln Pro
1               5                   10                  15

ggg ggg tcc ctg aga ctc tct tgt gta gcc tct gag ttc aac gtc aga       96
Gly Gly Ser Leu Arg Leu Ser Cys Val Ala Ser Glu Phe Asn Val Arg
            20                  25                  30

agc aac tac atg agc tgg gtc cgc cag gct cca ggg aag ggg ctg gag      144
Ser Asn Tyr Met Ser Trp Val Arg Gln Ala Pro Gly Lys Gly Leu Glu
        35                  40                  45

tgg gtc tca gtt atg tat gac ggc ggt agt aca tac tac gca gac tcc      192
Trp Val Ser Val Met Tyr Asp Gly Gly Ser Thr Tyr Tyr Ala Asp Ser
    50                  55                  60

gtg aag ggc cga ttc acc atc tcc aga gac aat tct aag aac acg gtg      240
Val Lys Gly Arg Phe Thr Ile Ser Arg Asp Asn Ser Lys Asn Thr Val
65                  70                  75                  80

tat ctt caa atg aac agc ctg aga gcc gag gac acg gcc gtc tat tac      288
Tyr Leu Gln Met Asn Ser Leu Arg Ala Glu Asp Thr Ala Val Tyr Tyr
                85                  90                  95

tgt gcg aga ggc gga ttg ggg ttg cct aca atc gcg tct tgg gag atc      336
Cys Ala Arg Gly Gly Leu Gly Leu Pro Thr Ile Ala Ser Trp Glu Ile
            100                 105                 110

tgg ggc caa ggg aca atg gtc acc gtc tct tca ggt gga ggc ggt tca      384
Trp Gly Gln Gly Thr Met Val Thr Val Ser Ser Gly Gly Gly Gly Ser
        115                 120                 125

ggc gga ggt ggc tct ggc ggt ggc gga tcg tcc tat gtg ctg act cag      432
Gly Gly Gly Gly Ser Gly Gly Gly Gly Ser Ser Tyr Val Leu Thr Gln
    130                 135                 140

cca ccc tcg gtg tca gtg gcc cca gga aag acg gcc acg att acc tgt      480
Pro Pro Ser Val Ser Val Ala Pro Gly Lys Thr Ala Thr Ile Thr Cys
145                 150                 155                 160

gcg gga aac aat ata gga agt aac agt gta tac tgg tac cag cag aaa      528
Ala Gly Asn Asn Ile Gly Ser Asn Ser Val Tyr Trp Tyr Gln Gln Lys
                165                 170                 175

cca ggc ctg gcc cct gta ctg gtc gtc tat gat gat aga gac cgg ccc      576
Pro Gly Leu Ala Pro Val Leu Val Val Tyr Asp Asp Arg Asp Arg Pro
            180                 185                 190

tca ggg ctc ccc ggg cga ttc tct ggc tcc aaa tcc ggg aac acg gcc      624
Ser Gly Leu Pro Gly Arg Phe Ser Gly Ser Lys Ser Gly Asn Thr Ala
        195                 200                 205

acc ctg acc atc agc agg gtc gag gcc ggg gat gag gcc gac tat tct      672
Thr Leu Thr Ile Ser Arg Val Glu Ala Gly Asp Glu Ala Asp Tyr Ser
```

```
    210                 215                 220

tgt cag gtg tgg gat cct agt agt gat cac ctc tat gtc ttc gga act      720
Cys Gln Val Trp Asp Pro Ser Ser Asp His Leu Tyr Val Phe Gly Thr
225                 230                 235                 240

ggg acc cag ctc acc gtt tta ggt gcg gcc gc                           752
Gly Thr Gln Leu Thr Val Leu Gly Ala Ala
                245                 250


<210> SEQ ID NO 13
<211> LENGTH: 250
<212> TYPE: PRT
<213> ORGANISM: Escherichia coli

<400> SEQUENCE: 13

Met Glu Glu Val Gln Leu Val Gln Ser Gly Gly Gly Leu Ile Gln Pro
1               5                   10                  15

Gly Gly Ser Leu Arg Leu Ser Cys Val Ala Ser Glu Phe Asn Val Arg
            20                  25                  30

Ser Asn Tyr Met Ser Trp Val Arg Gln Ala Pro Gly Lys Gly Leu Glu
        35                  40                  45

Trp Val Ser Val Met Tyr Asp Gly Gly Ser Thr Tyr Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Val Tyr Tyr
                85                  90                  95

Cys Ala Arg Gly Gly Leu Gly Leu Pro Thr Ile Ala Ser Trp Glu Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Ser Tyr Val Leu Thr Gln
    130                 135                 140

Pro Pro Ser Val Ser Val Ala Pro Gly Lys Thr Ala Thr Ile Thr Cys
145                 150                 155                 160

Ala Gly Asn Asn Ile Gly Ser Asn Ser Val Tyr Trp Tyr Gln Gln Lys
                165                 170                 175

Pro Gly Leu Ala Pro Val Leu Val Val Tyr Asp Asp Arg Asp Arg Pro
            180                 185                 190

Ser Gly Leu Pro Gly Arg Phe Ser Gly Ser Lys Ser Gly Asn Thr Ala
        195                 200                 205

Thr Leu Thr Ile Ser Arg Val Glu Ala Gly Asp Glu Ala Asp Tyr Ser
    210                 215                 220

Cys Gln Val Trp Asp Pro Ser Ser Asp His Leu Tyr Val Phe Gly Thr
225                 230                 235                 240

Gly Thr Gln Leu Thr Val Leu Gly Ala Ala
                245                 250


<210> SEQ ID NO 14
<211> LENGTH: 741
<212> TYPE: DNA
<213> ORGANISM: Escherichia coli
<220> FEATURE:
<221> NAME/KEY: CDS
<222> LOCATION: (1)..(741)

<400> SEQUENCE: 14

gag cag gtg cag ctg cag gag tct ggg gga ggc ttg gta cag cct ggg       48
Glu Gln Val Gln Leu Gln Glu Ser Gly Gly Gly Leu Val Gln Pro Gly
```

```
1               5                   10                  15

ggg tcc ctg aga ctc tcc tgt gca gcc tct gga ttc acc ttt agt act       96
Gly Ser Leu Arg Leu Ser Cys Ala Ala Ser Gly Phe Thr Phe Ser Thr
            20                  25                  30

tat gcc atg agc tgg gtc cgc cag gct cca ggg aag ggg ctg gag tgg      144
Tyr Ala Met Ser Trp Val Arg Gln Ala Pro Gly Lys Gly Leu Glu Trp
        35                  40                  45

gtc tca gtt att agt ggt agt ggt cat aca aca aac tac gcc gac tcc      192
Val Ser Val Ile Ser Gly Ser Gly His Thr Thr Asn Tyr Ala Asp Ser
    50                  55                  60

gtg aag ggc cgc gtc acc ata tcc aga gac aat tcc aag aac aca cta      240
Val Lys Gly Arg Val Thr Ile Ser Arg Asp Asn Ser Lys Asn Thr Leu
65                  70                  75                  80

tat ctg caa atc aac agc ctg aga gcc gac gac acg gcc gtg tat tac      288
Tyr Leu Gln Ile Asn Ser Leu Arg Ala Asp Asp Thr Ala Val Tyr Tyr
                85                  90                  95

tgt gcg aga gat gtg tta gtc cta cag aat gct ttt gat atc tgg ggc      336
Cys Ala Arg Asp Val Leu Val Leu Gln Asn Ala Phe Asp Ile Trp Gly
            100                 105                 110

caa ggg acc acg gtc acc gtc tcc tca ggt gga ggt ggt tca ggc gga      384
Gln Gly Thr Thr Val Thr Val Ser Ser Gly Gly Gly Gly Ser Gly Gly
        115                 120                 125

ggt ggc tct ggc ggt ggc gga tcg gat gtt gtg atg acc cag tct cca      432
Gly Gly Ser Gly Gly Gly Gly Ser Asp Val Val Met Thr Gln Ser Pro
    130                 135                 140

tcc tca ctg tct gca tct gta gga gac aga gtc acc atc act tgt cgg      480
Ser Ser Leu Ser Ala Ser Val Gly Asp Arg Val Thr Ile Thr Cys Arg
145                 150                 155                 160

gcg agt cag ggt att agc agg tgg tta gcc tgg tat caa cag aaa cca      528
Ala Ser Gln Gly Ile Ser Arg Trp Leu Ala Trp Tyr Gln Gln Lys Pro
                165                 170                 175

ggg aaa gcc cct aag ctc ctg atc tac gct gca tcc agt ttg caa agt      576
Gly Lys Ala Pro Lys Leu Leu Ile Tyr Ala Ala Ser Ser Leu Gln Ser
            180                 185                 190

ggg gtc cca tca agg ttc agt ggc agt gga tct ggg aca gat ttc act      624
Gly Val Pro Ser Arg Phe Ser Gly Ser Gly Ser Gly Thr Asp Phe Thr
        195                 200                 205

ctc acc atc agc agt ctg caa cct gaa gat ttt gca act tac atc tgt      672
Leu Thr Ile Ser Ser Leu Gln Pro Glu Asp Phe Ala Thr Tyr Ile Cys
    210                 215                 220

caa cag agt tac agt agg ccg ctc act ttc ggc gga ggg acc aag gtg      720
Gln Gln Ser Tyr Ser Arg Pro Leu Thr Phe Gly Gly Gly Thr Lys Val
225                 230                 235                 240

gaa atc aaa cgt gcg gcc gca                                          741
Glu Ile Lys Arg Ala Ala Ala
                245


<210> SEQ ID NO 15
<211> LENGTH: 247
<212> TYPE: PRT
<213> ORGANISM: Escherichia coli

<400> SEQUENCE: 15

Glu Gln Val Gln Leu Gln Glu Ser Gly Gly Gly Leu Val Gln Pro Gly
1               5                   10                  15

Gly Ser Leu Arg Leu Ser Cys Ala Ala Ser Gly Phe Thr Phe Ser Thr
            20                  25                  30

Tyr Ala Met Ser Trp Val Arg Gln Ala Pro Gly Lys Gly Leu Glu Trp
        35                  40                  45
```

```
Val Ser Val Ile Ser Gly Ser Gly His Thr Thr Asn Tyr Ala Asp Ser
    50                  55                  60

Val Lys Gly Arg Val Thr Ile Ser Arg Asp Asn Ser Lys Asn Thr Leu
65                  70                  75                  80

Tyr Leu Gln Ile Asn Ser Leu Arg Ala Asp Asp Thr Ala Val Tyr Tyr
                85                  90                  95

Cys Ala Arg Asp Val Leu Val Leu Gln Asn Ala Phe Asp Ile Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Gly Ser Asp Val Val Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Gly Ile Ser Arg Trp Leu Ala Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Ile Cys
    210                 215                 220

Gln Gln Ser Tyr Ser Arg Pro Leu Thr Phe Gly Gly Gly Thr Lys Val
225                 230                 235                 240

Glu Ile Lys Arg Ala Ala Ala
                245


<210> SEQ ID NO 16
<211> LENGTH: 771
<212> TYPE: DNA
<213> ORGANISM: Escherichia coli
<220> FEATURE:
<221> NAME/KEY: CDS
<222> LOCATION: (1)..(771)

<400> SEQUENCE: 16

gag cag gtg cag ctg gtg cag tct ggg gcg gag gtg aag aag cct ggg       48
Glu Gln Val Gln Leu Val Gln Ser Gly Ala Glu Val Lys Lys Pro Gly
1               5                   10                  15

gcc tca gtg aga gtt tcc tgc cag gca tct gga tac aca ttc agc agg       96
Ala Ser Val Arg Val Ser Cys Gln Ala Ser Gly Tyr Thr Phe Ser Arg
            20                  25                  30

tac cat atg cac tgg gtg cga cag gcc cct gga caa ggg ctt gag tgg      144
Tyr His Met His Trp Val Arg Gln Ala Pro Gly Gln Gly Leu Glu Trp
        35                  40                  45

atg gga gtg atc gac ccc aat agt ggt aga gta agt tac tca cag aag      192
Met Gly Val Ile Asp Pro Asn Ser Gly Arg Val Ser Tyr Ser Gln Lys
    50                  55                  60

ttc cag gac aga gtt acc atg acc agg gac acg tcc acg agc aca gta      240
Phe Gln Asp Arg Val Thr Met Thr Arg Asp Thr Ser Thr Ser Thr Val
65                  70                  75                  80

tac atg gag ctg aac agc ccg aga tct gag gac acg gcc gtt tat tat      288
Tyr Met Glu Leu Asn Ser Pro Arg Ser Glu Asp Thr Ala Val Tyr Tyr
                85                  90                  95

tgt gcg aga gat cga gga tat tgt aat ggt ggc agg tgc ttt atg gat      336
Cys Ala Arg Asp Arg Gly Tyr Cys Asn Gly Gly Arg Cys Phe Met Asp
            100                 105                 110

gca ttt gac tac tgg ggc cag ggg aca atg gtc acc gtc tct tca ggt      384
```

```
Ala Phe Asp Tyr Trp Gly Gln Gly Thr Met Val Thr Val Ser Ser Gly
        115                 120                 125

gga ggc ggt tta ggc gga ggt ggc tct ggc ggt ggc gga tcg tcc tat      432
Gly Gly Gly Leu Gly Gly Gly Gly Ser Gly Gly Gly Gly Ser Ser Tyr
    130                 135                 140

gtg ctg act cac cca ccc tca ttg tct ggg gcc cca ggg cag agc atc      480
Val Leu Thr His Pro Pro Ser Leu Ser Gly Ala Pro Gly Gln Ser Ile
145                 150                 155                 160

acc atc tcc tgc act ggg agc agt tcc aac atc ggg gca ggt ttt cat      528
Thr Ile Ser Cys Thr Gly Ser Ser Ser Asn Ile Gly Ala Gly Phe His
                165                 170                 175

ata cac tgg tac cag cag ttt cca aaa aca gcc ccc aaa ctc ctt atc      576
Ile His Trp Tyr Gln Gln Phe Pro Lys Thr Ala Pro Lys Leu Leu Ile
            180                 185                 190

tat ggt agt agt aat cga ccc tca ggg gtc cct gac cgc ttc tct ggc      624
Tyr Gly Ser Ser Asn Arg Pro Ser Gly Val Pro Asp Arg Phe Ser Gly
        195                 200                 205

tcc agg tct ggc tcc tca ggc tcc ctg gcc atc act ggg ctc cag gca      672
Ser Arg Ser Gly Ser Ser Gly Ser Leu Ala Ile Thr Gly Leu Gln Ala
    210                 215                 220

gac gat gag gct gat tat tac tgt gtg gga tgg gat ggc agc ctg agt      720
Asp Asp Glu Ala Asp Tyr Tyr Cys Val Gly Trp Asp Gly Ser Leu Ser
225                 230                 235                 240

ggt tat gtc ttc gga act ggg acc cag ctc acc gtt tta ggt gcg gcc      768
Gly Tyr Val Phe Gly Thr Gly Thr Gln Leu Thr Val Leu Gly Ala Ala
                245                 250                 255

gca                                                                  771
Ala


<210> SEQ ID NO 17
<211> LENGTH: 257
<212> TYPE: PRT
<213> ORGANISM: Escherichia coli

<400> SEQUENCE: 17

Glu Gln Val Gln Leu Val Gln Ser Gly Ala Glu Val Lys Lys Pro Gly
1               5                   10                  15

Ala Ser Val Arg Val Ser Cys Gln Ala Ser Gly Tyr Thr Phe Ser Arg
            20                  25                  30

Tyr His Met His Trp Val Arg Gln Ala Pro Gly Gln Gly Leu Glu Trp
        35                  40                  45

Met Gly Val Ile Asp Pro Asn Ser Gly Arg Val Ser Tyr Ser Gln Lys
    50                  55                  60

Phe Gln Asp Arg Val Thr Met Thr Arg Asp Thr Ser Thr Ser Thr Val
65                  70                  75                  80

Tyr Met Glu Leu Asn Ser Pro Arg Ser Glu Asp Thr Ala Val Tyr Tyr
                85                  90                  95

Cys Ala Arg Asp Arg Gly Tyr Cys Asn Gly Gly Arg Cys Phe Met Asp
            100                 105                 110

Ala Phe Asp Tyr Trp Gly Gln Gly Thr Met Val Thr Val Ser Ser Gly
        115                 120                 125

Gly Gly Gly Leu Gly Gly Gly Gly Ser Gly Gly Gly Gly Ser Ser Tyr
    130                 135                 140

Val Leu Thr His Pro Pro Ser Leu Ser Gly Ala Pro Gly Gln Ser Ile
145                 150                 155                 160

Thr Ile Ser Cys Thr Gly Ser Ser Ser Asn Ile Gly Ala Gly Phe His
                165                 170                 175
```

```
Ile His Trp Tyr Gln Gln Phe Pro Lys Thr Ala Pro Lys Leu Leu Ile
            180                 185                 190

Tyr Gly Ser Ser Asn Arg Pro Ser Gly Val Pro Asp Arg Phe Ser Gly
        195                 200                 205

Ser Arg Ser Gly Ser Ser Gly Ser Leu Ala Ile Thr Gly Leu Gln Ala
    210                 215                 220

Asp Asp Glu Ala Asp Tyr Tyr Cys Val Gly Trp Asp Gly Ser Leu Ser
225                 230                 235                 240

Gly Tyr Val Phe Gly Thr Gly Thr Gln Leu Thr Val Leu Gly Ala Ala
                245                 250                 255

Ala


<210> SEQ ID NO 18
<211> LENGTH: 735
<212> TYPE: DNA
<213> ORGANISM: Escherichia coli
<220> FEATURE:
<221> NAME/KEY: CDS
<222> LOCATION: (1)..(735)

<400> SEQUENCE: 18

gag cag gtg cag ctg gtg cag tct ggg gga ggc ttg gta cag cct ggg       48
Glu Gln Val Gln Leu Val Gln Ser Gly Gly Gly Leu Val Gln Pro Gly
1               5                   10                  15

ggg tcc ctg aga ctc tcc tgt gca gcc tct gga ttc acc ttt agc agc       96
Gly Ser Leu Arg Leu Ser Cys Ala Ala Ser Gly Phe Thr Phe Ser Ser
            20                  25                  30

tat gcc atg agc tgg gtc cgc cag gct cca ggg aag ggg ctg gag tgg      144
Tyr Ala Met Ser Trp Val Arg Gln Ala Pro Gly Lys Gly Leu Glu Trp
        35                  40                  45

gtc tca gct att agt ggt agt ggt ggt agc aca tac tac gca gac tcc      192
Val Ser Ala Ile Ser Gly Ser Gly Gly Ser Thr Tyr Tyr Ala Asp Ser
    50                  55                  60

gtg aag ggc cgg ttc acc atc tcc aga gag aat tcc aag aac acg cta      240
Val Lys Gly Arg Phe Thr Ile Ser Arg Glu Asn Ser Lys Asn Thr Leu
65                  70                  75                  80

tat ctg caa atg aat agc ctg aga gcc gag gac acg gct gtg tat tac      288
Tyr Leu Gln Met Asn Ser Leu Arg Ala Glu Asp Thr Ala Val Tyr Tyr
                85                  90                  95

tgt gcg aga caa aca aga gtc cgt gct ttt gat atc tgg ggc caa ggg      336
Cys Ala Arg Gln Thr Arg Val Arg Ala Phe Asp Ile Trp Gly Gln Gly
            100                 105                 110

aca atg gtc acc gtc tct tca ggt gga ggc ggt tca ggc gga ggt ggc      384
Thr Met Val Thr Val Ser Ser Gly Gly Gly Gly Ser Gly Gly Gly Gly
        115                 120                 125

tct ggc ggt ggc gga tcg gac atc cag atg acc cag tct cct tcc gcc      432
Ser Gly Gly Gly Gly Ser Asp Ile Gln Met Thr Gln Ser Pro Ser Ala
    130                 135                 140

ctg tct gca tct gta gga ggc aga gtc acc atc act tgc cgg gca agt      480
Leu Ser Ala Ser Val Gly Gly Arg Val Thr Ile Thr Cys Arg Ala Ser
145                 150                 155                 160

cag agc act agt agc gat tta aat tgg tat cag caa aga cca ggg aaa      528
Gln Ser Thr Ser Ser Asp Leu Asn Trp Tyr Gln Gln Arg Pro Gly Lys
                165                 170                 175

gcc cct aaa ctc ctg atc tct gtt gca tcc act tta caa agt gac gtc      576
Ala Pro Lys Leu Leu Ile Ser Val Ala Ser Thr Leu Gln Ser Asp Val
            180                 185                 190

cca tca agg ttc agt ggc agt ggt tct ggg aca gat ttc agt ctc acc      624
Pro Ser Arg Phe Ser Gly Ser Gly Ser Gly Thr Asp Phe Ser Leu Thr
        195                 200                 205
```

```
atc agc agt ctg caa cct gaa gac ttt gca act tac ttc tgt caa cag      672
Ile Ser Ser Leu Gln Pro Glu Asp Phe Ala Thr Tyr Phe Cys Gln Gln
    210                 215                 220

agt tac agc acc ccg tac act ttt ggc cag ggg acc aaa gtg gat atc      720
Ser Tyr Ser Thr Pro Tyr Thr Phe Gly Gln Gly Thr Lys Val Asp Ile
225                 230                 235                 240

aaa cgt gcg gcc gca                                                  735
Lys Arg Ala Ala Ala
                245


<210> SEQ ID NO 19
<211> LENGTH: 245
<212> TYPE: PRT
<213> ORGANISM: Escherichia coli

<400> SEQUENCE: 19

Glu Gln Val Gln Leu Val Gln Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Glu Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Gln Thr Arg Val Arg Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ala
    130                 135                 140

Leu Ser Ala Ser Val Gly Gly Arg Val Thr Ile Thr Cys Arg Ala Ser
145                 150                 155                 160

Gln Ser Thr Ser Ser Asp Leu Asn Trp Tyr Gln Gln Arg Pro Gly Lys
                165                 170                 175

Ala Pro Lys Leu Leu Ile Ser Val Ala Ser Thr Leu Gln Ser Asp Val
            180                 185                 190

Pro Ser Arg Phe Ser Gly Ser Gly Ser Gly Thr Asp Phe Ser Leu Thr
        195                 200                 205

Ile Ser Ser Leu Gln Pro Glu Asp Phe Ala Thr Tyr Phe Cys Gln Gln
    210                 215                 220

Ser Tyr Ser Thr Pro Tyr Thr Phe Gly Gln Gly Thr Lys Val Asp Ile
225                 230                 235                 240

Lys Arg Ala Ala Ala
                245


<210> SEQ ID NO 20
<211> LENGTH: 765
<212> TYPE: DNA
<213> ORGANISM: Escherichia coli
<220> FEATURE:
<221> NAME/KEY: CDS
<222> LOCATION: (1)..(765)

<400> SEQUENCE: 20
```

```
gag gag gtg cag ctg ttg cag tct ggg gga ggc gtg gtc cag cct ggg       48
Glu Glu Val Gln Leu Leu Gln Ser Gly Gly Gly Val Val Gln Pro Gly
1               5                   10                  15

agg tcc ctg aga ctc tcc tgt gca gcc tct gga ttc agc ttc agt aac       96
Arg Ser Leu Arg Leu Ser Cys Ala Ala Ser Gly Phe Ser Phe Ser Asn
            20                  25                  30

tat gtt atg cac tgg gtc cgc cag gct cca ggc aag ggg ctg gag tgg      144
Tyr Val Met His Trp Val Arg Gln Ala Pro Gly Lys Gly Leu Glu Trp
        35                  40                  45

gtg gca gtt ata tca tat gat gga agc aat aaa tac tac gca gac tcc      192
Val Ala Val Ile Ser Tyr Asp Gly Ser Asn Lys Tyr Tyr Ala Asp Ser
    50                  55                  60

gtg aag ggc cga ttc acc atc tcc aga gac aat tcc aag aac acg cta      240
Val Lys Gly Arg Phe Thr Ile Ser Arg Asp Asn Ser Lys Asn Thr Leu
65                  70                  75                  80

tat ctg caa atg aaa ggc ctg aga cct gag gac acg gct gtg tat tac      288
Tyr Leu Gln Met Lys Gly Leu Arg Pro Glu Asp Thr Ala Val Tyr Tyr
                85                  90                  95

tgt gcg aga agt agt ggc tgg tac ctt ctc ttt gat gct ttt gat atc      336
Cys Ala Arg Ser Ser Gly Trp Tyr Leu Leu Phe Asp Ala Phe Asp Ile
            100                 105                 110

tgg ggc caa ggg aca atg gtc acc gtc tct tca ggt gga ggc ggt tca      384
Trp Gly Gln Gly Thr Met Val Thr Val Ser Ser Gly Gly Gly Gly Ser
        115                 120                 125

ggc gga ggt ggc tct ggc ggt ggc gga tcg gat gtt gtg atg aca cag      432
Gly Gly Gly Gly Ser Gly Gly Gly Gly Ser Asp Val Val Met Thr Gln
    130                 135                 140

tct cca gac tcc ctg gct gtg tcg ctg ggc gag agg gcc acc atc aac      480
Ser Pro Asp Ser Leu Ala Val Ser Leu Gly Glu Arg Ala Thr Ile Asn
145                 150                 155                 160

tgc gag tcc agc cag agt gtt tta ttc agc tcc aac aat aag aac tac      528
Cys Glu Ser Ser Gln Ser Val Leu Phe Ser Ser Asn Asn Lys Asn Tyr
                165                 170                 175

tta gct tgg tac cag cag aaa cca gga cag cct cct aag ctg ctc att      576
Leu Ala Trp Tyr Gln Gln Lys Pro Gly Gln Pro Pro Lys Leu Leu Ile
            180                 185                 190

tac tgg gca tct acc cgg gaa tcc ggg gtc cct gac cga ttc agt ggc      624
Tyr Trp Ala Ser Thr Arg Glu Ser Gly Val Pro Asp Arg Phe Ser Gly
        195                 200                 205

agc ggg tct gag aca gat ttc act ctc acc atc agc agc ctg cag gct      672
Ser Gly Ser Glu Thr Asp Phe Thr Leu Thr Ile Ser Ser Leu Gln Ala
    210                 215                 220

gaa gat gtg gca gtt tat tac tgt cag caa tat tat agg att ccg tgg      720
Glu Asp Val Ala Val Tyr Tyr Cys Gln Gln Tyr Tyr Arg Ile Pro Trp
225                 230                 235                 240

acg ttc ggc caa ggg acc aaa gtg gat atc aaa cgt gcg gcc gca          765
Thr Phe Gly Gln Gly Thr Lys Val Asp Ile Lys Arg Ala Ala Ala
                245                 250                 255


<210> SEQ ID NO 21
<211> LENGTH: 255
<212> TYPE: PRT
<213> ORGANISM: Escherichia coli

<400> SEQUENCE: 21

Glu Glu Val Gln Leu Leu Gln Ser Gly Gly Gly Val Val Gln Pro Gly
1               5                   10                  15

Arg Ser Leu Arg Leu Ser Cys Ala Ala Ser Gly Phe Ser Phe Ser Asn
            20                  25                  30
```

```
Tyr Val Met His Trp Val Arg Gln Ala Pro Gly Lys Gly Leu Glu Trp
        35                  40                  45

Val Ala Val Ile Ser Tyr Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Lys Gly Leu Arg Pro Glu Asp Thr Ala Val Tyr Tyr
                85                  90                  95

Cys Ala Arg Ser Ser Gly Trp Tyr Leu Leu Phe Asp Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Asp Val Val Met Thr Gln
    130                 135                 140

Ser Pro Asp Ser Leu Ala Val Ser Leu Gly Glu Arg Ala Thr Ile Asn
145                 150                 155                 160

Cys Glu Ser Ser Gln Ser Val Leu Phe Ser Ser Asn Asn Lys Asn Tyr
                165                 170                 175

Leu Ala Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Ser Gly
        195                 200                 205

Ser Gly Ser Glu Thr Asp Phe Thr Leu Thr Ile Ser Ser Leu Gln Ala
    210                 215                 220

Glu Asp Val Ala Val Tyr Tyr Cys Gln Gln Tyr Tyr Arg Ile Pro Trp
225                 230                 235                 240

Thr Phe Gly Gln Gly Thr Lys Val Asp Ile Lys Arg Ala Ala Ala
                245                 250                 255


<210> SEQ ID NO 22
<211> LENGTH: 791
<212> TYPE: DNA
<213> ORGANISM: Escherichia coli
<220> FEATURE:
<221> NAME/KEY: CDS
<222> LOCATION: (1)..(786)

<400> SEQUENCE: 22

cag gtg cag ctg cag gag tct ggg gct gag gtg aag aag cct ggg gcc       48
Gln Val Gln Leu Gln Glu Ser Gly Ala Glu Val Lys Lys Pro Gly Ala
1               5                   10                  15

tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga tgg atc aac cct aac agt ggt ggc aca aac tat gca cag aag ttt      192
Gly Trp Ile Asn Pro Asn Ser Gly Gly Thr Asn Tyr Ala Gln Lys Phe
    50                  55                  60

cag ggc agg gtc acc atg acc agg gac acg tcc atc agc aca gcc tac      240
Gln Gly Arg Val Thr Met Thr Arg Asp Thr Ser Ile Ser Thr Ala Tyr
65                  70                  75                  80

atg gag ctg agc agg ctg aga tct gac gac acg gcc gtg tat tac tgt      288
Met Glu Leu Ser Arg Leu Arg Ser Asp Asp Thr Ala Val Tyr Tyr Cys
                85                  90                  95

gcg aga gat tcg cca caa aat tgt act aat ggt gta tgc cac cgg ggg      336
Ala Arg Asp Ser Pro Gln Asn Cys Thr Asn Gly Val Cys His Arg Gly
```

```
            100                 105                 110

agt cat gtc cac tac tac ggt atg gac gtc tgg ggc caa ggc acc ctg      384
Ser His Val His Tyr Tyr Gly Met Asp Val Trp Gly Gln Gly Thr Leu
        115                 120                 125

gtc acc gtc tct tca ggt ggg ggc ggt tca ggc gga ggt ggc tct ggc      432
Val Thr Val Ser Ser Gly Gly Gly Gly Ser Gly Gly Gly Gly Ser Gly
    130                 135                 140

ggt ggc gga tcg cag tct gcc ctg act cag cct gcc tcc gcg gcc ggg      480
Gly Gly Gly Ser Gln Ser Ala Leu Thr Gln Pro Ala Ser Ala Ala Gly
145                 150                 155                 160

tct cct gga cag tca gtc acc atc tcc tgc act gga acc agc agt gat      528
Ser Pro Gly Gln Ser Val Thr Ile Ser Cys Thr Gly Thr Ser Ser Asp
                165                 170                 175

gtt ggt ggt tat aac tat gtc tcc tgg tac caa cag cac cca ggc aaa      576
Val Gly Gly Tyr Asn Tyr Val Ser Trp Tyr Gln Gln His Pro Gly Lys
            180                 185                 190

gcc ccc aaa ctc atg att tat gac gtc aat aag cgg ccc tca ggg gtc      624
Ala Pro Lys Leu Met Ile Tyr Asp Val Asn Lys Arg Pro Ser Gly Val
        195                 200                 205

cct gat cgc ttc tct gcc tcc aag tct ggc aac acg gcc tcc ctg acc      672
Pro Asp Arg Phe Ser Ala Ser Lys Ser Gly Asn Thr Ala Ser Leu Thr
    210                 215                 220

gtc tct ggg ctc cag gct gac gat gag gct gat tac tac tgc gct tca      720
Val Ser Gly Leu Gln Ala Asp Asp Glu Ala Asp Tyr Tyr Cys Ala Ser
225                 230                 235                 240

tat gca ggc acc tac agt tat gtc ttc gga act ggg acc cag ctc acc      768
Tyr Ala Gly Thr Tyr Ser Tyr Val Phe Gly Thr Gly Thr Gln Leu Thr
                245                 250                 255

gtt tta ggt gcg gcc gca ggaga                                        791
Val Leu Gly Ala Ala Ala
            260


<210> SEQ ID NO 23
<211> LENGTH: 262
<212> TYPE: PRT
<213> ORGANISM: Escherichia coli

<400> SEQUENCE: 23

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ser Pro Gln Asn Cys Thr Asn Gly Val Cys His Arg Gly
            100                 105                 110

Ser His Val His Tyr Tyr Gly Met Asp Val Trp Gly Gln Gly Thr Leu
        115                 120                 125

Val Thr Val Ser Ser Gly Gly Gly Gly Ser Gly Gly Gly Gly Ser Gly
    130                 135                 140

Gly Gly Gly Ser Gln Ser Ala Leu Thr Gln Pro Ala Ser Ala Ala Gly
145                 150                 155                 160
```

```
Ser Pro Gly Gln Ser Val Thr Ile Ser Cys Thr Gly Thr Ser Ser Asp
                165                 170                 175

Val Gly Gly Tyr Asn Tyr Val Ser Trp Tyr Gln Gln His Pro Gly Lys
            180                 185                 190

Ala Pro Lys Leu Met Ile Tyr Asp Val Asn Lys Arg Pro Ser Gly Val
        195                 200                 205

Pro Asp Arg Phe Ser Ala Ser Lys Ser Gly Asn Thr Ala Ser Leu Thr
    210                 215                 220

Val Ser Gly Leu Gln Ala Asp Asp Glu Ala Asp Tyr Tyr Cys Ala Ser
225                 230                 235                 240

Tyr Ala Gly Thr Tyr Ser Tyr Val Phe Gly Thr Gly Thr Gln Leu Thr
                245                 250                 255

Val Leu Gly Ala Ala Ala
            260


<210> SEQ ID NO 24
<211> LENGTH: 786
<212> TYPE: DNA
<213> ORGANISM: Escherichia coli
<220> FEATURE:
<221> NAME/KEY: CDS
<222> LOCATION: (1)..(786)

<400> SEQUENCE: 24

gag gtg cag ctg ttg cag tct ggg gcc gag gtg aag aag cct ggg gcc       48
Glu Val Gln Leu Leu Gln Ser Gly Ala Glu Val Lys Lys Pro Gly Ala
1               5                   10                  15

tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga tgg atc aac cct aac agt ggt ggc aca aac tat gca cag aag ttt      192
Gly Trp Ile Asn Pro Asn Ser Gly Gly Thr Asn Tyr Ala Gln Lys Phe
    50                  55                  60

cag ggc agg gtc acc atg acc agg gac acg tcc atc agc aca gcc tac      240
Gln Gly Arg Val Thr Met Thr Arg Asp Thr Ser Ile Ser Thr Ala Tyr
65                  70                  75                  80

atg gag ctg agc agg ctg aga tct gac gac acg gcc gtg tat tac tgt      288
Met Glu Leu Ser Arg Leu Arg Ser Asp Asp Thr Ala Val Tyr Tyr Cys
                85                  90                  95

gcg aga gat tcg cca caa aat tgt act aat ggt gta tgc cac cgg ggg      336
Ala Arg Asp Ser Pro Gln Asn Cys Thr Asn Gly Val Cys His Arg Gly
            100                 105                 110

agt cat gtc cac tac tac ggt atg gac gtc tgg ggc cag gga acc ctg      384
Ser His Val His Tyr Tyr Gly Met Asp Val Trp Gly Gln Gly Thr Leu
        115                 120                 125

gtc acc gtc tcc tca ggt ggg ggc ggt tca ggc gga ggt ggc tct ggc      432
Val Thr Val Ser Ser Gly Gly Gly Gly Ser Gly Gly Gly Gly Ser Gly
    130                 135                 140

ggt ggc gga tcg cag tct gcc ctg act cag cct gcc tcc gcg gcc ggg      480
Gly Gly Gly Ser Gln Ser Ala Leu Thr Gln Pro Ala Ser Ala Ala Gly
145                 150                 155                 160

tgt ctt gga cag tca gtc acc atc tcc tgc act gga acc agc agt gat      528
Cys Leu Gly Gln Ser Val Thr Ile Ser Cys Thr Gly Thr Ser Ser Asp
                165                 170                 175

gtt ggt ggt tat aaa tat gtc tcc tgg tac caa cag cac cca ggc aaa      576
Val Gly Gly Tyr Lys Tyr Val Ser Trp Tyr Gln Gln His Pro Gly Lys
```

```
            180                 185                 190

gcc ccc aaa ctc atg att tat gac gtc aat aag cgg ccc tca ggg gtc      624
Ala Pro Lys Leu Met Ile Tyr Asp Val Asn Lys Arg Pro Ser Gly Val
        195                 200                 205

cct gat cgc ttc ttt gcc tcc aag tct ggc aac acg gcc tcc ctg acc      672
Pro Asp Arg Phe Phe Ala Ser Lys Ser Gly Asn Thr Ala Ser Leu Thr
    210                 215                 220

gtc tct ggg ctc cag gct gac gat gag gct gat tac tac tgc gct tca      720
Val Ser Gly Leu Gln Ala Asp Asp Glu Ala Asp Tyr Tyr Cys Ala Ser
225                 230                 235                 240

tat gca ggc acc tac agt tat gtc ttc gga act ggg acc cag ctc acc      768
Tyr Ala Gly Thr Tyr Ser Tyr Val Phe Gly Thr Gly Thr Gln Leu Thr
                245                 250                 255

gtt tta ggt gcg gcc gca                                              786
Val Leu Gly Ala Ala Ala
            260


<210> SEQ ID NO 25
<211> LENGTH: 262
<212> TYPE: PRT
<213> ORGANISM: Escherichia coli

<400> SEQUENCE: 25

Glu Val Gln Leu Leu Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ser Pro Gln Asn Cys Thr Asn Gly Val Cys His Arg Gly
            100                 105                 110

Ser His Val His Tyr Tyr Gly Met Asp Val Trp Gly Gln Gly Thr Leu
        115                 120                 125

Val Thr Val Ser Ser Gly Gly Gly Gly Ser Gly Gly Gly Gly Ser Gly
    130                 135                 140

Gly Gly Gly Ser Gln Ser Ala Leu Thr Gln Pro Ala Ser Ala Ala Gly
145                 150                 155                 160

Cys Leu Gly Gln Ser Val Thr Ile Ser Cys Thr Gly Thr Ser Ser Asp
                165                 170                 175

Val Gly Gly Tyr Lys Tyr Val Ser Trp Tyr Gln Gln His Pro Gly Lys
            180                 185                 190

Ala Pro Lys Leu Met Ile Tyr Asp Val Asn Lys Arg Pro Ser Gly Val
        195                 200                 205

Pro Asp Arg Phe Phe Ala Ser Lys Ser Gly Asn Thr Ala Ser Leu Thr
    210                 215                 220

Val Ser Gly Leu Gln Ala Asp Asp Glu Ala Asp Tyr Tyr Cys Ala Ser
225                 230                 235                 240

Tyr Ala Gly Thr Tyr Ser Tyr Val Phe Gly Thr Gly Thr Gln Leu Thr
                245                 250                 255

Val Leu Gly Ala Ala Ala
```

```
            260


<210> SEQ ID NO 26
<211> LENGTH: 789
<212> TYPE: DNA
<213> ORGANISM: Escherichia coli
<220> FEATURE:
<221> NAME/KEY: CDS
<222> LOCATION: (1)..(789)

<400> SEQUENCE: 26

gag gtg cag ctg gtg gag tct ggg gct gag gtg aag aag cct ggg gcc       48
Glu Val Gln Leu Val Glu Ser Gly Ala Glu Val Lys Lys Pro Gly Ala
1               5                   10                  15

tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga tgg atc aac cct aac agt ggt ggc aca aac tat gca cag aag ttt      192
Gly Trp Ile Asn Pro Asn Ser Gly Gly Thr Asn Tyr Ala Gln Lys Phe
    50                  55                  60

cag ggc agg gtc acc atg acc agg gac acg tcc atc agc aca gcc tac      240
Gln Gly Arg Val Thr Met Thr Arg Asp Thr Ser Ile Ser Thr Ala Tyr
65                  70                  75                  80

atg gag ctg agc agg ctg aga tct gac gac acg gcc gtg tat tac tgt      288
Met Glu Leu Ser Arg Leu Arg Ser Asp Asp Thr Ala Val Tyr Tyr Cys
                85                  90                  95

gtg aga ggt tcg cca caa aat tgt act aat ggt gta tgc cac cgg ggg      336
Val Arg Gly Ser Pro Gln Asn Cys Thr Asn Gly Val Cys His Arg Gly
            100                 105                 110

agt cat gtc cac tac tac ggt atg gac gtc tgg ggc caa ggg acc acg      384
Ser His Val His Tyr Tyr Gly Met Asp Val Trp Gly Gln Gly Thr Thr
        115                 120                 125

gtc acc gtc tcc tca ggt ggg ggc ggt tca ggc gga ggt ggc tct ggc      432
Val Thr Val Ser Ser Gly Gly Gly Gly Ser Gly Gly Gly Gly Ser Gly
    130                 135                 140

ggt ggc gga tcg cag tct gcc ctg act cag cct gcc tcc gtg tct ggg      480
Gly Gly Gly Ser Gln Ser Ala Leu Thr Gln Pro Ala Ser Val Ser Gly
145                 150                 155                 160

tct cct gga cag tcg atc acc atc tcc tgc act gga acc agc agt gat      528
Ser Pro Gly Gln Ser Ile Thr Ile Ser Cys Thr Gly Thr Ser Ser Asp
                165                 170                 175

gtt ggg agt tat aac ctt gtc tcc tgg tac caa cag cac cca ggc aaa      576
Val Gly Ser Tyr Asn Leu Val Ser Trp Tyr Gln Gln His Pro Gly Lys
            180                 185                 190

gcc ccc aaa ctc atg att tat gag gtc agt aat cgg ccc tca ggg gtt      624
Ala Pro Lys Leu Met Ile Tyr Glu Val Ser Asn Arg Pro Ser Gly Val
        195                 200                 205

tgt aat cgc ttc tct ggc tcc aag tct ggc aac acg gcc tcc ctg acc      672
Cys Asn Arg Phe Ser Gly Ser Lys Ser Gly Asn Thr Ala Ser Leu Thr
    210                 215                 220

atc tct ggg ctc cag gct gag gac gag gct gat tat tac tgc agc tca      720
Ile Ser Gly Leu Gln Ala Glu Asp Glu Ala Asp Tyr Tyr Cys Ser Ser
225                 230                 235                 240

tat aca agc agc agc act ctc gag gtg ttc ggc gga ggg acc cag ctc      768
Tyr Thr Ser Ser Ser Thr Leu Glu Val Phe Gly Gly Gly Thr Gln Leu
                245                 250                 255

acc gtt tta ggt gcg gcc gca                                          789
Thr Val Leu Gly Ala Ala Ala
```

```
            260


<210> SEQ ID NO 27
<211> LENGTH: 263
<212> TYPE: PRT
<213> ORGANISM: Escherichia coli

<400> SEQUENCE: 27

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Val Arg Gly Ser Pro Gln Asn Cys Thr Asn Gly Val Cys His Arg Gly
            100                 105                 110

Ser His Val His Tyr Tyr Gly Met Asp Val Trp Gly Gln Gly Thr Thr
        115                 120                 125

Val Thr Val Ser Ser Gly Gly Gly Gly Ser Gly Gly Gly Gly Ser Gly
    130                 135                 140

Gly Gly Gly Ser Gln Ser Ala Leu Thr Gln Pro Ala Ser Val Ser Gly
145                 150                 155                 160

Ser Pro Gly Gln Ser Ile Thr Ile Ser Cys Thr Gly Thr Ser Ser Asp
                165                 170                 175

Val Gly Ser Tyr Asn Leu Val Ser Trp Tyr Gln Gln His Pro Gly Lys
            180                 185                 190

Ala Pro Lys Leu Met Ile Tyr Glu Val Ser Asn Arg Pro Ser Gly Val
        195                 200                 205

Cys Asn Arg Phe Ser Gly Ser Lys Ser Gly Asn Thr Ala Ser Leu Thr
    210                 215                 220

Ile Ser Gly Leu Gln Ala Glu Asp Glu Ala Asp Tyr Tyr Cys Ser Ser
225                 230                 235                 240

Tyr Thr Ser Ser Ser Thr Leu Glu Val Phe Gly Gly Gly Thr Gln Leu
                245                 250                 255

Thr Val Leu Gly Ala Ala Ala
            260


<210> SEQ ID NO 28
<211> LENGTH: 747
<212> TYPE: DNA
<213> ORGANISM: Escherichia coli
<220> FEATURE:
<221> NAME/KEY: CDS
<222> LOCATION: (1)..(747)

<400> SEQUENCE: 28

cag gag gtg cag ctg gtg gag tct ggg ggt ggc ttg gtc cag cct ggg       48
Gln Glu Val Gln Leu Val Glu Ser Gly Gly Gly Leu Val Gln Pro Gly
1               5                   10                  15

ggg tcc ctg aga ctc tcc tgt gca gcc tct gga ttc acc ctc agt agc       96
Gly Ser Leu Arg Leu Ser Cys Ala Ala Ser Gly Phe Thr Leu Ser Ser
            20                  25                  30
```

```
tat gct atg cac tgg gtc cgc cag gct cca ggg aag ggg ctg gag tgg      144
Tyr Ala Met His Trp Val Arg Gln Ala Pro Gly Lys Gly Leu Glu Trp
        35                  40                  45

gtc tca act att agt ggt ggt ggt ggt agc aca tac tac gca gac tcc      192
Val Ser Thr Ile Ser Gly Gly Gly Gly Ser Thr Tyr Tyr Ala Asp Ser
    50                  55                  60

gtg aag ggc cgg ttc acc atc tcc aga gac aat tcc aag aac acg ctg      240
Val Lys Gly Arg Phe Thr Ile Ser Arg Asp Asn Ser Lys Asn Thr Leu
65                  70                  75                  80

tat ctg caa atg aac agc ctg aga gcc gag gac acg gcc gta tat tac      288
Tyr Leu Gln Met Asn Ser Leu Arg Ala Glu Asp Thr Ala Val Tyr Tyr
                85                  90                  95

tgt gcg aga cgg ggg cgg gct ttt gat atc tgg ggc caa ggg acc acg      336
Cys Ala Arg Arg Gly Arg Ala Phe Asp Ile Trp Gly Gln Gly Thr Thr
            100                 105                 110

gtc acc gtc tcc tta ggt gga ggc ggt tca ggc gga ggt ggc tct ggc      384
Val Thr Val Ser Leu Gly Gly Gly Gly Ser Gly Gly Gly Gly Ser Gly
        115                 120                 125

ggt ggc gga tcg cag tct gtg ttg acg cag ccg ccc tca gtg tct ggg      432
Gly Gly Gly Ser Gln Ser Val Leu Thr Gln Pro Pro Ser Val Ser Gly
    130                 135                 140

gcc cca ggg cag agg gtc acc atc tcc tgc act ggg agc agc tcc aac      480
Ala Pro Gly Gln Arg Val Thr Ile Ser Cys Thr Gly Ser Ser Ser Asn
145                 150                 155                 160

atc ggg gcg ggg tat gat gta cac tgg tac cag cag ctt cca gga aca      528
Ile Gly Ala Gly Tyr Asp Val His Trp Tyr Gln Gln Leu Pro Gly Thr
                165                 170                 175

gcc ccc aaa ctc ctc att tat ggt aac agc aat cgg ccc tca ggg gtc      576
Ala Pro Lys Leu Leu Ile Tyr Gly Asn Ser Asn Arg Pro Ser Gly Val
            180                 185                 190

cct gac cga ttc tct ggc tcc aag tct ggc acc tca gcc tcc ctg gcc      624
Pro Asp Arg Phe Ser Gly Ser Lys Ser Gly Thr Ser Ala Ser Leu Ala
        195                 200                 205

atc act ggg ctc cag gct gag gat gag gct gat tat tat tgc tcc agt      672
Ile Thr Gly Leu Gln Ala Glu Asp Glu Ala Asp Tyr Tyr Cys Ser Ser
    210                 215                 220

cct atg atc agc agc ctg agt ggt cat gtg gta ttc ggc gga ggg acc      720
Pro Met Ile Ser Ser Leu Ser Gly His Val Val Phe Gly Gly Gly Thr
225                 230                 235                 240

aag gtg acc gtc cta ggt gcg gcc gca                                  747
Lys Val Thr Val Leu Gly Ala Ala Ala
                245


<210> SEQ ID NO 29
<211> LENGTH: 249
<212> TYPE: PRT
<213> ORGANISM: Escherichia coli

<400> SEQUENCE: 29

Gln Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Leu Ser Ser
            20                  25                  30

Tyr Ala Met His Trp Val Arg Gln Ala Pro Gly Lys Gly Leu Glu Trp
        35                  40                  45

Val Ser Thr Ile Ser Gly Gly Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80
```

```
Tyr Leu Gln Met Asn Ser Leu Arg Ala Glu Asp Thr Ala Val Tyr Tyr
                85                  90                  95

Cys Ala Arg Arg Gly Arg Ala Phe Asp Ile Trp Gly Gln Gly Thr Thr
            100                 105                 110

Val Thr Val Ser Leu Gly Gly Gly Gly Ser Gly Gly Gly Gly Ser Gly
        115                 120                 125

Gly Gly Gly Ser Gln Ser Val Leu Thr Gln Pro Pro Ser Val Ser Gly
    130                 135                 140

Ala Pro Gly Gln Arg Val Thr Ile Ser Cys Thr Gly Ser Ser Ser Asn
145                 150                 155                 160

Ile Gly Ala Gly Tyr Asp Val His Trp Tyr Gln Gln Leu Pro Gly Thr
                165                 170                 175

Ala Pro Lys Leu Leu Ile Tyr Gly Asn Ser Asn Arg Pro Ser Gly Val
            180                 185                 190

Pro Asp Arg Phe Ser Gly Ser Lys Ser Gly Thr Ser Ala Ser Leu Ala
        195                 200                 205

Ile Thr Gly Leu Gln Ala Glu Asp Glu Ala Asp Tyr Tyr Cys Ser Ser
    210                 215                 220

Pro Met Ile Ser Ser Leu Ser Gly His Val Val Phe Gly Gly Gly Thr
225                 230                 235                 240

Lys Val Thr Val Leu Gly Ala Ala Ala
                245


<210> SEQ ID NO 30
<211> LENGTH: 747
<212> TYPE: DNA
<213> ORGANISM: Escherichia coli
<220> FEATURE:
<221> NAME/KEY: CDS
<222> LOCATION: (1)..(747)

<400> SEQUENCE: 30

cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15

tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga tgg atc aac cct aac agt ggt ggc aca aac tat gca cag aag ttc      192
Gly Trp Ile Asn Pro Asn Ser Gly Gly Thr Asn Tyr Ala Gln Lys Phe
    50                  55                  60

cag ggc agg gtc acc atg acc agg gac acg tcc att ggc aca gtc tac      240
Gln Gly Arg Val Thr Met Thr Arg Asp Thr Ser Ile Gly Thr Val Tyr
65                  70                  75                  80

atg gag ttg agc agc ctg aca tct gac gac acg gcc atg tat tat tgt      288
Met Glu Leu Ser Ser Leu Thr Ser Asp Asp Thr Ala Met Tyr Tyr Cys
                85                  90                  95

gcg aga aac aat gtt gct atg ggt tat act atg gac gtc tgg ggc caa      336
Ala Arg Asn Asn Val Ala Met Gly Tyr Thr Met Asp Val Trp Gly Gln
            100                 105                 110

ggg aca atg gtc acc gtc tct tca ggt gga ggc ggt tca ggc gga ggt      384
Gly Thr Met Val Thr Val Ser Ser Gly Gly Gly Gly Ser Gly Gly Gly
        115                 120                 125

ggc tct ggc ggt ggc gga tcg cag tct gcc ctg act cag cct gcc tcc      432
Gly Ser Gly Gly Gly Gly Ser Gln Ser Ala Leu Thr Gln Pro Ala Ser
```

```
    130                 135                 140

gcg tcc ggg tct cct gga cag tca gtc acc atc tcc tgc act gga acc      480
Ala Ser Gly Ser Pro Gly Gln Ser Val Thr Ile Ser Cys Thr Gly Thr
145                 150                 155                 160

agc agt gac gtt ggt ggt tat aac tat gtc tcc tgg tac caa cag cac      528
Ser Ser Asp Val Gly Gly Tyr Asn Tyr Val Ser Trp Tyr Gln Gln His
                165                 170                 175

cca ggc aaa acc ccc aaa ctc ttg att tat gag gtc agt agt cgg ccc      576
Pro Gly Lys Thr Pro Lys Leu Leu Ile Tyr Glu Val Ser Ser Arg Pro
            180                 185                 190

tca ggg gtt tct aat cgc ttc tct ggc tcc aag cct ggc aac acg gcc      624
Ser Gly Val Ser Asn Arg Phe Ser Gly Ser Lys Pro Gly Asn Thr Ala
        195                 200                 205

tcc ctg acc atc tct ggt ctc cag gct gag gac gag gct gat tat tac      672
Ser Leu Thr Ile Ser Gly Leu Gln Ala Glu Asp Glu Ala Asp Tyr Tyr
    210                 215                 220

tgc atc tca tat aca agc agc aac act tgg gtg ttc ggc gga ggg acc      720
Cys Ile Ser Tyr Thr Ser Ser Asn Thr Trp Val Phe Gly Gly Gly Thr
225                 230                 235                 240

cag ctc acc gtt tta ggt gcg gcc gca                                  747
Gln Leu Thr Val Leu Gly Ala Ala Ala
                245


<210> SEQ ID NO 31
<211> LENGTH: 249
<212> TYPE: PRT
<213> ORGANISM: Escherichia coli

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Gly Thr Val Tyr
65                  70                  75                  80

Met Glu Leu Ser Ser Leu Thr Ser Asp Asp Thr Ala Met Tyr Tyr Cys
                85                  90                  95

Ala Arg Asn Asn Val Ala Met Gly Tyr Thr Met Asp Val Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Gln Ser Ala Leu Thr Gln Pro Ala Ser
    130                 135                 140

Ala Ser Gly Ser Pro Gly Gln Ser Val Thr Ile Ser Cys Thr Gly Thr
145                 150                 155                 160

Ser Ser Asp Val Gly Gly Tyr Asn Tyr Val Ser Trp Tyr Gln Gln His
                165                 170                 175

Pro Gly Lys Thr Pro Lys Leu Leu Ile Tyr Glu Val Ser Ser Arg Pro
            180                 185                 190

Ser Gly Val Ser Asn Arg Phe Ser Gly Ser Lys Pro Gly Asn Thr Ala
        195                 200                 205

Ser Leu Thr Ile Ser Gly Leu Gln Ala Glu Asp Glu Ala Asp Tyr Tyr
    210                 215                 220
```

```
Cys Ile Ser Tyr Thr Ser Ser Asn Thr Trp Val Phe Gly Gly Gly Thr
225                 230                 235                 240

Gln Leu Thr Val Leu Gly Ala Ala Ala
                245


<210> SEQ ID NO 32
<211> LENGTH: 733
<212> TYPE: DNA
<213> ORGANISM: Escherichia coli
<220> FEATURE:
<221> NAME/KEY: CDS
<222> LOCATION: (1)..(732)

<400> SEQUENCE: 32

gag gtg cag ctg ttg cag tct ggg gcg gag gtg aag aag cct ggg gcc       48
Glu Val Gln Leu Leu Gln Ser Gly Ala Glu Val Lys Lys Pro Gly Ala
1               5                   10                  15

tca gtg aag gtc tcc tgc aag gct tct gga tac acc ttc acc ggc tac       96
Ser Val Lys Val Ser Cys Lys Ala Ser Gly Tyr Thr Phe Thr Gly Tyr
            20                  25                  30

tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45

gga tgg atc aac cct aac agt ggt ggc aca aac tat gca cag aag ttt      192
Gly Trp Ile Asn Pro Asn Ser Gly Gly Thr Asn Tyr Ala Gln Lys Phe
    50                  55                  60

cag ggc aga gtc acc atg acc agg aac acc tcc ata agc aca gcc tac      240
Gln Gly Arg Val Thr Met Thr Arg Asn Thr Ser Ile Ser Thr Ala Tyr
65                  70                  75                  80

atg gag ctg agc agc ctg aga tct gag gac acg gcc gtg tat tac tgt      288
Met Glu Leu Ser Ser Leu Arg Ser Glu Asp Thr Ala Val Tyr Tyr Cys
                85                  90                  95

gcg ggt cag gag gca cat ggg gac ggt atg gac gtc tgg ggc caa ggg      336
Ala Gly Gln Glu Ala His Gly Asp Gly Met Asp Val Trp Gly Gln Gly
            100                 105                 110

acc acg gtc acc gtc tcc tcg gtg gag cga ggt ggc tct ggc ggt ggc      384
Thr Thr Val Thr Val Ser Ser Val Glu Arg Gly Gly Ser Gly Gly Gly
        115                 120                 125

gga tcg cag tct gcc ctg act cag cct gcc tcc gcg tcc ggg tct cct      432
Gly Ser Gln Ser Ala Leu Thr Gln Pro Ala Ser Ala Ser Gly Ser Pro
    130                 135                 140

gga cag tcg atc acc atc tcc tgc act gga acc agc ggt gac gtt ggt      480
Gly Gln Ser Ile Thr Ile Ser Cys Thr Gly Thr Ser Gly Asp Val Gly
145                 150                 155                 160

ggt tat aac tat gtc tcc tgg tac caa cag cac cca ggc aaa gcc ccc      528
Gly Tyr Asn Tyr Val Ser Trp Tyr Gln Gln His Pro Gly Lys Ala Pro
                165                 170                 175

aaa ctc atg att tat gaa gtc agt aat cgg ccc tca ggg gtt tct aat      576
Lys Leu Met Ile Tyr Glu Val Ser Asn Arg Pro Ser Gly Val Ser Asn
            180                 185                 190

cgc ttc tct ggc tcc aag tct ggc agc acg gcc tcc ctg acc atc tct      624
Arg Phe Ser Gly Ser Lys Ser Gly Ser Thr Ala Ser Leu Thr Ile Ser
        195                 200                 205

ggg ctc cag gct gag gac gag gct gat tat tac tgc gtc tca tat aca      672
Gly Leu Gln Ala Glu Asp Glu Ala Asp Tyr Tyr Cys Val Ser Tyr Thr
    210                 215                 220

agc aga aac act tat gtc ttc gga tcc ggg acc cag ctc acc gtt tta      720
Ser Arg Asn Thr Tyr Val Phe Gly Ser Gly Thr Gln Leu Thr Val Leu
225                 230                 235                 240

ggt gcg gcc gcg a                                                    733
```

Gly Ala Ala Ala

<210> SEQ ID NO 33
<211> LENGTH: 244
<212> TYPE: PRT
<213> ORGANISM: Escherichia coli

<400> SEQUENCE: 33

Glu Val Gln Leu Leu Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Gly Gln Glu Ala His Gly Asp Gly Met Asp Val Trp Gly Gln Gly
100 105 110

Thr Thr Val Thr Val Ser Ser Val Glu Arg Gly Gly Ser Gly Gly Gly
115 120 125

Gly Ser Gln Ser Ala Leu Thr Gln Pro Ala Ser Ala Ser Gly Ser Pro
130 135 140

Gly Gln Ser Ile Thr Ile Ser Cys Thr Gly Thr Ser Gly Asp Val Gly
145 150 155 160

Gly Tyr Asn Tyr Val Ser Trp Tyr Gln Gln His Pro Gly Lys Ala Pro
165 170 175

Lys Leu Met Ile Tyr Glu Val Ser Asn Arg Pro Ser Gly Val Ser Asn
180 185 190

Arg Phe Ser Gly Ser Lys Ser Gly Ser Thr Ala Ser Leu Thr Ile Ser
195 200 205

Gly Leu Gln Ala Glu Asp Glu Ala Asp Tyr Tyr Cys Val Ser Tyr Thr
210 215 220

Ser Arg Asn Thr Tyr Val Phe Gly Ser Gly Thr Gln Leu Thr Val Leu
225 230 235 240

Gly Ala Ala Ala

<210> SEQ ID NO 34
<211> LENGTH: 372
<212> TYPE: DNA
<213> ORGANISM: Escherichia coli
<220> FEATURE:
<221> NAME/KEY: CDS
<222> LOCATION: (1)..(372)

<400> SEQUENCE: 34 gag gtg cag ctg ttg cag tct ggg gct gag gtg aag aag cct ggg gcc 48
Glu Val Gln Leu Leu Gln Ser Gly Ala Glu Val Lys Lys Pro Gly Ala
1 5 10 15 tca gtg aag gtc tcc tgc aag gct tct gga tac acc ttc acc ggc tcc 96
Ser Val Lys Val Ser Cys Lys Ala Ser Gly Tyr Thr Phe Thr Gly Ser
20 25 30 tat att cac tgg gtg cga cag gcc cct gga caa ggg ctt gag tgg atg 144
Tyr Ile His Trp Val Arg Gln Ala Pro Gly Gln Gly Leu Glu Trp Met
35 40 45

```
gga cgg atg aac cct aac agt ggt gac aca aac tat gca cag aag ttt      192
Gly Arg Met Asn Pro Asn Ser Gly Asp Thr Asn Tyr Ala Gln Lys Phe
    50                  55                  60

cag ggc cgg gtc acc atg acc agg gac acg tcc atc agc aca gcc tac      240
Gln Gly Arg Val Thr Met Thr Arg Asp Thr Ser Ile Ser Thr Ala Tyr
65                  70                  75                  80

atg gag ctg agc agg ctg aga tct gac gac acg gcc gtg tac tac tgt      288
Met Glu Leu Ser Arg Leu Arg Ser Asp Asp Thr Ala Val Tyr Tyr Cys
                85                  90                  95

gcg acg gag gga gtg gct tta cgt ccc ggt gct ttt gat ttc tgg ggc      336
Ala Thr Glu Gly Val Ala Leu Arg Pro Gly Ala Phe Asp Phe Trp Gly
            100                 105                 110

caa ggg acc cag ctc acc gtt tta ggt gcg gcc gca                      372
Gln Gly Thr Gln Leu Thr Val Leu Gly Ala Ala Ala
        115                 120


<210> SEQ ID NO 35
<211> LENGTH: 124
<212> TYPE: PRT
<213> ORGANISM: Escherichia coli

<400> SEQUENCE: 35

Glu Val Gln Leu Leu Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Tyr Ile His Trp Val Arg Gln Ala Pro Gly Gln Gly Leu Glu Trp Met
        35                  40                  45

Gly Arg Met Asn Pro Asn Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Thr Glu Gly Val Ala Leu Arg Pro Gly Ala Phe Asp Phe Trp Gly
            100                 105                 110

Gln Gly Thr Gln Leu Thr Val Leu Gly Ala Ala Ala
        115                 120


<210> SEQ ID NO 36
<211> LENGTH: 756
<212> TYPE: DNA
<213> ORGANISM: Escherichia coli
<220> FEATURE:
<221> NAME/KEY: CDS
<222> LOCATION: (1)..(756)

<400> SEQUENCE: 36

gag gag gtg cag ctg gtg gag tct ggg gga ggc ttg gtc cag cct ggg       48
Glu Glu Val Gln Leu Val Glu Ser Gly Gly Gly Leu Val Gln Pro Gly
1               5                   10                  15

ggg tcc ctg aga ctc tcc tgt gca gcc tct gga ttc acc gtc agt agc       96
Gly Ser Leu Arg Leu Ser Cys Ala Ala Ser Gly Phe Thr Val Ser Ser
            20                  25                  30

aac tac atg agc tgg gtc cgc cag gct cca ggg aag ggg ctg gag tgg      144
Asn Tyr Met Ser Trp Val Arg Gln Ala Pro Gly Lys Gly Leu Glu Trp
        35                  40                  45

gtc tca gtt gtt tat agc ggt ggt agc aca tac tac gca gac tcc gtg      192
Val Ser Val Val Tyr Ser Gly Gly Ser Thr Tyr Tyr Ala Asp Ser Val
    50                  55                  60
```

```
aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctt caa atg aac agc ctg aga gct gag gac acg gct gtg tat tac tgt      288
Leu Gln Met Asn Ser Leu Arg Ala Glu Asp Thr Ala Val Tyr Tyr Cys
                85                  90                  95

gcg aga gac cta ggg ggg act aca gtt tgg cgc tac tac ggt atg gac      336
Ala Arg Asp Leu Gly Gly Thr Thr Val Trp Arg Tyr Tyr Gly Met Asp
            100                 105                 110

gtc tgg ggc caa ggg acc acg gtc acc gtc tcc tca ggt gga ggc ggt      384
Val Trp Gly Gln Gly Thr Thr Val Thr Val Ser Ser Gly Gly Gly Gly
        115                 120                 125

tca ggc gga ggt ggc tct ggc ggt ggc gga tcg tcc tat gtg ctg act      432
Ser Gly Gly Gly Gly Ser Gly Gly Gly Gly Ser Ser Tyr Val Leu Thr
    130                 135                 140

cag cca ccc tcg gtg tca gtg gcc cca gga aag acg gcc acg att acc      480
Gln Pro Pro Ser Val Ser Val Ala Pro Gly Lys Thr Ala Thr Ile Thr
145                 150                 155                 160

tgt gcg gga aac aat ata gga agt aac agt gta tac tgg tac cag cag      528
Cys Ala Gly Asn Asn Ile Gly Ser Asn Ser Val Tyr Trp Tyr Gln Gln
                165                 170                 175

aaa cca ggc ctg gcc cct gta ctg gtc gtc tat gat gat aga gac cgg      576
Lys Pro Gly Leu Ala Pro Val Leu Val Val Tyr Asp Asp Arg Asp Arg
            180                 185                 190

ccc tca ggg atc cct ggg cga ttc tct ggc tcc aaa tcc ggg aac acg      624
Pro Ser Gly Ile Pro Gly Arg Phe Ser Gly Ser Lys Ser Gly Asn Thr
        195                 200                 205

gcc acc ctg acc atc agc agg gtc gag gcc ggg gat gag gcc gac tat      672
Ala Thr Leu Thr Ile Ser Arg Val Glu Ala Gly Asp Glu Ala Asp Tyr
    210                 215                 220

tct tgt cag gtg tgg gat cct agt agt gat cac ctc tat gtc ttc gga      720
Ser Cys Gln Val Trp Asp Pro Ser Ser Asp His Leu Tyr Val Phe Gly
225                 230                 235                 240

act ggg acc cag ctc acc gtt tta ggt gcg gcc gca                      756
Thr Gly Thr Gln Leu Thr Val Leu Gly Ala Ala Ala
                245                 250


<210> SEQ ID NO 37
<211> LENGTH: 252
<212> TYPE: PRT
<213> ORGANISM: Escherichia coli

<400> SEQUENCE: 37

Glu Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Val Ser Ser
            20                  25                  30

Asn Tyr Met Ser Trp Val Arg Gln Ala Pro Gly Lys Gly Leu Glu Trp
        35                  40                  45

Val Ser Val Val Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Gly Thr Thr Val Trp Arg Tyr Tyr Gly Met Asp
            100                 105                 110

Val Trp Gly Gln Gly Thr Thr Val Thr Val Ser Ser Gly Gly Gly Gly
```

```
        115                 120                 125

Ser Gly Gly Gly Gly Ser Gly Gly Gly Gly Ser Ser Tyr Val Leu Thr
    130                 135                 140

Gln Pro Pro Ser Val Ser Val Ala Pro Gly Lys Thr Ala Thr Ile Thr
145                 150                 155                 160

Cys Ala Gly Asn Asn Ile Gly Ser Asn Ser Val Tyr Trp Tyr Gln Gln
                165                 170                 175

Lys Pro Gly Leu Ala Pro Val Leu Val Val Tyr Asp Asp Arg Asp Arg
            180                 185                 190

Pro Ser Gly Ile Pro Gly Arg Phe Ser Gly Ser Lys Ser Gly Asn Thr
        195                 200                 205

Ala Thr Leu Thr Ile Ser Arg Val Glu Ala Gly Asp Glu Ala Asp Tyr
    210                 215                 220

Ser Cys Gln Val Trp Asp Pro Ser Ser Asp His Leu Tyr Val Phe Gly
225                 230                 235                 240

Thr Gly Thr Gln Leu Thr Val Leu Gly Ala Ala Ala
                245                 250


<210> SEQ ID NO 38
<211> LENGTH: 735
<212> TYPE: DNA
<213> ORGANISM: Escherichia coli
<220> FEATURE:
<221> NAME/KEY: CDS
<222> LOCATION: (1)..(735)

<400> SEQUENCE: 38

gag gag gtg cag ctg gtg gag tct gga gga gac ttg atc cag cct ggg       48
Glu Glu Val Gln Leu Val Glu Ser Gly Gly Asp Leu Ile Gln Pro Gly
1               5                   10                  15

ggg tcc ctg aga ctc tcc tgt gca gcc tct ggg ttt acc gtc ggt agc       96
Gly Ser Leu Arg Leu Ser Cys Ala Ala Ser Gly Phe Thr Val Gly Ser
            20                  25                  30

aac tac atg agc tgg gtc cgc cag gct cca ggg aag ggg ctg gaa tgg      144
Asn Tyr Met Ser Trp Val Arg Gln Ala Pro Gly Lys Gly Leu Glu Trp
        35                  40                  45

gtc tca gtt att tat agc ggt ggt agt aca tac tac gca gac tcc gtg      192
Val Ser Val Ile Tyr Ser Gly Gly Ser Thr Tyr Tyr Ala Asp Ser Val
    50                  55                  60

aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
65                  70                  75                  80

ctt caa atg aac agc ctg aga gcc gag gac acg gcc gtg tat tac tgt      288
Leu Gln Met Asn Ser Leu Arg Ala Glu Asp Thr Ala Val Tyr Tyr Cys
                85                  90                  95

gtg aga gat agg ggt gat gct ttt gat atc tgg ggc caa ggg aca atg      336
Val Arg Asp Arg Gly Asp Ala Phe Asp Ile Trp Gly Gln Gly Thr Met
            100                 105                 110

gtc acc gtc tct tca ggt gga ggc gtt cca ggc gga ggt ggc tct ggc      384
Val Thr Val Ser Ser Gly Gly Gly Val Pro Gly Gly Gly Gly Ser Gly
        115                 120                 125

ggt ggc gga tcg tcc tat gcg ctg act cag cca ccc tcg gtg tca gtg      432
Gly Gly Gly Ser Ser Tyr Ala Leu Thr Gln Pro Pro Ser Val Ser Val
    130                 135                 140

gcc cca gga aag acg gcc acg att acc tgt gcg gga aac aat ata gga      480
Ala Pro Gly Lys Thr Ala Thr Ile Thr Cys Ala Gly Asn Asn Ile Gly
145                 150                 155                 160

agt aac agt gta tac tgg tac cag cag aaa cca ggc ctg gcc cct gta      528
Ser Asn Ser Val Tyr Trp Tyr Gln Gln Lys Pro Gly Leu Ala Pro Val
```

```
                165                 170                 175

ctg gtc gtc tat gat gat agc gac cgg ccc tca ggg atg tct gag cga      576
Leu Val Val Tyr Asp Asp Ser Asp Arg Pro Ser Gly Met Ser Glu Arg
            180                 185                 190

ttc tct ggc tcc aaa tcc ggg aac acg gcc acc ctg acc atc agc agg      624
Phe Ser Gly Ser Lys Ser Gly Asn Thr Ala Thr Leu Thr Ile Ser Arg
        195                 200                 205

gtc gag gcc ggg gat gag gcc gac tat tct tgt cag gtg tgg gat cct      672
Val Glu Ala Gly Asp Glu Ala Asp Tyr Ser Cys Gln Val Trp Asp Pro
    210                 215                 220

agt agt gat cac ctc tat gtc ttc gga act ggg acc cag ctc acc gtt      720
Ser Ser Asp His Leu Tyr Val Phe Gly Thr Gly Thr Gln Leu Thr Val
225                 230                 235                 240

tta ggt gcg gcc gca                                                  735
Leu Gly Ala Ala Ala
                245


<210> SEQ ID NO 39
<211> LENGTH: 245
<212> TYPE: PRT
<213> ORGANISM: Escherichia coli

<400> SEQUENCE: 39

Glu Glu Val Gln Leu Val Glu Ser Gly Gly Asp Leu Ile Gln Pro Gly
1               5                   10                  15

Gly Ser Leu Arg Leu Ser Cys Ala Ala Ser Gly Phe Thr Val Gly Ser
            20                  25                  30

Asn Tyr Met Ser Trp Val Arg Gln Ala Pro Gly Lys Gly Leu Glu Trp
        35                  40                  45

Val Ser Val Ile Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Arg Gly Asp Ala Phe Asp Ile Trp Gly Gln Gly Thr Met
            100                 105                 110

Val Thr Val Ser Ser Gly Gly Gly Val Pro Gly Gly Gly Gly Ser Gly
        115                 120                 125

Gly Gly Gly Ser Ser Tyr Ala Leu Thr Gln Pro Pro Ser Val Ser Val
    130                 135                 140

Ala Pro Gly Lys Thr Ala Thr Ile Thr Cys Ala Gly Asn Asn Ile Gly
145                 150                 155                 160

Ser Asn Ser Val Tyr Trp Tyr Gln Gln Lys Pro Gly Leu Ala Pro Val
                165                 170                 175

Leu Val Val Tyr Asp Asp Ser Asp Arg Pro Ser Gly Met Ser Glu Arg
            180                 185                 190

Phe Ser Gly Ser Lys Ser Gly Asn Thr Ala Thr Leu Thr Ile Ser Arg
        195                 200                 205

Val Glu Ala Gly Asp Glu Ala Asp Tyr Ser Cys Gln Val Trp Asp Pro
    210                 215                 220

Ser Ser Asp His Leu Tyr Val Phe Gly Thr Gly Thr Gln Leu Thr Val
225                 230                 235                 240

Leu Gly Ala Ala Ala
                245
```

<210> SEQ ID NO 40
<211> LENGTH: 761
<212> TYPE: DNA
<213> ORGANISM: Escherichia coli
<220> FEATURE:
<221> NAME/KEY: CDS
<222> LOCATION: (1)..(759)

<400> SEQUENCE: 40

```
atg gag gag gtg cag ctg gtg gag tct ggg gga gcc ttg gta cag cct       48
Met Glu Glu Val Gln Leu Val Glu Ser Gly Gly Ala Leu Val Gln Pro
1               5                   10                  15

ggg ggg tcc ctg aga atc tct tgt gta ggc tct gga ttc acc ttc cga       96
Gly Gly Ser Leu Arg Ile Ser Cys Val Gly Ser Gly Phe Thr Phe Arg
            20                  25                  30

cag cat gac atg agc tgg gtc cgc cag gct cct ggg aag ggg ctg gag      144
Gln His Asp Met Ser Trp Val Arg Gln Ala Pro Gly Lys Gly Leu Glu
        35                  40                  45

tgg gtc gca act ata agt gga agt gct gat aac aca ttt tac gca gac      192
Trp Val Ala Thr Ile Ser Gly Ser Ala Asp Asn Thr Phe Tyr Ala Asp
    50                  55                  60

tcc gtg aag ggc cgg ttc acc atc tcc aga gac aat tcc aag aac acg      240
Ser Val Lys Gly Arg Phe Thr Ile Ser Arg Asp Asn Ser Lys Asn Thr
65                  70                  75                  80

ctg tat ctg cag atg aac acc ctg aaa gcc gac gac acg gcc gta tat      288
Leu Tyr Leu Gln Met Asn Thr Leu Lys Ala Asp Asp Thr Ala Val Tyr
                85                  90                  95

tac tgt gcg aag aaa tat ata gaa cca ggt gct acc cga ttt gac tac      336
Tyr Cys Ala Lys Lys Tyr Ile Glu Pro Gly Ala Thr Arg Phe Asp Tyr
            100                 105                 110

tgg ggc cag aga acc ctg gtc acc gtc tcc tca ggt gga ggc ggt tca      384
Trp Gly Gln Arg Thr Leu Val Thr Val Ser Ser Gly Gly Gly Gly Ser
        115                 120                 125

ggc gga ggt ggc tct ggc ggt ggc gga tcg gat gtt gtg atg act cag      432
Gly Gly Gly Gly Ser Gly Gly Gly Gly Ser Asp Val Val Met Thr Gln
    130                 135                 140

tct cca ctc tct ctg tcc gtc acc cct gga cag ccg gcc tcc atc tcc      480
Ser Pro Leu Ser Leu Ser Val Thr Pro Gly Gln Pro Ala Ser Ile Ser
145                 150                 155                 160

tgc aag tct agt cag agc ctc ctg cat agt gat gga aag acc tat ttg      528
Cys Lys Ser Ser Gln Ser Leu Leu His Ser Asp Gly Lys Thr Tyr Leu
                165                 170                 175

tat tgg tac ctg cag aag cca ggc cag tct cca cag ctc ctg atc tat      576
Tyr Trp Tyr Leu Gln Lys Pro Gly Gln Ser Pro Gln Leu Leu Ile Tyr
            180                 185                 190

gaa gtt tcc aac cgg ttc tct gga gtg cca gat agg ttc agt ggc agc      624
Glu Val Ser Asn Arg Phe Ser Gly Val Pro Asp Arg Phe Ser Gly Ser
        195                 200                 205

ggg tca ggg aca gat ttc aca ctg aaa atc agc cgg gtg gag gct gag      672
Gly Ser Gly Thr Asp Phe Thr Leu Lys Ile Ser Arg Val Glu Ala Glu
    210                 215                 220

gat gtt ggg gtt tat tac tgc atg caa agt ata cag ctc ccg atc acc      720
Asp Val Gly Val Tyr Tyr Cys Met Gln Ser Ile Gln Leu Pro Ile Thr
225                 230                 235                 240

ttc ggc caa ggg aca cga ctg gag att aaa cgt gcg gcc gc               761
Phe Gly Gln Gly Thr Arg Leu Glu Ile Lys Arg Ala Ala
                245                 250
```

<210> SEQ ID NO 41
<211> LENGTH: 253
<212> TYPE: PRT
<213> ORGANISM: Escherichia coli

<400> SEQUENCE: 41

Met Glu Glu Val Gln Leu Val Glu Ser Gly Gly Ala Leu Val Gln Pro
1 5 10 15

Gly Gly Ser Leu Arg Ile Ser Cys Val Gly Ser Gly Phe Thr Phe Arg
20 25 30

Gln His Asp Met Ser Trp Val Arg Gln Ala Pro Gly Lys Gly Leu Glu
35 40 45

Trp Val Ala Thr Ile Ser Gly Ser Ala Asp Asn Thr Phe Tyr Ala Asp
50 55 60

Ser Val Lys Gly Arg Phe Thr Ile Ser Arg Asp Asn Ser Lys Asn Thr
65 70 75 80

Leu Tyr Leu Gln Met Asn Thr Leu Lys Ala Asp Asp Thr Ala Val Tyr
85 90 95

Tyr Cys Ala Lys Lys Tyr Ile Glu Pro Gly Ala Thr Arg Phe Asp Tyr
100 105 110

Trp Gly Gln Arg Thr Leu Val Thr Val Ser Ser Gly Gly Gly Gly Ser
115 120 125

Gly Gly Gly Gly Ser Gly Gly Gly Gly Ser Asp Val Val Met Thr Gln
130 135 140

Ser Pro Leu Ser Leu Ser Val Thr Pro Gly Gln Pro Ala Ser Ile Ser
145 150 155 160

Cys Lys Ser Ser Gln Ser Leu Leu His Ser Asp Gly Lys Thr Tyr Leu
165 170 175

Tyr Trp Tyr Leu Gln Lys Pro Gly Gln Ser Pro Gln Leu Leu Ile Tyr
180 185 190

Glu Val Ser Asn Arg Phe Ser Gly Val Pro Asp Arg Phe Ser Gly Ser
195 200 205

Gly Ser Gly Thr Asp Phe Thr Leu Lys Ile Ser Arg Val Glu Ala Glu
210 215 220

Asp Val Gly Val Tyr Tyr Cys Met Gln Ser Ile Gln Leu Pro Ile Thr
225 230 235 240

Phe Gly Gln Gly Thr Arg Leu Glu Ile Lys Arg Ala Ala
245 250

<210> SEQ ID NO 42
<211> LENGTH: 765
<212> TYPE: DNA
<213> ORGANISM: Escherichia coli
<220> FEATURE:
<221> NAME/KEY: CDS
<222> LOCATION: (1)..(765)

<400> SEQUENCE: 42 gag cag gtg cag ctg gtg cag tct ggg gga ggc gtg gtc cag cct ggg 48
Glu Gln Val Gln Leu Val Gln Ser Gly Gly Gly Val Val Gln Pro Gly
1 5 10 15 agg tcc ctg aga ctc tcc tgt gca gcc tct gga ttc agc ttc agt aac 96
Arg Ser Leu Arg Leu Ser Cys Ala Ala Ser Gly Phe Ser Phe Ser Asn
20 25 30 tat gtt atg cac tgg gtc cgc cag gct cca ggc aag ggg ctg gag tgg 144
Tyr Val Met His Trp Val Arg Gln Ala Pro Gly Lys Gly Leu Glu Trp
35 40 45 gtg gca gtt ata tca cat gat gga agc aat aaa tac tac gca gac tcc 192
Val Ala Val Ile Ser His Asp Gly Ser Asn Lys Tyr Tyr Ala Asp Ser
50 55 60 gtg aag ggc cga ttc acc atc tcc aga gac aat tcc aag aac acg cta 240

```
Val Lys Gly Arg Phe Thr Ile Ser Arg Asp Asn Ser Lys Asn Thr Leu
65                  70                  75                  80

tat ctg caa atg aaa agc ctg aga cct gag gac acg gct gtg tat tac      288
Tyr Leu Gln Met Lys Ser Leu Arg Pro Glu Asp Thr Ala Val Tyr Tyr
                85                  90                  95

tgt gcg aga agt agt ggc tgg tac ctt ctc ttt gat gct ttt gat atc      336
Cys Ala Arg Ser Ser Gly Trp Tyr Leu Leu Phe Asp Ala Phe Asp Ile
            100                 105                 110

tgg ggc caa ggg aca atg gtc acc gtc tct tca ggt gga ggc ggt tca      384
Trp Gly Gln Gly Thr Met Val Thr Val Ser Ser Gly Gly Gly Gly Ser
        115                 120                 125

ggc gga ggt ggc tct ggc ggt ggc gga tcg gac atc cag atg acc cag      432
Gly Gly Gly Gly Ser Gly Gly Gly Gly Ser Asp Ile Gln Met Thr Gln
    130                 135                 140

tct cca gac tcc ctg cct gtg tct ctg ggc gag agg gcc acc atc aac      480
Ser Pro Asp Ser Leu Pro Val Ser Leu Gly Glu Arg Ala Thr Ile Asn
145                 150                 155                 160

tgc agg tcc agc cag agt gtt tta tac agc tcc aac aat aag aac tac      528
Cys Arg Ser Ser Gln Ser Val Leu Tyr Ser Ser Asn Asn Lys Asn Tyr
                165                 170                 175

tta gct tgg tac cag cag aaa cca gga cag cct cct aag ctg ctc att      576
Leu Ala Trp Tyr Gln Gln Lys Pro Gly Gln Pro Pro Lys Leu Leu Ile
            180                 185                 190

tac tgg gca tct acc cgg gaa tcc ggt gtc cct gac cga ttc agt ggc      624
Tyr Trp Ala Ser Thr Arg Glu Ser Gly Val Pro Asp Arg Phe Ser Gly
        195                 200                 205

agc ggg tct ggg aca gat ttc act ctc acc atc agc agc ctg cag gct      672
Ser Gly Ser Gly Thr Asp Phe Thr Leu Thr Ile Ser Ser Leu Gln Ala
    210                 215                 220

gaa gat gtg gca gtt tat tac tgt cag caa tat tat agg att ccg tgg      720
Glu Asp Val Ala Val Tyr Tyr Cys Gln Gln Tyr Tyr Arg Ile Pro Trp
225                 230                 235                 240

acg ttc ggc caa ggg acg aag gtg gaa atc aaa cgt gcg gcc gca          765
Thr Phe Gly Gln Gly Thr Lys Val Glu Ile Lys Arg Ala Ala Ala
                245                 250                 255


<210> SEQ ID NO 43
<211> LENGTH: 255
<212> TYPE: PRT
<213> ORGANISM: Escherichia coli

<400> SEQUENCE: 43

Glu Gln Val Gln Leu Val Gln Ser Gly Gly Gly Val Val Gln Pro Gly
1               5                   10                  15

Arg Ser Leu Arg Leu Ser Cys Ala Ala Ser Gly Phe Ser Phe Ser Asn
            20                  25                  30

Tyr Val Met His Trp Val Arg Gln Ala Pro Gly Lys Gly Leu Glu Trp
        35                  40                  45

Val Ala Val Ile Ser His Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Lys Ser Leu Arg Pro Glu Asp Thr Ala Val Tyr Tyr
                85                  90                  95

Cys Ala Arg Ser Ser Gly Trp Tyr Leu Leu Phe Asp Ala Phe Asp Ile
            100                 105                 110

Trp Gly Gln Gly Thr Met Val Thr Val Ser Ser Gly Gly Gly Gly Ser
        115                 120                 125
```

```
Gly Gly Gly Gly Ser Gly Gly Gly Gly Ser Asp Ile Gln Met Thr Gln
    130                 135                 140

Ser Pro Asp Ser Leu Pro Val Ser Leu Gly Glu Arg Ala Thr Ile Asn
145                 150                 155                 160

Cys Arg Ser Ser Gln Ser Val Leu Tyr Ser Ser Asn Asn Lys Asn Tyr
                165                 170                 175

Leu Ala Trp Tyr Gln Gln Lys Pro Gly Gln Pro Pro Lys Leu Leu Ile
            180                 185                 190

Tyr Trp Ala Ser Thr Arg Glu Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Tyr Tyr Arg Ile Pro Trp
225                 230                 235                 240

Thr Phe Gly Gln Gly Thr Lys Val Glu Ile Lys Arg Ala Ala Ala
                245                 250                 255


<210> SEQ ID NO 44
<211> LENGTH: 759
<212> TYPE: DNA
<213> ORGANISM: Escherichia coli
<220> FEATURE:
<221> NAME/KEY: CDS
<222> LOCATION: (1)..(759)

<400> SEQUENCE: 44

gag gag gtg cag ctg ttg cag tct ggg gga ggt gtg gta cgg cct ggg       48
Glu Glu Val Gln Leu Leu Gln Ser Gly Gly Gly Val Val Arg Pro Gly
1               5                   10                  15

ggg tcc ctg aga ctc tcc tgt gca gcc tct gga ttc acc ttt gat gat       96
Gly Ser Leu Arg Leu Ser Cys Ala Ala Ser Gly Phe Thr Phe Asp Asp
            20                  25                  30

tat ggc atg acc tgg gtc cgc cag gct cca ggg aag ggg ctg gag tgg      144
Tyr Gly Met Thr Trp Val Arg Gln Ala Pro Gly Lys Gly Leu Glu Trp
        35                  40                  45

gtc tca gct att agt ggt agt ggt ggt agc aca tac tac gca gac tcc      192
Val Ser Ala Ile Ser Gly Ser Gly Gly Ser Thr Tyr Tyr Ala Asp Ser
    50                  55                  60

gtg aag ggc cgg ttc gcc atc tcc aga gac aat tcc aag aac acg ctg      240
Val Lys Gly Arg Phe Ala Ile Ser Arg Asp Asn Ser Lys Asn Thr Leu
65                  70                  75                  80

tat ctg caa atg aac agc ctg aga gcc gag gac acg gcc gta tat tac      288
Tyr Leu Gln Met Asn Ser Leu Arg Ala Glu Asp Thr Ala Val Tyr Tyr
                85                  90                  95

tgt gcg aaa tct cgc tac tat gat agt agt ggt tat tac tac acc gtg      336
Cys Ala Lys Ser Arg Tyr Tyr Asp Ser Ser Gly Tyr Tyr Tyr Thr Val
            100                 105                 110

cga cct gat gct ttt gat atc tgg ggc caa ggg gca atg gtc acc gtc      384
Arg Pro Asp Ala Phe Asp Ile Trp Gly Gln Gly Ala Met Val Thr Val
        115                 120                 125

tct tca ggt gga ggc ggt gga ggt ggc tct ggc ggt ggc gga tcg tct      432
Ser Ser Gly Gly Gly Gly Gly Gly Ser Gly Gly Gly Gly Ser Ser
    130                 135                 140

tct gag ctg act caa cca ccc tca gtg tcc gtg tcc cca gga cag aca      480
Ser Glu Leu Thr Gln Pro Pro Ser Val Ser Val Ser Pro Gly Gln Thr
145                 150                 155                 160

gcc atc atc acc tgc tct gga gat aaa ttg ggg gat aaa tat gct tcc      528
Ala Ile Ile Thr Cys Ser Gly Asp Lys Leu Gly Asp Lys Tyr Ala Ser
                165                 170                 175
```

```
tgg tat cag cac agg cca ggc cag tcg cct gtc ttg gtc atc tat cag      576
Trp Tyr Gln His Arg Pro Gly Gln Ser Pro Val Leu Val Ile Tyr Gln
            180                 185                 190

gat tcc agg cgg ccc tca gac atc cct gag cga ttc tct ggc tcc aac      624
Asp Ser Arg Arg Pro Ser Asp Ile Pro Glu Arg Phe Ser Gly Ser Asn
        195                 200                 205

tct ggg aac aca gcc act ctg acc atc acc gag gcc cag gct ttg gat      672
Ser Gly Asn Thr Ala Thr Leu Thr Ile Thr Glu Ala Gln Ala Leu Asp
    210                 215                 220

gag gct gac tat tat tgt cag gcc tgg gcc ggc aga tct gtg gtc ttc      720
Glu Ala Asp Tyr Tyr Cys Gln Ala Trp Ala Gly Arg Ser Val Val Phe
225                 230                 235                 240

ggc ggg ggg acc cag ctc acc gtt tta ggt gcg gcc gca                  759
Gly Gly Gly Thr Gln Leu Thr Val Leu Gly Ala Ala Ala
                245                 250


<210> SEQ ID NO 45
<211> LENGTH: 253
<212> TYPE: PRT
<213> ORGANISM: Escherichia coli

<400> SEQUENCE: 45

Glu Glu Val Gln Leu Leu Gln Ser Gly Gly Gly Val Val Arg Pro Gly
1               5                   10                  15

Gly Ser Leu Arg Leu Ser Cys Ala Ala Ser Gly Phe Thr Phe Asp Asp
            20                  25                  30

Tyr Gly Met Thr Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Ala Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Ser Arg Tyr Tyr Asp Ser Ser Gly Tyr Tyr Tyr Thr Val
            100                 105                 110

Arg Pro Asp Ala Phe Asp Ile Trp Gly Gln Gly Ala Met Val Thr Val
        115                 120                 125

Ser Ser Gly Gly Gly Gly Gly Gly Gly Ser Gly Gly Gly Gly Ser Ser
    130                 135                 140

Ser Glu Leu Thr Gln Pro Pro Ser Val Ser Val Ser Pro Gly Gln Thr
145                 150                 155                 160

Ala Ile Ile Thr Cys Ser Gly Asp Lys Leu Gly Asp Lys Tyr Ala Ser
                165                 170                 175

Trp Tyr Gln His Arg Pro Gly Gln Ser Pro Val Leu Val Ile Tyr Gln
            180                 185                 190

Asp Ser Arg Arg Pro Ser Asp Ile Pro Glu Arg Phe Ser Gly Ser Asn
        195                 200                 205

Ser Gly Asn Thr Ala Thr Leu Thr Ile Thr Glu Ala Gln Ala Leu Asp
    210                 215                 220

Glu Ala Asp Tyr Tyr Cys Gln Ala Trp Ala Gly Arg Ser Val Val Phe
225                 230                 235                 240

Gly Gly Gly Thr Gln Leu Thr Val Leu Gly Ala Ala Ala
                245                 250


<210> SEQ ID NO 46
<211> LENGTH: 768
```

<212> TYPE: DNA
<213> ORGANISM: Escherichia coli
<220> FEATURE:
<221> NAME/KEY: CDS
<222> LOCATION: (1)..(768)

<400> SEQUENCE: 46

```
gag gag gtg cag ctg ttg cag tct ggg gcg gag gtg aag aag cct ggg       48
Glu Glu Val Gln Leu Leu Gln Ser Gly Ala Glu Val Lys Lys Pro Gly
1               5                   10                  15

gcc tca gtg aga gtt tcc tgc cag gca tct gga tac aca ttc agc agg       96
Ala Ser Val Arg Val Ser Cys Gln Ala Ser Gly Tyr Thr Phe Ser Arg
            20                  25                  30

tac cat atg cac tgg gtg cga cag gcc cct gga caa ggg ctt gag tgg      144
Tyr His Met His Trp Val Arg Gln Ala Pro Gly Gln Gly Leu Glu Trp
        35                  40                  45

atg gga gtg atc gac ccc aat agt ggt aga gta agt tac tca cag aag      192
Met Gly Val Ile Asp Pro Asn Ser Gly Arg Val Ser Tyr Ser Gln Lys
    50                  55                  60

ttc cag gac aga gtc acc atg acc agg gac acg ttc acg agc aca gta      240
Phe Gln Asp Arg Val Thr Met Thr Arg Asp Thr Phe Thr Ser Thr Val
65                  70                  75                  80

tac atg gag ctg aac agc ctg aga tct gag gac acg gcc gtt tat tat      288
Tyr Met Glu Leu Asn Ser Leu Arg Ser Glu Asp Thr Ala Val Tyr Tyr
                85                  90                  95

tgt gcg aga gat cga gga tat tgt aat ggt ggc agg tgc ttt atg gat      336
Cys Ala Arg Asp Arg Gly Tyr Cys Asn Gly Gly Arg Cys Phe Met Asp
            100                 105                 110

gca ttt gac tac tgg ggc cag ggg acc acg gtc acc gtc tcc tca ggt      384
Ala Phe Asp Tyr Trp Gly Gln Gly Thr Thr Val Thr Val Ser Ser Gly
        115                 120                 125

gga ggc ggt tca ggc gga ggt ggc cct ggc ggt ggc gga tcg tcc tat      432
Gly Gly Gly Ser Gly Gly Gly Gly Pro Gly Gly Gly Gly Ser Ser Tyr
    130                 135                 140

gtg ctg act cag cca ccc tca gcg tct ggg gcc ccc gga cag agg gtc      480
Val Leu Thr Gln Pro Pro Ser Ala Ser Gly Ala Pro Gly Gln Arg Val
145                 150                 155                 160

acc atc tct tgt tct gga agc aac tcc aac atc gga cgt aat tgg gta      528
Thr Ile Ser Cys Ser Gly Ser Asn Ser Asn Ile Gly Arg Asn Trp Val
                165                 170                 175

tac tgg tac cag caa ctc cca gga acg gcc ccc aaa ctc ctc atg ttt      576
Tyr Trp Tyr Gln Gln Leu Pro Gly Thr Ala Pro Lys Leu Leu Met Phe
            180                 185                 190

agg aat aat gaa cgg tcc tca ggg gtc cct gac cga ttc tct ggc tcc      624
Arg Asn Asn Glu Arg Ser Ser Gly Val Pro Asp Arg Phe Ser Gly Ser
        195                 200                 205

aag act ggc acc tca gcc tcc ctg gcc atc agt ggg ctc cgg tct gag      672
Lys Thr Gly Thr Ser Ala Ser Leu Ala Ile Ser Gly Leu Arg Ser Glu
    210                 215                 220

gat gag ggt gat tac tac tgt gca tca tgg gat gac agt ctg cat gct      720
Asp Glu Gly Asp Tyr Tyr Cys Ala Ser Trp Asp Asp Ser Leu His Ala
225                 230                 235                 240

tgg gtg ttc ggc ggg ggg acc cag ctc acc gtt tta ggt gcg gcc gca      768
Trp Val Phe Gly Gly Gly Thr Gln Leu Thr Val Leu Gly Ala Ala Ala
                245                 250                 255
```

<210> SEQ ID NO 47
<211> LENGTH: 256
<212> TYPE: PRT
<213> ORGANISM: Escherichia coli

<400> SEQUENCE: 47

```
Glu Glu Val Gln Leu Leu Gln Ser Gly Ala Glu Val Lys Lys Pro Gly
1               5                   10                  15

Ala Ser Val Arg Val Ser Cys Gln Ala Ser Gly Tyr Thr Phe Ser Arg
            20                  25                  30

Tyr His Met His Trp Val Arg Gln Ala Pro Gly Gln Gly Leu Glu Trp
        35                  40                  45

Met Gly Val Ile Asp Pro Asn Ser Gly Arg Val Ser Tyr Ser Gln Lys
    50                  55                  60

Phe Gln Asp Arg Val Thr Met Thr Arg Asp Thr Phe Thr Ser Thr Val
65                  70                  75                  80

Tyr Met Glu Leu Asn Ser Leu Arg Ser Glu Asp Thr Ala Val Tyr Tyr
                85                  90                  95

Cys Ala Arg Asp Arg Gly Tyr Cys Asn Gly Gly Arg Cys Phe Met Asp
            100                 105                 110

Ala Phe Asp Tyr Trp Gly Gln Gly Thr Thr Val Thr Val Ser Ser Gly
        115                 120                 125

Gly Gly Gly Ser Gly Gly Gly Gly Pro Gly Gly Gly Gly Ser Ser Tyr
    130                 135                 140

Val Leu Thr Gln Pro Pro Ser Ala Ser Gly Ala Pro Gly Gln Arg Val
145                 150                 155                 160

Thr Ile Ser Cys Ser Gly Ser Asn Ser Asn Ile Gly Arg Asn Trp Val
                165                 170                 175

Tyr Trp Tyr Gln Gln Leu Pro Gly Thr Ala Pro Lys Leu Leu Met Phe
            180                 185                 190

Arg Asn Asn Glu Arg Ser Ser Gly Val Pro Asp Arg Phe Ser Gly Ser
        195                 200                 205

Lys Thr Gly Thr Ser Ala Ser Leu Ala Ile Ser Gly Leu Arg Ser Glu
    210                 215                 220

Asp Glu Gly Asp Tyr Tyr Cys Ala Ser Trp Asp Asp Ser Leu His Ala
225                 230                 235                 240

Trp Val Phe Gly Gly Gly Thr Gln Leu Thr Val Leu Gly Ala Ala Ala
                245                 250                 255


<210> SEQ ID NO 48
<211> LENGTH: 765
<212> TYPE: DNA
<213> ORGANISM: Escherichia coli
<220> FEATURE:
<221> NAME/KEY: CDS
<222> LOCATION: (1)..(765)

<400> SEQUENCE: 48

gag gag gtg cag ctg gtg gag tct ggg gga aac ttg gtt cag cct ggg       48
Glu Glu Val Gln Leu Val Glu Ser Gly Gly Asn Leu Val Gln Pro Gly
1               5                   10                  15

ggg tcc ctg aga ctc tcc tgt gca gcc tct gga ttc acc ttt agc agt       96
Gly Ser Leu Arg Leu Ser Cys Ala Ala Ser Gly Phe Thr Phe Ser Ser
            20                  25                  30

tat gcc atg agc tgg gtc cgc cag gct cca ggg aag ggg ctg gaa tgg      144
Tyr Ala Met Ser Trp Val Arg Gln Ala Pro Gly Lys Gly Leu Glu Trp
        35                  40                  45

gtc tca gct att agt gct agt ggt ggc acc aca tac tac gca gat tcc      192
Val Ser Ala Ile Ser Ala Ser Gly Gly Thr Thr Tyr Tyr Ala Asp Ser
    50                  55                  60

gtg aag ggc cgg ttc acc atc tcc aga gac aat tcc aag aac acg ctg      240
Val Lys Gly Arg Phe Thr Ile Ser Arg Asp Asn Ser Lys Asn Thr Leu
65                  70                  75                  80
```

```
tat ctt caa atg aac agc ctg aga act gag gac acg gct gtg tat tac      288
Tyr Leu Gln Met Asn Ser Leu Arg Thr Glu Asp Thr Ala Val Tyr Tyr
                85                  90                  95

tgt gcg aga gac agc cgt gca tac agc tat ggt tac ctc tac gtc ttt      336
Cys Ala Arg Asp Ser Arg Ala Tyr Ser Tyr Gly Tyr Leu Tyr Val Phe
            100                 105                 110

gac tac tgg ggc cag ggc acc ctg gtc acc gtc tcc tca ggt gga ggc      384
Asp Tyr Trp Gly Gln Gly Thr Leu Val Thr Val Ser Ser Gly Gly Gly
        115                 120                 125

ggt tca ggc gga ggt ggc tct ggc ggt ggc gga tcg cag tct gcc ctg      432
Gly Ser Gly Gly Gly Gly Ser Gly Gly Gly Gly Ser Gln Ser Ala Leu
    130                 135                 140

act cag cct gcc tcc gtg tct ggg tct cct gga cag tcg atc acc atc      480
Thr Gln Pro Ala Ser Val Ser Gly Ser Pro Gly Gln Ser Ile Thr Ile
145                 150                 155                 160

tcc tgc act gga acc agc aat gat gtt ggg agt tat aac ctt gtc tcc      528
Ser Cys Thr Gly Thr Ser Asn Asp Val Gly Ser Tyr Asn Leu Val Ser
                165                 170                 175

tgg tac caa caa cac cca ggc aaa gcc ccc aaa ctc ctg att tat gag      576
Trp Tyr Gln Gln His Pro Gly Lys Ala Pro Lys Leu Leu Ile Tyr Glu
            180                 185                 190

ggc agt aag cgg ccc tca ggg att tct aat cgc ttc tct ggc tcc aag      624
Gly Ser Lys Arg Pro Ser Gly Ile Ser Asn Arg Phe Ser Gly Ser Lys
        195                 200                 205

tct ggc aac acg gcc tcc ctg acc atc tct ggg ctc cag gct gag gac      672
Ser Gly Asn Thr Ala Ser Leu Thr Ile Ser Gly Leu Gln Ala Glu Asp
    210                 215                 220

gag gct gat tat tac tgc atg tca tat acg agc agt ggc act cct tat      720
Glu Ala Asp Tyr Tyr Cys Met Ser Tyr Thr Ser Ser Gly Thr Pro Tyr
225                 230                 235                 240

gtc ttc gga act ggg acc cag ctc acc gtt tta ggt gcg gcc gca          765
Val Phe Gly Thr Gly Thr Gln Leu Thr Val Leu Gly Ala Ala Ala
                245                 250                 255


<210> SEQ ID NO 49
<211> LENGTH: 255
<212> TYPE: PRT
<213> ORGANISM: Escherichia coli

<400> SEQUENCE: 49

Glu Glu Val Gln Leu Val Glu Ser Gly Gly Asn Leu Val Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
        35                  40                  45

Val Ser Ala Ile Ser Ala Ser Gly Gly Thr Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Thr Glu Asp Thr Ala Val Tyr Tyr
                85                  90                  95

Cys Ala Arg Asp Ser Arg Ala Tyr Ser Tyr Gly Tyr Leu Tyr Val Phe
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ser Ala Leu
    130                 135                 140
```

```
Thr Gln Pro Ala Ser Val Ser Gly Ser Pro Gly Gln Ser Ile Thr Ile
145                 150                 155                 160

Ser Cys Thr Gly Thr Ser Asn Asp Val Gly Ser Tyr Asn Leu Val Ser
                165                 170                 175

Trp Tyr Gln Gln His Pro Gly Lys Ala Pro Lys Leu Leu Ile Tyr Glu
            180                 185                 190

Gly Ser Lys Arg Pro Ser Gly Ile Ser Asn Arg Phe Ser Gly Ser Lys
        195                 200                 205

Ser Gly Asn Thr Ala Ser Leu Thr Ile Ser Gly Leu Gln Ala Glu Asp
    210                 215                 220

Glu Ala Asp Tyr Tyr Cys Met Ser Tyr Thr Ser Ser Gly Thr Pro Tyr
225                 230                 235                 240

Val Phe Gly Thr Gly Thr Gln Leu Thr Val Leu Gly Ala Ala Ala
                245                 250                 255


<210> SEQ ID NO 50
<211> LENGTH: 768
<212> TYPE: DNA
<213> ORGANISM: Escherichia coli
<220> FEATURE:
<221> NAME/KEY: CDS
<222> LOCATION: (1)..(768)

<400> SEQUENCE: 50

gag gag gtg cag ctg gtg gag tct ggg gct gag gtg aag aag cct ggg       48
Glu Glu Val Gln Leu Val Glu Ser Gly Ala Glu Val Lys Lys Pro Gly
1               5                   10                  15

gcc tca gtg aga gtt tcc tgc cag gca tct gga tac aca ttc acc agg       96
Ala Ser Val Arg Val Ser Cys Gln Ala Ser Gly Tyr Thr Phe Thr Arg
            20                  25                  30

tac cat ata cac tgg gtg cga cag gcc cct gga caa ggg ctt gag tgg      144
Tyr His Ile His Trp Val Arg Gln Ala Pro Gly Gln Gly Leu Glu Trp
        35                  40                  45

atg gga gtg atc gac ccc aat agt ggt aga ata agt tac tca cag aag      192
Met Gly Val Ile Asp Pro Asn Ser Gly Arg Ile Ser Tyr Ser Gln Lys
    50                  55                  60

ttc cag gac aga gtc acc atg acc agg gac acg tcc acg agc aca gtc      240
Phe Gln Asp Arg Val Thr Met Thr Arg Asp Thr Ser Thr Ser Thr Val
65                  70                  75                  80

tac atg gag ctg aac agc ctg aga tct gag gac aca gcc att tat tac      288
Tyr Met Glu Leu Asn Ser Leu Arg Ser Glu Asp Thr Ala Ile Tyr Tyr
                85                  90                  95

tgt gcg aga gat cga gga tat tgt aat ggt ggc agg tgc ttt atg gat      336
Cys Ala Arg Asp Arg Gly Tyr Cys Asn Gly Gly Arg Cys Phe Met Asp
            100                 105                 110

gca ttt gac tac tgg ggc cag ggg acc acg gtc acc gtc tcc tca ggt      384
Ala Phe Asp Tyr Trp Gly Gln Gly Thr Thr Val Thr Val Ser Ser Gly
        115                 120                 125

gga ggc ggt tca ggc gga ggt ggc tct ggc ggt ggc gga tcg cag tct      432
Gly Gly Gly Ser Gly Gly Gly Gly Ser Gly Gly Gly Gly Ser Gln Ser
    130                 135                 140

gtg ttg acg cag ccg ccc tca gcg tct ggg acc ccc ggg cag agg gtc      480
Val Leu Thr Gln Pro Pro Ser Ala Ser Gly Thr Pro Gly Gln Arg Val
145                 150                 155                 160

acc atc gct tgt tct gga agc agc tcc aac atc gga att aat act gta      528
Thr Ile Ala Cys Ser Gly Ser Ser Ser Asn Ile Gly Ile Asn Thr Val
                165                 170                 175

aac tgg tac cag cag atc cca gga acg gcc ccc aaa ctc ctc atc tat      576
Asn Trp Tyr Gln Gln Ile Pro Gly Thr Ala Pro Lys Leu Leu Ile Tyr
```

```
            180                 185                 190

aat aat gat cag cgg ccc tca ggg gtc cct gac cga ttc tct ggc tcc      624
Asn Asn Asp Gln Arg Pro Ser Gly Val Pro Asp Arg Phe Ser Gly Ser
        195                 200                 205

aag tct gcc acc tca gcc tcc ctg gcc atc act ggg ctc cag gtt gac      672
Lys Ser Ala Thr Ser Ala Ser Leu Ala Ile Thr Gly Leu Gln Val Asp
    210                 215                 220

gat gag gct gat tat tac tgc cag tcc tat gac agc agc ctg ggt ggt      720
Asp Glu Ala Asp Tyr Tyr Cys Gln Ser Tyr Asp Ser Ser Leu Gly Gly
225                 230                 235                 240

tat gtc ttc gga act ggg acc cag ctc acc gtt tta ggt gcg gcc gca      768
Tyr Val Phe Gly Thr Gly Thr Gln Leu Thr Val Leu Gly Ala Ala Ala
                245                 250                 255


<210> SEQ ID NO 51
<211> LENGTH: 256
<212> TYPE: PRT
<213> ORGANISM: Escherichia coli

<400> SEQUENCE: 51

Glu Glu Val Gln Leu Val Glu Ser Gly Ala Glu Val Lys Lys Pro Gly
1               5                   10                  15

Ala Ser Val Arg Val Ser Cys Gln Ala Ser Gly Tyr Thr Phe Thr Arg
            20                  25                  30

Tyr His Ile His Trp Val Arg Gln Ala Pro Gly Gln Gly Leu Glu Trp
        35                  40                  45

Met Gly Val Ile Asp Pro Asn Ser Gly Arg Ile Ser Tyr Ser Gln Lys
    50                  55                  60

Phe Gln Asp Arg Val Thr Met Thr Arg Asp Thr Ser Thr Ser Thr Val
65                  70                  75                  80

Tyr Met Glu Leu Asn Ser Leu Arg Ser Glu Asp Thr Ala Ile Tyr Tyr
                85                  90                  95

Cys Ala Arg Asp Arg Gly Tyr Cys Asn Gly Gly Arg Cys Phe Met Asp
            100                 105                 110

Ala Phe Asp Tyr Trp Gly Gln Gly Thr Thr Val Thr Val Ser Ser Gly
        115                 120                 125

Gly Gly Gly Ser Gly Gly Gly Gly Ser Gly Gly Gly Gly Ser Gln Ser
    130                 135                 140

Val Leu Thr Gln Pro Pro Ser Ala Ser Gly Thr Pro Gly Gln Arg Val
145                 150                 155                 160

Thr Ile Ala Cys Ser Gly Ser Ser Ser Asn Ile Gly Ile Asn Thr Val
                165                 170                 175

Asn Trp Tyr Gln Gln Ile Pro Gly Thr Ala Pro Lys Leu Leu Ile Tyr
            180                 185                 190

Asn Asn Asp Gln Arg Pro Ser Gly Val Pro Asp Arg Phe Ser Gly Ser
        195                 200                 205

Lys Ser Ala Thr Ser Ala Ser Leu Ala Ile Thr Gly Leu Gln Val Asp
    210                 215                 220

Asp Glu Ala Asp Tyr Tyr Cys Gln Ser Tyr Asp Ser Ser Leu Gly Gly
225                 230                 235                 240

Tyr Val Phe Gly Thr Gly Thr Gln Leu Thr Val Leu Gly Ala Ala Ala
                245                 250                 255


<210> SEQ ID NO 52
<211> LENGTH: 744
<212> TYPE: DNA
<213> ORGANISM: Escherichia coli
```

```
<220> FEATURE:
<221> NAME/KEY: CDS
<222> LOCATION: (1)..(744)

<400> SEQUENCE: 52

atg gag cag gtg cag ctg cag gag tct ggg gga ggc ttg gta cag cct       48
Met Glu Gln Val Gln Leu Gln Glu Ser Gly Gly Gly Leu Val Gln Pro
1               5                   10                  15

ggg ggg tcc ctg aga ctc tcc tgt gca gcc tct gga ttc acc ttt agt       96
Gly Gly Ser Leu Arg Leu Ser Cys Ala Ala Ser Gly Phe Thr Phe Ser
            20                  25                  30

act tat gcc atg agc tgg gtc cgc cag gct cca ggg aag ggg ctg gag      144
Thr Tyr Ala Met Ser Trp Val Arg Gln Ala Pro Gly Lys Gly Leu Glu
        35                  40                  45

tgg gtc tca gtt att agt ggt agt ggt cat aca aca aac tac gcc gac      192
Trp Val Ser Val Ile Ser Gly Ser Gly His Thr Thr Asn Tyr Ala Asp
    50                  55                  60

tcc gtg aag ggc cgc gtc acc ata tcc aga gac aat tcc aag aac aca      240
Ser Val Lys Gly Arg Val Thr Ile Ser Arg Asp Asn Ser Lys Asn Thr
65                  70                  75                  80

cta tat ctg caa atc aac agc ctg aga gcc gac gac acg gcc gtg tat      288
Leu Tyr Leu Gln Ile Asn Ser Leu Arg Ala Asp Asp Thr Ala Val Tyr
                85                  90                  95

tac tgt gcg aga gat gtg tta gtc cta cag aat gct ttt gat atc tgg      336
Tyr Cys Ala Arg Asp Val Leu Val Leu Gln Asn Ala Phe Asp Ile Trp
            100                 105                 110

ggc caa ggg acc acg gtc acc gtc tcc tca ggt gga ggt ggt tca ggc      384
Gly Gln Gly Thr Thr Val Thr Val Ser Ser Gly Gly Gly Gly Ser Gly
        115                 120                 125

gga ggt ggc tct ggc ggt ggc gga tcg gat gtt gtg atg acc cag tct      432
Gly Gly Gly Ser Gly Gly Gly Gly Ser Asp Val Val Met Thr Gln Ser
    130                 135                 140

cca tcc tca ctg tct gca tct gta gga gac aga gtc acc atc act tgt      480
Pro Ser Ser Leu Ser Ala Ser Val Gly Asp Arg Val Thr Ile Thr Cys
145                 150                 155                 160

cgg gcg agt cag ggt att agc agg tgg tta gcc tgg tat caa cag aaa      528
Arg Ala Ser Gln Gly Ile Ser Arg Trp Leu Ala Trp Tyr Gln Gln Lys
                165                 170                 175

cca ggg aaa gcc cct aag ctc ctg atc tac gct gca tcc agt ttg caa      576
Pro Gly Lys Ala Pro Lys Leu Leu Ile Tyr Ala Ala Ser Ser Leu Gln
            180                 185                 190

agt ggg gtc cca tca agg ttc agt ggc agt gga tct ggg aca gat ttc      624
Ser Gly Val Pro Ser Arg Phe Ser Gly Ser Gly Ser Gly Thr Asp Phe
        195                 200                 205

act ctc acc atc agc agt ctg caa cct gaa gat ttt gca act tac atc      672
Thr Leu Thr Ile Ser Ser Leu Gln Pro Glu Asp Phe Ala Thr Tyr Ile
    210                 215                 220

tgt caa cag agt tac agt agg ccg ctc act ttc ggc gga ggg acc aag      720
Cys Gln Gln Ser Tyr Ser Arg Pro Leu Thr Phe Gly Gly Gly Thr Lys
225                 230                 235                 240

gtg gaa atc aaa cgt gcg gcc gca                                      744
Val Glu Ile Lys Arg Ala Ala Ala
                245


<210> SEQ ID NO 53
<211> LENGTH: 248
<212> TYPE: PRT
<213> ORGANISM: Escherichia coli

<400> SEQUENCE: 53

Met Glu Gln Val Gln Leu Gln Glu Ser Gly Gly Gly Leu Val Gln Pro
```

```
1               5                   10                  15

Gly Gly Ser Leu Arg Leu Ser Cys Ala Ala Ser Gly Phe Thr Phe Ser
            20                  25                  30

Thr Tyr Ala Met Ser Trp Val Arg Gln Ala Pro Gly Lys Gly Leu Glu
        35                  40                  45

Trp Val Ser Val Ile Ser Gly Ser Gly His Thr Thr Asn Tyr Ala Asp
    50                  55                  60

Ser Val Lys Gly Arg Val Thr Ile Ser Arg Asp Asn Ser Lys Asn Thr
65                  70                  75                  80

Leu Tyr Leu Gln Ile Asn Ser Leu Arg Ala Asp Asp Thr Ala Val Tyr
                85                  90                  95

Tyr Cys Ala Arg Asp Val Leu Val Leu Gln Asn Ala Phe Asp Ile Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Val Val Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Gly Ile Ser Arg Trp Leu Ala Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Ile
    210                 215                 220

Cys Gln Gln Ser Tyr Ser Arg Pro Leu Thr Phe Gly Gly Gly Thr Lys
225                 230                 235                 240

Val Glu Ile Lys Arg Ala Ala Ala
                245


<210> SEQ ID NO 54
<211> LENGTH: 7
<212> TYPE: PRT
<213> ORGANISM: Escherichia coli

<400> SEQUENCE: 54

Ser Asn Ser Ala Ala Trp Ser
1               5


<210> SEQ ID NO 55
<211> LENGTH: 5
<212> TYPE: PRT
<213> ORGANISM: Escherichia coli

<400> SEQUENCE: 55

Ser Tyr Tyr Trp Ser
1               5


<210> SEQ ID NO 56
<211> LENGTH: 7
<212> TYPE: PRT
<213> ORGANISM: Escherichia coli

<400> SEQUENCE: 56

Gly Ser Ser Asn Tyr Trp Gly
1               5
```

<210> SEQ ID NO 57
<211> LENGTH: 18
<212> TYPE: PRT
<213> ORGANISM: Escherichia coli

<400> SEQUENCE: 57

Thr Arg Tyr Tyr Arg Ser Lys Trp Tyr Asn Asp Tyr Ala Leu Ser Val
1 5 10 15

Lys Ser

<210> SEQ ID NO 58
<211> LENGTH: 16
<212> TYPE: PRT
<213> ORGANISM: Escherichia coli

<400> SEQUENCE: 58

Arg Ile Tyr Ala Ser Gly Arg Pro Lys Tyr Asn Pro Ser Leu Lys Ser
1 5 10 15

<210> SEQ ID NO 59
<211> LENGTH: 16
<212> TYPE: PRT
<213> ORGANISM: Escherichia coli

<400> SEQUENCE: 59

Ser Ile His Tyr Ile Gly Thr Thr Tyr Tyr Asn Pro Ser Phe Lys Ser
1 5 10 15

<210> SEQ ID NO 60
<211> LENGTH: 16
<212> TYPE: PRT
<213> ORGANISM: Escherichia coli

<400> SEQUENCE: 60

Ser Thr His Tyr Ile Gly Thr Thr Tyr Tyr Asn Pro Ser Phe Lys Ser
1 5 10 15

<210> SEQ ID NO 61
<211> LENGTH: 18
<212> TYPE: PRT
<213> ORGANISM: Escherichia coli

<400> SEQUENCE: 61

Trp Lys Ala Phe Thr Ala Val Ala Gly Pro Asn Tyr Tyr Tyr Gly Met
1 5 10 15

Asp Val

<210> SEQ ID NO 62
<211> LENGTH: 17
<212> TYPE: PRT
<213> ORGANISM: Escherichia coli

<400> SEQUENCE: 62

Val Tyr Ser Ser Ser Leu Thr Asp Phe Asp Tyr Tyr Tyr Gly Leu Asp
1 5 10 15

Val

<210> SEQ ID NO 63
<211> LENGTH: 17
<212> TYPE: PRT
<213> ORGANISM: Escherichia coli

<400> SEQUENCE: 63

Val Cys Ser Ser Ser Leu Thr Asp Phe Asp Tyr Tyr Tyr Gly Leu Asp
1 5 10 15

Val

<210> SEQ ID NO 64
<211> LENGTH: 9
<212> TYPE: PRT
<213> ORGANISM: Escherichia coli

<400> SEQUENCE: 64

Arg Thr Arg Trp Cys Trp Phe Asp Pro
1 5

<210> SEQ ID NO 65
<211> LENGTH: 5
<212> TYPE: PRT
<213> ORGANISM: Escherichia coli

<400> SEQUENCE: 65

Asn Tyr Ser Leu Asn
1 5

<210> SEQ ID NO 66
<211> LENGTH: 5
<212> TYPE: PRT
<213> ORGANISM: Escherichia coli

<400> SEQUENCE: 66

Asn Tyr Ser Phe Asn
1 5

<210> SEQ ID NO 67
<211> LENGTH: 5
<212> TYPE: PRT
<213> ORGANISM: Escherichia coli

<400> SEQUENCE: 67

Ser Tyr Trp Ile Asp
1 5

<210> SEQ ID NO 68
<211> LENGTH: 5
<212> TYPE: PRT
<213> ORGANISM: Escherichia coli

<400> SEQUENCE: 68

Asn Tyr Trp Ile Asp
1 5

<210> SEQ ID NO 69
<211> LENGTH: 5
<212> TYPE: PRT
<213> ORGANISM: Escherichia coli

<400> SEQUENCE: 69

Ser Tyr Ala Met Asn
1 5

<210> SEQ ID NO 70
<211> LENGTH: 17
<212> TYPE: PRT
<213> ORGANISM: Escherichia coli

<400> SEQUENCE: 70

Ala Ile Ser Ser Ser Gly Thr Tyr Arg Phe Tyr Ala Asp Ser Leu Arg
1 5 10 15

Gly

<210> SEQ ID NO 71
<211> LENGTH: 17
<212> TYPE: PRT
<213> ORGANISM: Escherichia coli

<400> SEQUENCE: 71

Ala Ile Ser Arg Ser Gly Thr Tyr Arg Phe Tyr Ala Asp Ser Leu Arg
1 5 10 15

Gly

<210> SEQ ID NO 72
<211> LENGTH: 17
<212> TYPE: PRT
<213> ORGANISM: Escherichia coli

<400> SEQUENCE: 72

Ile Ile Tyr Pro Asp Asp Ser Asp Thr Arg Tyr Ser Pro Ser Phe Gln
1 5 10 15

Gly

<210> SEQ ID NO 73
<211> LENGTH: 17
<212> TYPE: PRT
<213> ORGANISM: Escherichia coli

<400> SEQUENCE: 73

Ser Ile Ser Gly Ser Gly Ile Gly Thr Tyr Tyr Ala Asn Ser Val Gln
1 5 10 15

Gly

<210> SEQ ID NO 74
<211> LENGTH: 13
<212> TYPE: PRT
<213> ORGANISM: Escherichia coli

<400> SEQUENCE: 74

Asp Leu Gly Asp Leu Glu Trp Leu His Ser Pro Asp Pro
1 5 10

<210> SEQ ID NO 75
<211> LENGTH: 13
<212> TYPE: PRT
<213> ORGANISM: Escherichia coli

<400> SEQUENCE: 75

Asp Leu Gly Asp Leu Asp Trp Leu His Ser Pro Asp Pro
1 5 10

<210> SEQ ID NO 76
<211> LENGTH: 10
<212> TYPE: PRT
<213> ORGANISM: Escherichia coli

<400> SEQUENCE: 76

Arg Gly Asp Ser Gly Thr Leu Trp Gly Asp
1 5 10

<210> SEQ ID NO 77
<211> LENGTH: 13
<212> TYPE: PRT
<213> ORGANISM: Escherichia coli

<400> SEQUENCE: 77

Asp Glu Leu Asn Gln Leu Pro Gly Tyr Tyr Phe Asp Tyr
1 5 10

<210> SEQ ID NO 78
<211> LENGTH: 30
<212> TYPE: DNA
<213> ORGANISM: Artificial
<220> FEATURE:
<223> OTHER INFORMATION: synthetic primer

<400> SEQUENCE: 78 gaggaagctt ccattaaacg ggtaaaatac 30

<210> SEQ ID NO 79
<211> LENGTH: 40
<212> TYPE: DNA
<213> ORGANISM: Artificial
<220> FEATURE:
<223> OTHER INFORMATION: synthetic primer

<400> SEQUENCE: 79 tgcaatggcg gccgctaata ttgttctgga tattaccagc 40

<210> SEQ ID NO 80
<211> LENGTH: 72
<212> TYPE: DNA
<213> ORGANISM: Artificial
<220> FEATURE:
<223> OTHER INFORMATION: synthetic primer

<400> SEQUENCE: 80 agcttcctca tgtaggcggc cgcaggagac tacaaagacg acgacgacaa acaccaccat 60 caccaccatt aa 72

<210> SEQ ID NO 81
<211> LENGTH: 72
<212> TYPE: DNA
<213> ORGANISM: Artificial
<220> FEATURE:
<223> OTHER INFORMATION: synthetic primer

<400> SEQUENCE: 81 ggccttaatg gtggtgatgg tggtgtttgt cgtcgtcgtc tttgtagtct cctgcggccg 60 cctacatgag ga 72

<210> SEQ ID NO 82
<211> LENGTH: 106
<212> TYPE: DNA
<213> ORGANISM: Artificial
<220> FEATURE:
<223> OTHER INFORMATION: synthetic primer

<400> SEQUENCE: 82 agcttataaa ggaggaaatc ctcatgaaac agagcaccat cgcactggca ctgttaccgt 60 tactgttcac cccggttacc aaagcacgta ccatggtttc ccttgc 106

<210> SEQ ID NO 83

<211> LENGTH: 106
<212> TYPE: DNA
<213> ORGANISM: Artificial
<220> FEATURE:
<223> OTHER INFORMATION: synthetic primer

<400> SEQUENCE: 83 ggccgcaagg gaaaccatgg tacgtgcttt ggtaaccggg gtgaacagta acggtaacag 60 tgccagtgcg atggtgctct gtttcatgag gatttcctcc tttata 106

<210> SEQ ID NO 84
<211> LENGTH: 39
<212> TYPE: DNA
<213> ORGANISM: Artificial
<220> FEATURE:
<223> OTHER INFORMATION: synthetic primer

<400> SEQUENCE: 84 gtggtgatgg aattctttgt cgtcgtcgtc tttgtagtc 39

<210> SEQ ID NO 85
<211> LENGTH: 40
<212> TYPE: DNA
<213> ORGANISM: Artificial
<220> FEATURE:
<223> OTHER INFORMATION: synthetic primer

<400> SEQUENCE: 85 caccattaag gatcctaata ttgttctgga tattaccagc 40

<210> SEQ ID NO 86
<211> LENGTH: 40
<212> TYPE: DNA
<213> ORGANISM: Artificial
<220> FEATURE:
<223> OTHER INFORMATION: primers

<400> SEQUENCE: 86 tctattctga attcgctgaa actgttgaaa gttgtttagc 40

<210> SEQ ID NO 87
<211> LENGTH: 38
<212> TYPE: DNA
<213> ORGANISM: Artificial
<220> FEATURE:
<223> OTHER INFORMATION: primers

<400> SEQUENCE: 87 gccaatcgga attcctgcct caacctcctg tcaatgct 38

<210> SEQ ID NO 88
<211> LENGTH: 37
<212> TYPE: DNA
<213> ORGANISM: Artificial
<220> FEATURE:
<223> OTHER INFORMATION: primer

<400> SEQUENCE: 88 gaactgggat ccttaagact ccttattacg cagtatg 37

<210> SEQ ID NO 89
<211> LENGTH: 50
<212> TYPE: DNA
<213> ORGANISM: Artificial
<220> FEATURE:
<223> OTHER INFORMATION: primer

<400> SEQUENCE: 89 acccgtaagc ttataaagga ggaaatcctc atgaaataga gcaccatcgc 50

<210> SEQ ID NO 90
<211> LENGTH: 21
<212> TYPE: DNA
<213> ORGANISM: Artificial
<220> FEATURE:
<223> OTHER INFORMATION: primer

<400> SEQUENCE: 90 tagccccctt attagcgttt g 21

<210> SEQ ID NO 91
<211> LENGTH: 24
<212> TYPE: DNA
<213> ORGANISM: Artificial
<220> FEATURE:
<223> OTHER INFORMATION: primer

<400> SEQUENCE: 91 gtcatcgtcg gaatcgtcat ctgc 24

<210> SEQ ID NO 92
<211> LENGTH: 39
<212> TYPE: DNA
<213> ORGANISM: Artificial
<220> FEATURE:
<223> OTHER INFORMATION: primer

<400> SEQUENCE: 92 tgtgcgaaaa gtaatgagtt tctttttgac tactggggc 39

<210> SEQ ID NO 93
<211> LENGTH: 24
<212> TYPE: DNA
<213> ORGANISM: Artificial
<220> FEATURE:
<223> OTHER INFORMATION: primer

<400> SEQUENCE: 93 ctattgccta cggcagccgc tgga 24

<210> SEQ ID NO 94
<211> LENGTH: 58
<212> TYPE: DNA
<213> ORGANISM: Artificial
<220> FEATURE:
<223> OTHER INFORMATION: primer

<400> SEQUENCE: 94 tccgccgaat accacatagg gcaaccacgg ataagaggag ttacagtaat agtcagcc 58

<210> SEQ ID NO 95
<211> LENGTH: 20
<212> TYPE: DNA
<213> ORGANISM: Artificial
<220> FEATURE:
<223> OTHER INFORMATION: primer

<400> SEQUENCE: 95 tttcgcacag taatatacgg 20

<210> SEQ ID NO 96
<211> LENGTH: 18
<212> TYPE: DNA

<213> ORGANISM: Artificial
<220> FEATURE:
<223> OTHER INFORMATION: primer

<400> SEQUENCE: 96 tatgtggtat tcggcgga 18

<210> SEQ ID NO 97
<211> LENGTH: 60
<212> TYPE: DNA
<213> ORGANISM: Artificial
<220> FEATURE:
<223> OTHER INFORMATION: primer

<400> SEQUENCE: 97 acttcagctc cggacacccg tccggctccg ggttccaccg ctccgccggc tcacggtgtc 60

<210> SEQ ID NO 98
<211> LENGTH: 60
<212> TYPE: DNA
<213> ORGANISM: Artificial
<220> FEATURE:
<223> OTHER INFORMATION: primer

<400> SEQUENCE: 98 cggagccgga cgggtgtccg gagctgaagt gacaccgtga gccggcggag cggtggaacc 60

<210> SEQ ID NO 99
<211> LENGTH: 23
<212> TYPE: DNA
<213> ORGANISM: Artificial
<220> FEATURE:
<223> OTHER INFORMATION: primer

<400> SEQUENCE: 99 ctagttcgtc gggttcgtcg gga 23

<210> SEQ ID NO 100
<211> LENGTH: 19
<212> TYPE: DNA
<213> ORGANISM: Artificial
<220> FEATURE:
<223> OTHER INFORMATION: primer

<400> SEQUENCE: 100 tcccgacgaa cccgacgaa 19

<210> SEQ ID NO 101
<211> LENGTH: 22
<212> TYPE: DNA
<213> ORGANISM: Artificial
<220> FEATURE:
<223> OTHER INFORMATION: primer

<400> SEQUENCE: 101 ggacacggct gctgtattac tg 22

<210> SEQ ID NO 102
<211> LENGTH: 18
<212> TYPE: DNA
<213> ORGANISM: Artificial
<220> FEATURE:
<223> OTHER INFORMATION: primer

<400> SEQUENCE: 102 gctgaggaga cggtgacc 18

The invention claimed is:

1. An isolated or purified vector suitable for efficient selection and affinity maturation of a recombinant antibody[, the recombinant antibody having a leader peptide and being] encoded by a recombinant antibody coding sequence, wherein the vector comprises *a leader sequence encoding a leader peptide expressed with the recombinant antibody,*

*the vector further comprising* at least one element able to reduce the expression level of said recombinant antibody, the at least one element being selected from a) a suppressed stop codon inside either the leader peptide or the recombinant antibody coding sequence;

b) a low-efficient promoter driving transcription of said recombinant antibody coding sequence; or c) an inhibitor of the promoter driving transcription of said recombinant antibody coding sequence; and wherein the vector comprises a further element able to provide an efficient display of said recombinant antibody, the further element comprising:

a) a sequence coding for a carboxy-terminal part of a minor coat protein pill fused to the recombinant antibody coding sequence;

b) a *sequence coding for a* leader peptide of the alkaline phosphatase of E. coli comprised as the leader [peptide of the recombinant antibody] *sequence*; and c) a coding sequence for the minor coat protein pill fused to the recombinant antibody coding sequence with no amber codon therebetween.

2. The vector according to claim 1 wherein the recombinant antibody includes: ScFv, active fragments of Abs, or humanized sequences of Abs.

3. The vector according to claim 1 wherein the vector is a plasmid, a phagemid or a phage.

4. The vector according to claim 1, said vector being a phagemid vector having the nucleotide sequence of SEQ ID NO: 1.

5. An in vitro host cell transformed with the vector according to claim 1.

6. A non-human host cell transformed with the vector according to claim 1.

7. The non-human host cell of claim 6, wherein the non-human host cell is a bacterial cell.

8. The vector of claim 1, wherein the vector is a DNA vector.

9. The in vitro host cell of claim 5, wherein the host cell is a bacterial cell.

*10. A method for improving selection and/or maturation of a recombinant antibody, the method comprising*

*cloning and expressing sequences encoding for recombinant antibodies with the vector according to claim 1; and*

*selecting a cloned and expressed recombinant antibody having an affinity for an antigen or target protein thus improving the selection and/or maturation of the recombinant antibody.*

*11. The method of claim 10, wherein the cloning and expressing comprises*

*constructing a phage display library for the recombinant antibody with the vector of claim 1 comprising the sequences encoding for the recombinant antibodies.*

*12. The method of claim 11, wherein the phage display library is selected from a synthetic or semi-synthetic antibody library, or a library mutated for affinity maturation of antibodies.*

*13. The method of claim 11, wherein the selecting comprises*

*performing affinity selection of the recombinant antibodies from the phage display library to obtain an affinity selected recombinant antibody having high affinity for the antigen or target protein.*

*14. The method of claim 11, wherein the phage display library -is a library mutated for affinity maturation of antibodies; and the selecting comprises*

*selecting a maturated recombinant antibody from the library mutated for affinity maturation of antibodies, the maturated recombinant antibody having an affinity for an antigen or target protein.*

*15. The method of claim 11, wherein the phage display library is a library mutated for affinity maturation of antibodies; and the selecting comprises*

*performing affinity selection of maturated recombinant antibodies from the library mutated for affinity maturation of antibodies to obtain an affinity maturated recombinant antibody having high affinity for an antigen or a target protein.*

*16. The method of claim 10, wherein the antigen or target protein is displayed on a cell.*

*17. The method of claim 10, wherein the sequences encoding for the recombinant antibodies comprise mutagenized sequences from an original sequence encoding for an original recombinant antibody.*

*18. The method of claim 10, wherein the sequences encoding for recombinant antibodies are derived from antibody producing cells.*

*19. The method of claim 18, wherein the antibody producing cells are Tumor Infiltrating Lymphocytes (TILs) or Peripheral Blood Lymphocytes (PBLs).*

*20. The method of claim 18, wherein the antibody producing cells are isolated from a tumor affected subject.*

*21. The method of claim 20, wherein the tumor affected subject is a breast cancer affected subject.*

* * * * *